(12) United States Patent
Downes et al.

(10) Patent No.: US 10,829,757 B2
(45) Date of Patent: Nov. 10, 2020

(54) MUB MOTIF IS AN INHIBITOR OF E2-UBIQUITIN THIOESTER FORMATION

(71) Applicant: Saint Louis University, St. Louis, MO (US)

(72) Inventors: Brian Downes, Edwardsville, IL (US); Sergey V. Korolev, Manchester, MO (US); Xiaolong Lu, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 16/087,737

(22) PCT Filed: Mar. 24, 2017

(86) PCT No.: PCT/US2017/024021
§ 371 (c)(1),
(2) Date: Sep. 24, 2018

(87) PCT Pub. No.: WO2017/165771
PCT Pub. Date: Sep. 28, 2017

(65) Prior Publication Data
US 2019/0085314 A1 Mar. 21, 2019

Related U.S. Application Data

(60) Provisional application No. 62/312,815, filed on Mar. 24, 2016.

(51) Int. Cl.
*A61K 38/00* (2006.01)
*C07K 14/00* (2006.01)
*C12N 9/94* (2006.01)
*C12N 9/00* (2006.01)

(52) U.S. Cl.
CPC ............. *C12N 9/93* (2013.01); *C07K 14/001* (2013.01); *A61K 38/00* (2013.01)

(58) Field of Classification Search
None
See application file for complete search history.

(56) References Cited

PUBLICATIONS

Dowil et al., *Arabidopsis* Membrane-anchored Ubiquitin-fold (MUB) Proteins Localize a Specific Subset of Ubiquitin-conjugating (E2) Enzymes to the Plasma Membrane, J. Biol. Chem. 286: 14913-14921 (2011) (Year: 2011).*

Brzovie, et al., "A UbcH5/ubiquitin noncovalent complex is required for processive BRCA1-directed ubiquitination." *Molecular Cell* 21.6 (2006): 873-880.
Brzovic, et al., "Ubiquitin transfer from the E2 perspective: why is UbcH5 so promiscuous?." *Cell Cycle* 5.24 (2006): 2867-2873.
Capili, et al., "Structure and analysis of a complex between SUMO and Ubc9 illustrates features of a conserved E2-Ubl interaction." *Journal of Molecular Biology* 369.3 (2007): 608-618.
Dou, et al., "BIRC7-E2 ubiquitin conjugate structure reveals the mechanism of ubiquitin transfer by a RING dimer." *Nature Structural & Molecular Biology* 19.9 (2012): 876, (21 pages).
Dowil, et al., "*Arabidopsis* membrane-anchored ubiquitin-fold (MUB) proteins localize a specific subset of ubiquitin-conjugating (E2) enzymes to the plasma membrane." *Journal of Biological Chemistry* 286.17 (2011): 14913-14921.
Downes, et al., "MUBs, a family of ubiquitin-fold proteins that are plasma membrane-anchored by prenylation." *Journal of Biological Chemistry* 281.37 (2006): 27145-27157.
Hibbert, et al., "E3 ligase Rad18 promotes monoubiquitination rather than ubiquitin chain formation by E2 enzyme Rad6." *Proceedings of the National Academy of Sciences* 108.14 (2011): 5590-5595.
Hsieh, et al., "A novel cell-penetrating peptide suppresses breast tumorigenesis by inhibiting β-catenin/LEF-1 signaling." *Scientific Reports* 6 (2016): 19156, (12 pages).
Huang, et al., "Identification of a 7-gene signature that predicts relapse and survival for early stage patients with cervical carcinoma." *Medical Oncology* 29.4 (2012): 2911-2918.
International Search Report and Written Opinion issued in PCT/US17/24021, dated Aug. 28, 2017.
Kamadurai, et al., "Insights into ubiquitin transfer cascades from a structure of a UbcH5B~ubiquitin-HECTNEDD4L complex." *Molecular Cell* 36.6 (2009): 1095-1102.
Kirisako, et al., "A ubiquitin ligase complex assembles linear polyubiquitin chains." *The EMBO Journal* 25.20 (2006): 4877-4887.
Knipscheer, et al., "Noncovalent interaction between Ubc9 and SUMO promotes SUMO chain formation." *The EMBO Journal* 26.11 (2007): 2797-2807.
Kus, et al., "Functional interaction of 13 yeast SCF complexes with a set of yeast E2 enzymes in vitro." *Proteins: Structure, Function, and Bioinformatics* 54.3 (2004): 455-467.
Lu, et al., "Designed semisynthetic protein inhibitors of Ub/Ubl E1 activating enzymes." *Journal of the American Chemical Society* 132.6 (2010): 1748-1749.
Lu, "*The membrane-anchored ubiquitin-fold protein (MUB) regulates ubiquitylation reactions.*" Diss. Saint Louis University, 2015, (105 pages).

(Continued)

*Primary Examiner* — Julie Ha
*Assistant Examiner* — Kristina M Hellman
(74) *Attorney, Agent, or Firm* — Parker Highlander PLLC

(57) ABSTRACT

The present disclosure provides for peptides derived from membrane-anchored ubiquitin-fold proteins (MUB), particularly those containing a Lap-Bar-Lopp motif, for use in inhibiting ubiquitinylation.

19 Claims, 26 Drawing Sheets
Specification includes a Sequence Listing.

(56) References Cited

PUBLICATIONS

Oláh, et al., "Interactions of pathological hallmark proteins tubulin polymerization promoting protein/p25, β-(amyloid, and α-synuclein." *Journal of Biological Chemistry* 286.39 (2011): 34088-34100.

Olsen, et al., "Active site remodelling accompanies thioester bond formation in the SUMO E1." *Nature* 463.7283 (2010): 906-912.

Rodrigo-Brenni, et al., "Sequential E2s drive polyubiquitin chain assembly on APC targets." *Cell* 130.1 (2007): 127-139.

Sakata, et al., "Crystal structure of UbcH5b~ubiquitin intermediate: insight into the formation of the self-assembled E2~Ub conjugates." *Structure* 18.1 (2010): 138-147.

Sakata, et al., "Direct interactions between NEDD8 and ubiquitin E2 conjugating enzymes upregulate cullin-based E3 ligase activity." *Nature Structural & Molecular Biology* 14.2 (2007): 167-168.

Sekizawa, et al., "Panepophenantbrin, from a mushroom strain, a novel inhibitor of the ubiquitin-activating enzyme," *Journal of Natural Products* 65.10 (2002): 1491-1493.

Soucy, el al., "An inhibitor of NEDD8-activating enzyme as a new approach to treat cancer." *Nature* 458.7239 (2009): 732-736.

Stone, et al., "Functional analysis of the RING-type ubiquitin ligase family of *Arabidopsis*." *Plant Physiology* 137.1 (2005): 13-30.

Tsukamoto, et al., "Himeic acid A: a new ubiquitin-activating enzyme inhibitor isolated from a marine-derived fungus, *Aspergillus* sp." *Bioorganic & Medicinal Chemistry Letters* 15.1 (2005): 191-194.

Ungermannova, et al., "Identification and mechanistic studies of a novel ubiquitin E1 inhibitor." *Journal of Bimolecular Screening* 17.4 (2012): 421-434.

Xu, el al., "The ubiquitin-activating enzyme E1 as a therapeutic target for the area merit of leukemia and multiple myeloma." *Blood* 115.11 (2010): 2251-2259.

Yang, et al., "Inhibitors of ubiquitin-activating enzyme (E1), a new class of potential cancer therapeutics." *Cancer Research* 67.19 (2007): 9472-9481.

Ye, et al., "Bilding ubiquitin chains: E2 enzymes at work" *Nature Reviews Molecular Cell Biology* 10.11 (2009): 755-764.

\* cited by examiner

|  | Input | | Output | |
|---|---|---|---|---|
| FLAG Resin | + | + | + | + |
| AtMUB3-FLAG | + | − | + | − |
| AtUBC8C85S~Ub | + | + | + | + |

15kDa — IB: AtMUB3
30kDa / 25kDa — IB: AtUBC8
30kDa / 25kDa — IB: UB

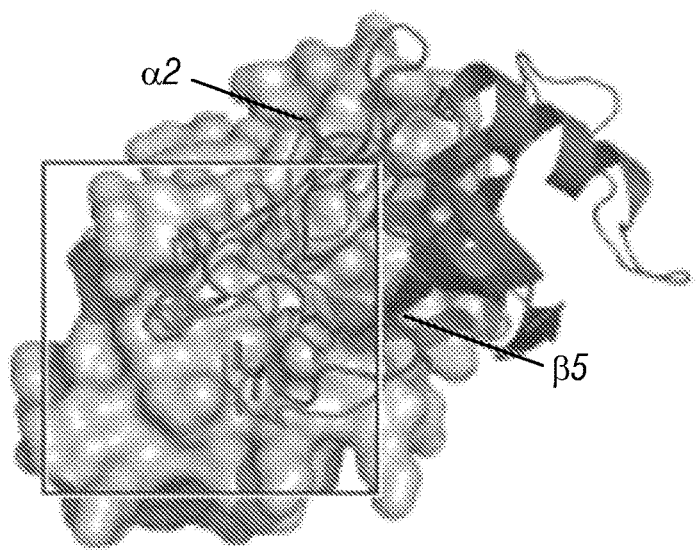

| Align: MUB | AtUBC8 BD: | | | | | | | | | | | | | | | | α2-β5 loop length (aa) |
|---|---|---|---|---|---|---|---|---|---|---|---|---|---|---|---|---|---|
| AtMUB3 | (70) | V | G | Q | C | K | T | P | F | G | D | I | A | G | G | V I V M H V V | 11 |
| AtMUB4 | (70) | V | A | Q | C | K | A | P | F | D | D | L | P | K | S | V I T M H V V | 11 |
| CsMUB3 | (70) | V | G | Q | C | K | L | P | F | G | E | F | T | G | G | V T I M H V V | 11 |
| CsMUB4 | (70) | V | G | Q | C | R | V | P | F | G | D | L | P | K | G | V I T M H V V | 11 |
| OsMUB3 | (71) | L | A | E | S | R | V | P | V | G | E | V | P | G | G | V I T M H V V | 11 |
| OsMUB4 | (87) | I | A | Q | C | R | A | P | F | G | D | L | P | S | T | A I T M H V V | 11 |
| StMUB3 | (71) | V | G | Q | C | K | T | P | F | G | E | L | P | N | G | V I T M H A V | 11 |
| StMUB4 | (70) | V | G | Q | C | K | T | P | F | G | E | L | P | N | G | V I T M H A V | 11 |
| HsMUB | (73) | L | G | A | L | K | L | P | F | G | K | - | - | - | - | T T V M H L V | 7 |
| MmMUB | (73) | L | G | A | L | K | L | P | F | G | K | - | - | - | - | T T V M H L V | 7 |
| AtUb | (57) | A | D | Y | N | I | Q | K | - | - | E | - | - | - | - | S T - L H L V | 4 |

Lap Bar

HECT E3 + Ub  RING E3 + Ub

OTUB DUB + Ub  Inhibitory Kinase + Ub r.m.s.d. = 0.7 A r.m.s.d. = 1.8 A r.m.s.d. = 0.8 A r.m.s.d. = 1.6 A AtMUB3

AtUBC8

SEQUENCE LISTING

```
<160> NUMBER OF SEQ ID NOS: 131

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Leu Lys Leu Pro Phe Gly Lys Thr
```

1          5

<210> SEQ ID NO 2
<211> LENGTH: 117
<212> TYPE: PRT
<213> ORGANISM: Homo sapiens

<400> SEQUENCE: 2

Met Ser Ser Asn Val Pro Ala Asp Met Ile Asn Leu Arg Leu Ile Leu
1               5                   10                  15

Val Ser Gly Lys Thr Lys Glu Phe Leu Phe Ser Pro Asn Asp Ser Ala
            20                  25                  30

Ser Asp Ile Ala Lys His Val Tyr Asp Asn Trp Pro Met Asp Trp Glu
        35                  40                  45

Glu Glu Gln Val Ser Ser Pro Asn Ile Leu Arg Leu Ile Tyr Gln Gly
    50                  55                  60

Arg Phe Leu His Gly Asn Val Thr Leu Gly Ala Leu Lys Leu Pro Phe
65                  70                  75                  80

Gly Lys Thr Thr Val Met His Leu Val Ala Arg Glu Thr Leu Pro Glu
                85                  90                  95

Pro Asn Ser Gln Gly Gln Arg Asn Arg Glu Lys Thr Gly Glu Ser Asn
            100                 105                 110

Cys Cys Val Ile Leu
        115

<210> SEQ ID NO 3
<211> LENGTH: 8
<212> TYPE: PRT
<213> ORGANISM: Homo sapiens

<400> SEQUENCE: 3

Leu Lys Leu Pro Phe Gly Lys Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Thr Leu Gly Phe Lys Leu Lys Pro
1               5

<210> SEQ ID NO 5
<211> LENGTH: 34
<212> TYPE: PRT
<213> ORGANISM: Artificial Sequence
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 16

```
<212> TYPE: PRT
<213> ORGANISM: Artificial Sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Arg Arg Trp Arg Arg Trp Trp Arg Arg Trp Trp Arg Arg Trp Arg Arg
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide

<400> SEQUENCE: 9

Arg Gly Gly Arg Leu Ser Tyr Ser Arg Arg Arg Phe Ser Thr Ser Thr
1               5                   10                  15

Gly Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Gly Arg Lys Lys Arg Arg Gln Arg Arg
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Arg Lys Lys Arg Arg Gln Arg Arg Arg
1               5

<210> SEQ ID NO 12
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Tyr Ala Arg Ala Ala Ala Arg Gln Ala Arg Ala
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Arg Arg Arg Arg Arg Arg Arg Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Lys Lys Lys Lys Lys Lys Lys Lys
1               5

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide
```

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial Sequence
<220> FEATURE:

<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial Sequence
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide

```
<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial Sequence
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 31
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Pro Pro Pro Pro Pro Pro Pro Pro Pro Pro Pro Pro Pro Pro
1               5                   10

<210> SEQ ID NO 33
<211> LENGTH: 18
<212> TYPE: PRT
<213> ORGANISM: Artificial Sequence
<220> FEATURE:
```

-continued

<223> OTHER INFORMATION: Synthetic peptide

<400> SEQUENCE: 33

Val Arg Leu Pro Pro Pro Val Arg Leu Pro Pro Pro Val Arg Leu Pro
1               5                   10                  15

Pro Pro

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Pro Arg Pro Leu Pro Pro Pro Arg Pro Gly
1               5                   10

<210> SEQ ID NO 35
<211> LENGTH: 30
<212> TYPE: PRT
<213> ORGANISM: Artificial Sequence
<220> FEATURE:
<223> OTHER INFORMATION: Synthetic peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 36
<211> LENGTH: 21
<212> TYPE: PRT
<213> ORGANISM: Artificial Sequence
<220> FEATURE:
<223> OTHER INFORMATION: Synthetic peptide

<400> SEQUENCE: 36

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial Sequence
<220> FEATURE:
<223> OTHER INFORMATION: Synthetic peptide

<400> SEQUENCE: 38

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Gly Gln Ala
            20                  25                  30

Thr Gln Ile Ala Lys
        35

<210> SEQ ID NO 39
<211> LENGTH: 28
<212> TYPE: PRT
<213> ORGANISM: Artificial Sequence
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial Sequence
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial Sequence
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 43
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial Sequence
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide

<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48

```
<211> LENGTH: 18
<212> TYPE: PRT
<213> ORGANISM: Artificial Sequence
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide

<400> SEQUENCE: 49

Gly Leu Thr Leu Lys Pro Lys Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic peptide

<400> SEQUENCE: 50

Thr Leu Phe Lys Leu Lys Gly Pro
1               5

<210> SEQ ID NO 51
<211> LENGTH: 30
<212> TYPE: PRT
<213> ORGANISM: Artificial sequence
<220> FEATURE:
<223> OTHER INFORMATION: Synthetic peptide

<400> SEQUENCE: 51

Leu Ile Tyr Gln Gly Arg Phe Leu His Gly Asn Val Thr Leu Gly Ala
1               5                   10                  15

Leu Lys Leu Pro Phe Gly Lys Thr Thr Val Met His Leu Val
            20                  25                  30

<210> SEQ ID NO 52
<211> LENGTH: 30
<212> TYPE: PRT
<213> ORGANISM: Artificial sequence
<220> FEATURE:
<223> OTHER INFORMATION: Synthetic peptide

<400> SEQUENCE: 52

Leu Gly Ala Leu Lys Leu Pro Phe Gly Lys Thr Thr Val Met His Leu
1               5                   10                  15

Val Ala Arg Glu Thr Leu Pro Glu Pro Asn Ser Gln Gly Gln
            20                  25                  30

<210> SEQ ID NO 53
<211> LENGTH: 30
<212> TYPE: PRT
<213> ORGANISM: Artificial sequence
<220> FEATURE:
<223> OTHER INFORMATION: Synthetic peptide
```

```
<400> SEQUENCE: 53

Arg Phe Leu His Gly Asn Val Thr Leu Gly Ala Leu Lys Leu Pro Phe
1               5                   10                  15

Gly Lys Thr Thr Val Met His Leu Val Ala Arg Glu Thr Leu
            20                  25                  30

<210> SEQ ID NO 54
<211> LENGTH: 25
<212> TYPE: PRT
<213> ORGANISM: Artificial sequence
<220> FEATURE:
<223> OTHER INFORMATION: Synthetic peptide

<400> SEQUENCE: 54

Leu Ile Tyr Gln Gly Arg Phe Leu His Gly Asn Val Thr Leu Gly Ala
1               5                   10                  15

Leu Lys Leu Pro Phe Gly Lys Thr Thr
            20                  25

<210> SEQ ID NO 55
<211> LENGTH: 25
<212> TYPE: PRT
<213> ORGANISM: Artificial sequence
<220> FEATURE:
<223> OTHER INFORMATION: Synthetic peptide

<400> SEQUENCE: 55

Leu Gly Ala Leu Lys Leu Pro Phe Gly Lys Thr Thr Val Met His Leu
1               5                   10                  15

Val Ala Arg Glu Thr Leu Pro Glu Pro
            20                  25

<210> SEQ ID NO 56
<211> LENGTH: 25
<212> TYPE: PRT
<213> ORGANISM: Artificial sequence
<220> FEATURE:
<223> OTHER INFORMATION: Synthetic peptide

<400> SEQUENCE: 56

Arg Phe Leu His Gly Asn Val Thr Leu Gly Ala Leu Lys Leu Pro Phe
1               5                   10                  15

Gly Lys Thr Thr Val Met His Leu Val
            20                  25

<210> SEQ ID NO 57
<211> LENGTH: 25
<212> TYPE: PRT
<213> ORGANISM: Artificial sequence
<220> FEATURE:
<223> OTHER INFORMATION: Synthetic peptide

<400> SEQUENCE: 57

Leu Lys Leu Pro Phe Gly Lys Thr Thr Val Met His Leu Val Ala Arg
1               5                   10                  15

Glu Thr Leu Pro Glu Pro Asn Ser Gln
            20                  25

<210> SEQ ID NO 58
<211> LENGTH: 25
<212> TYPE: PRT
<213> ORGANISM: Artificial sequence
<220> FEATURE:
<223> OTHER INFORMATION: Synthetic peptide
```

```
<400> SEQUENCE: 58

Asn Val Thr Leu Gly Ala Leu Lys Leu Pro Phe Gly Lys Thr Thr Val
1               5                   10                  15

Met His Leu Val Ala Arg Glu Thr Leu
            20                  25

<210> SEQ ID NO 59
<211> LENGTH: 20
<212> TYPE: PRT
<213> ORGANISM: Artificial sequence
<220> FEATURE:
<223> OTHER INFORMATION: Synthetic peptide

<400> SEQUENCE: 59

Asn Val Thr Leu Gly Ala Leu Lys Leu Pro Phe Gly Lys Thr Thr Val
1               5                   10                  15

Met His Leu Val
            20

<210> SEQ ID NO 60
<211> LENGTH: 20
<212> TYPE: PRT
<213> ORGANISM: Artificial sequence
<220> FEATURE:
<223> OTHER INFORMATION: Synthetic peptide

<400> SEQUENCE: 60

Leu Lys Leu Pro Phe Gly Lys Thr Thr Val Met His Leu Val Ala Arg
1               5                   10                  15

Glu Thr Leu Pro
            20

<210> SEQ ID NO 61
<211> LENGTH: 20
<212> TYPE: PRT
<213> ORGANISM: Artificial sequence
<220> FEATURE:
<223> OTHER INFORMATION: Synthetic peptide

<400> SEQUENCE: 61

Ala Leu Lys Leu Pro Phe Gly Lys Thr Thr Val Met His Leu Val Ala
1               5                   10                  15

Arg Glu Thr Leu
            20

<210> SEQ ID NO 62
<211> LENGTH: 20
<212> TYPE: PRT
<213> ORGANISM: Artificial sequence
<220> FEATURE:
<223> OTHER INFORMATION: Synthetic peptide

<400> SEQUENCE: 62

Gly Arg Phe Leu His Gly Asn Val Thr Leu Gly Ala Leu Lys Leu Pro
1               5                   10                  15

Phe Gly Lys Thr
            20

<210> SEQ ID NO 63
<211> LENGTH: 20
<212> TYPE: PRT
<213> ORGANISM: Artificial sequence
<220> FEATURE:
```

<223> OTHER INFORMATION: Synthetic peptide

<400> SEQUENCE: 63

Leu Gly Ala Leu Lys Leu Pro Phe Gly Lys Thr Thr Val Met His Leu
1               5                   10                  15

Val Ala Arg Glu
            20

<210> SEQ ID NO 64
<211> LENGTH: 20
<212> TYPE: PRT
<213> ORGANISM: Artificial sequence
<220> FEATURE:
<223> OTHER INFORMATION: Synthetic peptide

<400> SEQUENCE: 64

Arg Phe Leu His Gly Asn Val Thr Leu Gly Ala Leu Lys Leu Pro Phe
1               5                   10                  15

Gly Lys Thr Leu
            20

<210> SEQ ID NO 65
<211> LENGTH: 15
<212> TYPE: PRT
<213> ORGANISM: Artificial sequence
<220> FEATURE:
<223> OTHER INFORMATION: Synthetic peptide

<400> SEQUENCE: 65

Asn Val Thr Leu Gly Ala Leu Lys Leu Pro Phe Gly Lys Thr Thr
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: Synthetic peptide

<400> SEQUENCE: 66

Leu Lys Leu Pro Phe Gly Lys Thr Thr Val Met His Leu Val Ala
1               5                   10                  15

<210> SEQ ID NO 67
<211> LENGTH: 15
<212> TYPE: PRT
<213> ORGANISM: Artificial sequence
<220> FEATURE:
<223> OTHER INFORMATION: Synthetic peptide

<400> SEQUENCE: 67

Leu Gly Ala Leu Lys Leu Pro Phe Gly Lys Thr Thr Val Met His
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: Synthetic peptide

<400> SEQUENCE: 68

Gly Asn Val Thr Leu Gly Ala Leu Lys Leu Pro Phe Gly Lys Thr
1               5                   10                  15

```
<210> SEQ ID NO 69
<211> LENGTH: 15
<212> TYPE: PRT
<213> ORGANISM: Artificial sequence
<220> FEATURE:
<223> OTHER INFORMATION: Synthetic peptide

<400> SEQUENCE: 69

Val Thr Leu Gly Ala Leu Lys Leu Pro Phe Gly Lys Thr Thr Val
1               5                   10                  15

<210> SEQ ID NO 70
<211> LENGTH: 21
<212> TYPE: PRT
<213> ORGANISM: Arabidopsis thaliana

<400> SEQUENCE: 70

Val Gly Gln Cys Lys Thr Pro Phe Gly Asp Ile Ala Gly Gly Val Ile
1               5                   10                  15

Val Met His Val Val
            20

<210> SEQ ID NO 71
<211> LENGTH: 21
<212> TYPE: PRT
<213> ORGANISM: Arabidopsis thaliana

<400> SEQUENCE: 71

Val Ala Gln Cys Lys Ala Pro Phe Asp Asp Leu Pro Lys Ser Val Ile
1               5                   10                  15

Thr Met His Val Val
            20

<210> SEQ ID NO 72
<211> LENGTH: 21
<212> TYPE: PRT
<213> ORGANISM: Cucumis sativus

<400> SEQUENCE: 72

Val Gly Gln Cys Lys Leu Pro Phe Gly Glu Phe Thr Gly Gly Val Thr
1               5                   10                  15

Ile Met His Val Val
            20

<210> SEQ ID NO 73
<211> LENGTH: 21
<212> TYPE: PRT
<213> ORGANISM: Cucumis sativus

<400> SEQUENCE: 73

Val Gly Gln Cys Arg Val Pro Phe Gly Asp Leu Pro Lys Gly Val Ile
1               5                   10                  15

Thr Met His Val Val
            20

<210> SEQ ID NO 74
<211> LENGTH: 21
<212> TYPE: PRT
<213> ORGANISM: Oryza sativa

<400> SEQUENCE: 74

Leu Ala Glu Ser Arg Val Pro Val Gly Glu Val Pro Gly Gly Val Ile
1               5                   10                  15
```

Thr Met His Val Val
            20

<210> SEQ ID NO 75
<211> LENGTH: 21
<212> TYPE: PRT
<213> ORGANISM: Oryza sativa

<400> SEQUENCE: 75

Ile Ala Gln Cys Arg Ala Pro Phe Gly Asp Leu Pro Ser Thr Ala Ile
1               5                   10                  15

Thr Met His Val Val
            20

<210> SEQ ID NO 76
<211> LENGTH: 21
<212> TYPE: PRT
<213> ORGANISM: Solanum tuberosum

<400> SEQUENCE: 76

Val Gly Gln Cys Lys Thr Pro Phe Gly Glu Leu Pro Asn Gly Val Ile
1               5                   10                  15

Thr Met His Ala Val
            20

<210> SEQ ID NO 77
<211> LENGTH: 21
<212> TYPE: PRT
<213> ORGANISM: Solanum tuberosum

<400> SEQUENCE: 77

Val Gly Gln Cys Lys Thr Pro Phe Gly Glu Leu Pro Asn Gly Val Ile
1               5                   10                  15

Thr Met His Ala Val
            20

<210> SEQ ID NO 78
<211> LENGTH: 17
<212> TYPE: PRT
<213> ORGANISM: Homo sapiens

<400> SEQUENCE: 78

Leu Gly Ala Leu Lys Leu Pro Phe Gly Lys Thr Thr Val Met His Leu
1               5                   10                  15

Val

<210> SEQ ID NO 79
<211> LENGTH: 17
<212> TYPE: PRT
<213> ORGANISM: Mus musculus

<400> SEQUENCE: 79

Leu Gly Ala Leu Lys Leu Pro Phe Gly Lys Thr Thr Val Met His Leu
1               5                   10                  15

Val

<210> SEQ ID NO 80
<211> LENGTH: 14
<212> TYPE: PRT
<213> ORGANISM: Arabidopsis thaliana

<400> SEQUENCE: 80

Ala Asp Tyr Asn Ile Gln Lys Glu Ser Thr Leu His Leu Val
1               5                   10

<210> SEQ ID NO 81
<211> LENGTH: 27
<212> TYPE: PRT
<213> ORGANISM: Schizosaccharomyces pombe

<400> SEQUENCE: 81

Leu Glu Val Thr Met Leu Ser Ser Gly Val Ser Leu Leu Tyr Ala Asn
1               5                   10                  15

Phe Gln Pro Pro Lys Lys Leu Ala Glu Arg Leu
                20                  25

<210> SEQ ID NO 82
<211> LENGTH: 27
<212> TYPE: PRT
<213> ORGANISM: Homo sapiens

<400> SEQUENCE: 82

Leu Glu Ile Thr Met Leu Ser Gln Gly Val Ser Met Leu Tyr Ser Phe
1               5                   10                  15

Phe Met Pro Ala Ala Lys Leu Lys Glu Arg Leu
                20                  25

<210> SEQ ID NO 83
<211> LENGTH: 25
<212> TYPE: PRT
<213> ORGANISM: Arabidopsis thaliana

<400> SEQUENCE: 83

Leu Ser Ala Tyr Ser Ile Ser Cys Gly Ser Cys Leu Leu Phe Asn Ser
1               5                   10                  15

Met Phe Thr Arg His Lys Glu Arg Met
                20                  25

<210> SEQ ID NO 84
<211> LENGTH: 25
<212> TYPE: PRT
<213> ORGANISM: Arabidopsis thaliana

<400> SEQUENCE: 84

Leu Asn Ala Tyr Ser Ile Ser Cys Gly Ser Ser Leu Leu Tyr Asn Ser
1               5                   10                  15

Met Phe Ser Arg His Lys Glu Arg Met
                20                  25

<210> SEQ ID NO 85
<211> LENGTH: 29
<212> TYPE: PRT
<213> ORGANISM: Arabidopsis thaliana

<400> SEQUENCE: 85

Ser Lys Arg Ile Leu Lys Glu Leu Lys Asp Leu Gln Lys Asp Pro Pro
1               5                   10                  15

Thr Ser Cys Ser Ala Gly Pro Val Ala Glu Asp Met Phe
                20                  25

<210> SEQ ID NO 86
<211> LENGTH: 29
<212> TYPE: PRT
<213> ORGANISM: Arabidopsis thaliana

```
<400> SEQUENCE: 86

Ser Lys Arg Ile Leu Lys Glu Leu Lys Asp Leu Gln Lys Asp Pro Pro
1               5                   10                  15

Thr Ser Cys Ser Ala Gly Pro Val Ala Glu Asp Met Phe
            20                  25

<210> SEQ ID NO 87
<211> LENGTH: 29
<212> TYPE: PRT
<213> ORGANISM: Arabidopsis thaliana

<400> SEQUENCE: 87

Ser Lys Arg Ile Leu Lys Glu Leu Lys Asp Leu Gln Lys Asp Pro Pro
1               5                   10                  15

Thr Ser Cys Ser Ala Gly Pro Val Ala Glu Asp Met Phe
            20                  25

<210> SEQ ID NO 88
<211> LENGTH: 29
<212> TYPE: PRT
<213> ORGANISM: Homo sapiens

<400> SEQUENCE: 88

Leu Lys Arg Ile Gln Lys Glu Leu Ser Asp Leu Gln Arg Asp Pro Pro
1               5                   10                  15

Ala His Cys Ser Ala Gly Pro Val Gly Asp Asp Leu Phe
            20                  25

<210> SEQ ID NO 89
<211> LENGTH: 29
<212> TYPE: PRT
<213> ORGANISM: Homo sapiens

<400> SEQUENCE: 89

Leu Lys Arg Ile His Lys Glu Leu Asn Asp Leu Ala Arg Asp Pro Pro
1               5                   10                  15

Ala Gln Cys Ser Ala Gly Pro Val Gly Asp Asp Met Phe
            20                  25

<210> SEQ ID NO 90
<211> LENGTH: 29
<212> TYPE: PRT
<213> ORGANISM: Homo sapiens

<400> SEQUENCE: 90

Leu Lys Arg Ile Asn Lys Glu Leu Ser Asp Leu Ala Arg Asp Pro Pro
1               5                   10                  15

Ala Gln Cys Ser Ala Gly Pro Val Gly Asp Asp Met Phe
            20                  25

<210> SEQ ID NO 91
<211> LENGTH: 29
<212> TYPE: PRT
<213> ORGANISM: Saccharomyces cerevisiae

<400> SEQUENCE: 91

Ser Lys Arg Ile Ala Lys Glu Leu Ser Asp Leu Glu Arg Asp Pro Pro
1               5                   10                  15

Thr Ser Cys Ser Ala Gly Pro Val Gly Asp Asp Leu Tyr
            20                  25
```

<210> SEQ ID NO 92
<211> LENGTH: 29
<212> TYPE: PRT
<213> ORGANISM: Saccharomyces cerevisiae

<400> SEQUENCE: 92

Ser Lys Arg Ile Ala Lys Glu Leu Ser Asp Leu Gly Arg Asp Pro Pro
1               5                   10                  15

Ala Ser Cys Ser Ala Gly Pro Val Gly Asp Asp Leu Tyr
            20                  25

<210> SEQ ID NO 93
<211> LENGTH: 29
<212> TYPE: PRT
<213> ORGANISM: Schizosaccharomyces pombe

<400> SEQUENCE: 93

Leu Lys Arg Ile Asn Arg Glu Leu Ala Asp Leu Gly Lys Asp Pro Pro
1               5                   10                  15

Ser Ser Cys Ser Ala Gly Pro Val Gly Asp Asp Leu Phe
            20                  25

<210> SEQ ID NO 94
<211> LENGTH: 57
<212> TYPE: PRT
<213> ORGANISM: Arabidopsis thaliana

<400> SEQUENCE: 94

Arg Leu Met Arg Asp Phe Lys Arg Leu Gln Gln Asp Pro Pro Ala Gly
1               5                   10                  15

Ile Ser Gly Ala Pro Gln Asp Asn Asn Ile Met Leu Trp Asn Ala Val
            20                  25                  30

Ile Phe Gly Pro Asp Asp Thr Pro Trp Asp Gly Gly Thr Phe Lys Leu
            35                  40                  45

Ser Leu Val Val Glu Gln Ser Trp Thr
    50                  55

<210> SEQ ID NO 95
<211> LENGTH: 56
<212> TYPE: PRT
<213> ORGANISM: Arabidopsis thaliana

<400> SEQUENCE: 95

Ser Lys Arg Arg Glu Met Asp Met Met Lys Leu Met Met Ser Asp Tyr
1               5                   10                  15

Lys Val Asp Thr Val Asn Asp Asp Leu Gln Met Phe Tyr Val Thr Phe
            20                  25                  30

His Gly Pro Thr Asp Ser Leu Tyr Gln Gly Gly Val Trp Lys Ile Lys
            35                  40                  45

Val Tyr Cys Glu Lys Tyr Ala Lys
    50                  55

<210> SEQ ID NO 96
<211> LENGTH: 58
<212> TYPE: PRT
<213> ORGANISM: Arabidopsis thaliana

<400> SEQUENCE: 96

Leu Leu Gln Lys Gln Leu Lys Asp Leu Cys Lys His Pro Val Asp Gly
1               5                   10                  15

Phe Ser Ala Gly Leu Val Asp Glu Lys Asn Ile Phe Glu Trp Ser Val

```
                20                  25                  30
Thr Ile Ile Gly Pro Pro Asp Thr Leu Tyr Glu Gly Gly Phe Phe Tyr
            35                  40                  45

Ala Ile Met Cys Val Arg Lys Ser Gln Glu
        50                  55

<210> SEQ ID NO 97
<211> LENGTH: 55
<212> TYPE: PRT
<213> ORGANISM: Arabidopsis thaliana

<400> SEQUENCE: 97

Arg Leu Gln Lys Glu Phe Met Glu Trp Gln Thr Asn Pro Pro Ser Gly
1               5                   10                  15

Phe Lys His Arg Val Ser Asp Asn Leu Gln Arg Trp Ile Ile Glu Val
                20                  25                  30

His Gly Val Pro Gly Thr Leu Tyr Ala Asn Glu Thr Tyr Gln Leu Gln
            35                  40                  45

Val Phe His Asp Asp Lys Val
        50                  55

<210> SEQ ID NO 98
<211> LENGTH: 57
<212> TYPE: PRT
<213> ORGANISM: Arabidopsis thaliana

<400> SEQUENCE: 98

Gln Leu Ala Lys Glu Leu Lys Ser Leu Asp Glu Ser Pro Pro Asp Gly
1               5                   10                  15

Ile Lys Val Val Val Asn Asp Glu Asp Phe Ser Gln Ile Cys Ala Asp
                20                  25                  30

Ile Glu Gly Pro Val Gly Thr Pro Tyr Glu Asn Gly Leu Phe Arg Met
            35                  40                  45

Lys Leu Tyr Thr Gly Ile His Ala Lys
        50                  55

<210> SEQ ID NO 99
<211> LENGTH: 57
<212> TYPE: PRT
<213> ORGANISM: Arabidopsis thaliana

<400> SEQUENCE: 99

Lys Val Gln Gln Glu Trp Ser Asn Leu Glu Ala Asn Leu Pro Asn Thr
1               5                   10                  15

Ile Tyr Val Arg Val Cys Glu Glu Arg Met Asp Leu Leu Arg Ala Ala
                20                  25                  30

Leu Val Gly Ala Pro Gly Thr Pro Tyr His Asp Gly Leu Phe Phe Phe
            35                  40                  45

Asp Ile Ile Thr Cys Lys Ser Met Ile
        50                  55

<210> SEQ ID NO 100
<211> LENGTH: 58
<212> TYPE: PRT
<213> ORGANISM: Arabidopsis thaliana

<400> SEQUENCE: 100

Arg Ile Gln Lys Glu Leu Gln Asp Cys Glu Arg Asn Gln Asp Ser Ser
1               5                   10                  15
```

```
Gly Ile Arg Val Cys Pro Lys Ser Asp Asn Leu Thr Arg Leu Thr Gly
            20                  25                  30

Thr Ile Pro Gly Pro Ile Gly Thr Pro Tyr Glu Gly Thr Phe Gln
        35                  40                  45

Ile Asp Ile Trp Thr Glu Thr Phe Ala Lys
    50                  55

<210> SEQ ID NO 101
<211> LENGTH: 56
<212> TYPE: PRT
<213> ORGANISM: Arabidopsis thaliana

<400> SEQUENCE: 101

Arg Ile Ala Met Glu Tyr Arg Ala Met Ile Ser Lys Glu Ser Leu Phe
1               5                   10                  15

Ser Ile Gly Gln Asn Ser Asn Asn Ile Tyr Glu Trp Thr Ala Val Ile
            20                  25                  30

Arg Gly Pro Asp Gly Thr Pro Tyr Glu Gly Gly Met Phe Asn Leu Ser
        35                  40                  45

Ile Phe Thr Ala Arg His Ala Asn
    50                  55

<210> SEQ ID NO 102
<211> LENGTH: 57
<212> TYPE: PRT
<213> ORGANISM: Arabidopsis thaliana

<400> SEQUENCE: 102

Arg Leu Gln Lys Glu Tyr Arg Ala Leu Cys Lys Glu Pro Val Ser His
1               5                   10                  15

Val Val Ala Arg Pro Ser Pro Asn Asp Ile Leu Glu Trp His Tyr Val
            20                  25                  30

Leu Glu Gly Ser Glu Gly Thr Pro Phe Ala Gly Gly Phe Tyr Tyr Gly
        35                  40                  45

Lys Ile Tyr Val Glu Lys Tyr Ser Gln
    50                  55

<210> SEQ ID NO 103
<211> LENGTH: 57
<212> TYPE: PRT
<213> ORGANISM: Arabidopsis thaliana

<400> SEQUENCE: 103

Arg Ile Gln Arg Glu Met Ala Glu Leu Asn Ile Asp Pro Pro Pro Asp
1               5                   10                  15

Cys Ser Ala Gly Pro Lys Gly Asp Asn Leu Tyr His Trp Ile Ala Thr
            20                  25                  30

Ile Ile Gly Pro Ser Gly Thr Pro Tyr Glu Gly Gly Ile Phe Phe Leu
        35                  40                  45

Asp Ile Trp Thr Leu Arg Phe Ala Lys
    50                  55

<210> SEQ ID NO 104
<211> LENGTH: 57
<212> TYPE: PRT
<213> ORGANISM: Arabidopsis thaliana

<400> SEQUENCE: 104

Arg Ile Leu Lys Glu Leu Lys Asp Leu Gln Lys Asp Pro Pro Thr Ser
1               5                   10                  15
```

Cys Ser Ala Gly Pro Val Ala Glu Asp Met Phe His Trp Gln Ala Thr
            20                  25                  30

Ile Met Gly Pro Ser Glu Ser Pro Tyr Ala Gly Gly Val Phe Leu Val
            35                  40                  45

Thr Ile Trp Thr Gln Lys Tyr Ala Met
    50                  55

<210> SEQ ID NO 105
<211> LENGTH: 57
<212> TYPE: PRT
<213> ORGANISM: Arabidopsis thaliana

<400> SEQUENCE: 105

Arg Ile Leu Lys Glu Leu Lys Asp Leu Gln Lys Asp Pro Pro Thr Ser
1               5                   10                  15

Cys Ser Ala Gly Pro Val Ala Glu Asp Met Phe His Trp Gln Ala Thr
            20                  25                  30

Ile Met Gly Pro Ser Asp Ser Pro Tyr Ser Gly Gly Val Phe Leu Val
            35                  40                  45

Thr Ile Trp Thr Gln Lys Tyr Ala Met
    50                  55

<210> SEQ ID NO 106
<211> LENGTH: 57
<212> TYPE: PRT
<213> ORGANISM: Arabidopsis thaliana

<400> SEQUENCE: 106

Arg Ile Leu Lys Glu Leu Lys Asp Leu Gln Lys Asp Pro Pro Thr Ser
1               5                   10                  15

Cys Ser Ala Gly Pro Val Ala Glu Asp Met Phe His Trp Gln Ala Thr
            20                  25                  30

Ile Met Gly Pro Ser Asp Ser Pro Tyr Ser Gly Gly Val Phe Leu Val
            35                  40                  45

Thr Ile Trp Thr Gln Lys Tyr Ala Met
    50                  55

<210> SEQ ID NO 107
<211> LENGTH: 57
<212> TYPE: PRT
<213> ORGANISM: Arabidopsis thaliana

<400> SEQUENCE: 107

Arg Ile Leu Lys Glu Leu Lys Asp Leu Gln Lys Asp Pro Pro Thr Ser
1               5                   10                  15

Cys Ser Ala Gly Pro Val Ala Glu Asp Met Phe His Trp Gln Ala Thr
            20                  25                  30

Ile Met Gly Pro Ala Glu Ser Pro Tyr Ser Gly Gly Val Phe Leu Val
            35                  40                  45

Thr Ile Trp Thr Gln Lys Tyr Ala Met
    50                  55

<210> SEQ ID NO 108
<211> LENGTH: 57
<212> TYPE: PRT
<213> ORGANISM: Arabidopsis thaliana

<400> SEQUENCE: 108

Arg Ile Leu Lys Glu Leu Lys Asp Leu Gln Lys Asp Pro Pro Ser Asn

```
                1               5                  10                 15
Cys Ser Ala Gly Pro Val Ala Glu Asp Met Phe His Trp Gln Ala Thr
                20                  25                 30

Ile Met Gly Pro Pro Glu Ser Pro Tyr Ala Gly Gly Val Phe Leu Val
        35                  40                 45

Ser Ile Trp Thr Gln Lys Tyr Ala Met
    50                  55
```

<210> SEQ ID NO 109
<211> LENGTH: 57
<212> TYPE: PRT
<213> ORGANISM: Arabidopsis thaliana

<400> SEQUENCE: 109

```
Arg Ile Leu Lys Glu Leu Lys Glu Leu Gln Arg Asp Pro Pro Val Ser
1               5                  10                 15

Cys Ser Ala Gly Pro Thr Gly Glu Asp Met Phe His Trp Gln Ala Thr
                20                  25                 30

Ile Met Gly Pro Asn Glu Ser Pro Tyr Ser Gly Gly Val Phe Leu Val
        35                  40                 45

Asn Ile Trp Thr Gln Lys Tyr Ala Leu
    50                  55
```

<210> SEQ ID NO 110
<211> LENGTH: 57
<212> TYPE: PRT
<213> ORGANISM: Arabidopsis thaliana

<400> SEQUENCE: 110

```
Arg Ile Asn Lys Glu Leu Arg Asp Leu Gln Arg Asp Pro Pro Val Ser
1               5                  10                 15

Cys Ser Ala Gly Pro Thr Gly Asp Asp Met Phe Gln Trp Gln Ala Thr
                20                  25                 30

Ile Met Gly Pro Ala Asp Ser Pro Phe Ala Gly Gly Val Phe Leu Val
        35                  40                 45

Thr Ile Trp Thr Gln Lys Tyr Ala Met
    50                  55
```

<210> SEQ ID NO 111
<211> LENGTH: 58
<212> TYPE: PRT
<213> ORGANISM: Arabidopsis thaliana

<400> SEQUENCE: 111

```
Arg Ile Ser Arg Glu Leu Arg Asp Met Gln Arg His Pro Pro Ala Asn
1               5                  10                 15

Cys Ser Ala Gly Pro Val Ala Glu Glu Asp Ile Phe His Trp Gln Ala
                20                  25                 30

Thr Ile Met Gly Pro His Asp Ser Pro Tyr Ser Gly Gly Val Phe Thr
            35                  40                 45

Val Ser Ile Trp Thr Gln Lys Tyr Ala Met
        50                  55
```

<210> SEQ ID NO 112
<211> LENGTH: 57
<212> TYPE: PRT
<213> ORGANISM: Saccharomyces cerevisiae

<400> SEQUENCE: 112

```
Arg Ile Ala Lys Glu Leu Ser Asp Leu Gly Arg Asp Pro Pro Ala Ser
1               5                   10                  15

Cys Ser Ala Gly Pro Val Gly Asp Asp Leu Tyr His Trp Gln Ala Ser
            20                  25                  30

Ile Met Gly Pro Ser Asp Ser Pro Tyr Ala Gly Gly Val Phe Phe Leu
        35                  40                  45

Ser Ile Trp Thr Lys Lys Tyr Ala Val
    50              55
```

<210> SEQ ID NO 113
<211> LENGTH: 57
<212> TYPE: PRT
<213> ORGANISM: Saccharomyces cerevisiae

<400> SEQUENCE: 113

```
Arg Ile Ala Lys Glu Leu Ser Asp Leu Glu Arg Asp Pro Pro Thr Ser
1               5                   10                  15

Cys Ser Ala Gly Pro Val Gly Asp Asp Leu Tyr His Trp Gln Ala Ser
            20                  25                  30

Ile Met Gly Pro Ala Asp Ser Pro Tyr Ala Gly Gly Val Phe Phe Leu
        35                  40                  45

Ser Ile Trp Thr Lys Lys Tyr Ala Val
    50              55
```

<210> SEQ ID NO 114
<211> LENGTH: 57
<212> TYPE: PRT
<213> ORGANISM: Schizosaccharomyces pombe

<400> SEQUENCE: 114

```
Arg Ile Asn Arg Glu Leu Ala Asp Leu Gly Lys Asp Pro Pro Ser Ser
1               5                   10                  15

Cys Ser Ala Gly Pro Val Gly Asp Asp Leu Phe His Trp Gln Ala Thr
            20                  25                  30

Ile Met Gly Pro Ala Asp Ser Pro Tyr Ala Gly Gly Val Phe Phe Leu
        35                  40                  45

Ser Ile Trp Thr Arg Lys Tyr Ala Ile
    50              55
```

<210> SEQ ID NO 115
<211> LENGTH: 57
<212> TYPE: PRT
<213> ORGANISM: Homo sapiens

<400> SEQUENCE: 115

```
Arg Ile His Lys Glu Leu Asn Asp Leu Ala Arg Asp Pro Pro Ala Gln
1               5                   10                  15

Cys Ser Ala Gly Pro Val Gly Asp Asp Met Phe His Trp Gln Ala Thr
            20                  25                  30

Ile Met Gly Pro Asn Asp Ser Pro Tyr Gln Gly Gly Val Phe Phe Leu
        35                  40                  45

Thr Ile Trp Thr Gln Lys Tyr Ala Met
    50              55
```

<210> SEQ ID NO 116
<211> LENGTH: 57
<212> TYPE: PRT
<213> ORGANISM: Homo sapiens

<400> SEQUENCE: 116

```
Arg Ile Asn Lys Glu Leu Ser Asp Leu Ala Arg Asp Pro Pro Ala Gln
1               5                   10                  15

Cys Ser Ala Gly Pro Val Gly Asp Asp Met Phe His Trp Gln Ala Thr
            20                  25                  30

Ile Met Gly Pro Asn Asp Ser Pro Tyr Gln Gly Gly Val Phe Phe Leu
        35                  40                  45

Thr Ile Trp Thr Gln Lys Tyr Ala Met
    50                  55
```

<210> SEQ ID NO 117
<211> LENGTH: 57
<212> TYPE: PRT
<213> ORGANISM: Homo sapiens

<400> SEQUENCE: 117

```
Arg Ile Gln Lys Glu Leu Ser Asp Leu Gln Arg Asp Pro Pro Ala His
1               5                   10                  15

Cys Ser Ala Gly Pro Val Gly Asp Asp Leu Phe His Trp Gln Ala Thr
            20                  25                  30

Ile Met Gly Pro Pro Asp Ser Ala Tyr Gln Gly Gly Val Phe Phe Leu
        35                  40                  45

Thr Val Trp Thr Gln Lys Tyr Ala Met
    50                  55
```

<210> SEQ ID NO 118
<211> LENGTH: 11
<212> TYPE: PRT
<213> ORGANISM: Homo sapiens

<400> SEQUENCE: 118

```
Lys Thr Pro Phe Gly Asp Ile Ala Gly Gly Val
1               5                   10
```

<210> SEQ ID NO 119
<211> LENGTH: 11
<212> TYPE: PRT
<213> ORGANISM: Homo sapiens

<400> SEQUENCE: 119

```
Lys Thr Ala Phe Gly Asp Ile Ala Gly Gly Val
1               5                   10
```

<210> SEQ ID NO 120
<211> LENGTH: 11
<212> TYPE: PRT
<213> ORGANISM: Homo sapiens

<400> SEQUENCE: 120

```
Lys Thr Pro Ala Gly Asp Ile Ala Gly Gly Val
1               5                   10
```

<210> SEQ ID NO 121
<211> LENGTH: 11
<212> TYPE: PRT
<213> ORGANISM: Homo sapiens

<400> SEQUENCE: 121

```
Lys Thr Pro Phe Ala Asp Ile Ala Gly Gly Val
1               5                   10
```

<210> SEQ ID NO 122

```
<211> LENGTH: 11
<212> TYPE: PRT
<213> ORGANISM: Homo sapiens

<400> SEQUENCE: 122

Lys Thr Pro Phe Gly Ala Ile Ala Gly Gly Val
1               5                   10

<210> SEQ ID NO 123
<211> LENGTH: 11
<212> TYPE: PRT
<213> ORGANISM: Homo sapiens

<400> SEQUENCE: 123

Lys Thr Pro Phe Gly Asp Ala Ala Gly Gly Val
1               5                   10

<210> SEQ ID NO 124
<211> LENGTH: 11
<212> TYPE: PRT
<213> ORGANISM: Homo sapiens

<400> SEQUENCE: 124

Lys Thr Ala Ala Ala Ala Ala Ala Gly Gly Val
1               5                   10

<210> SEQ ID NO 125
<211> LENGTH: 13
<212> TYPE: PRT
<213> ORGANISM: Homo sapiens

<400> SEQUENCE: 125

Gly Ala Leu Lys Leu Pro Phe Gly Lys Thr Thr Val Met
1               5                   10

<210> SEQ ID NO 126
<211> LENGTH: 9
<212> TYPE: PRT
<213> ORGANISM: Homo sapiens

<400> SEQUENCE: 126

Asp Tyr Asn Ile Gln Glu Ser Val Met
1               5

<210> SEQ ID NO 127
<211> LENGTH: 9
<212> TYPE: PRT
<213> ORGANISM: Homo sapiens

<400> SEQUENCE: 127

Asp Tyr Asn Ile Gln Glu Ser Val Met
1               5

<210> SEQ ID NO 128
<211> LENGTH: 8
<212> TYPE: PRT
<213> ORGANISM: Homo sapiens

<400> SEQUENCE: 128

Leu Lys Leu Pro Phe Gly Lys Thr
1               5

<210> SEQ ID NO 129
<211> LENGTH: 8
<212> TYPE: PRT
```

```
<213> ORGANISM: Homo sapiens

<400> SEQUENCE: 129

Thr Leu Gly Phe Lys Leu Lys Pro
1               5

<210> SEQ ID NO 130
<211> LENGTH: 8
<212> TYPE: PRT
<213> ORGANISM: Homo sapiens

<400> SEQUENCE: 130

Gly Leu Thr Leu Lys Pro Lys Phe
1               5

<210> SEQ ID NO 131
<211> LENGTH: 8
<212> TYPE: PRT
<213> ORGANISM: Homo sapiens

<400> SEQUENCE: 131

Thr Leu Phe Lys Leu Lys Gly Pro
1               5
```

MUB MOTIF IS AN INHIBITOR OF E2-UBIQUITIN THIOESTER FORMATION

PRIORITY CLAIM

This application is a national phase application under 35 U.S.C. § 371 of International Application No. PCT/US2017/024021, filed Mar. 24, 2017, which claims benefit of priority to U.S. Provisional Application Ser. No. 62/312,815, filed Mar. 24, 2016, the entire contents of each of which are hereby incorporated by reference.

STATEMENT OF FEDERAL FUNDING

This invention was made with government support under grant no. 1R15GM096279-01 awarded by the National Institutes of Health. The government has certain rights in the invention.

BACKGROUND

I. Field

The present disclosure relates generally to the fields of cell biology and biochemistry.

II. Description of Related Art

The covalent attachment of ubiquitin (Ub) to a protein substrate occurs through the sequential activity of Ub E1 activating, E2 conjugating and E3 ligating enzymes (Berndsen and Wolberger, 2014; Callis, 2014), and has diverse regulatory functions in protein degradation, DNA repair, endocytosis, and many other aspects of cell biology (Ikeda et al., 2010; Vierstra, 2012). Each Ub must be activated by E1, an 80-100 KDa protein composed of two E2 coordinating arms atop an activation body. The arms consist of the ubiquitin fold domain (UFD) on one side, and the Cys, plus, first catalytic cysteine half (FCCH) domains on the other, bridged by the active and inactive adenylation domains (AAD and IAD, respectively) (Streich and Lima, 2014). The AAD forms Ub-AMP using $Mg^{2+}$-ATP and ubiquitin, which the Cys domain acquires in a thioester linkage before rotating away to allow a second activation in the vacated AAD, resulting in E1(Ub)2 (Olsen et al., 2010).

E1(Ub)2 is thought to recruit an E2 (Haas et al., 1988; Pickart et al., 1994) and catalyze an E2 thioester linkage to Ub (E2~Ub). Current models suggest the E1 UFD first interacts with the E2 in a distal conformation before rotating towards the opposed Cys domain to form a proximal configuration, placing the E1 and E2 active sites in range for Ub transfer (FIG. 1A) (Olsen and Lima, 2013). This elegant mechanism affords regulation potential, which is indeed employed between Ub-like protein tags (Ubls), but not traditionally within a Ubl family. For instance, Ubl E1-like enzymes for SUMO, Nedd8, and others do not activate Ub E2s, or vice versa (Capili and Lima, 2007a). In contrast, current models hold that the 37 diverse E2 enzymes of *Arabidopsis* are constitutively activated by either of two closely related E1s, UBA1 or UBA2 (Hatfield et al., 1997; Kraft et al., 2005). The extent to which Ub E1s select Ub E2s is largely unexplored; although it would impact basal choices in the assembly of highly combinatorial ubiquitylation complexes.

In large part, Ub signaling outcomes are determined by the Ub-topology assembled on a given substrate (Komander and Rape, 2012); for example, the addition of one Ub, or a Ub-chain shaped by the use of seven internal Ub lysines (Komander and Rape, 2012; Saracco et al., 2009). Functionally, mono-ubiquitylation is associated with the endocytosis apparatus and DNA maintenance (Guerra and Callis, 2012; Hoege et al., 2002), Lys48-linked Ub chains drive substrate degradation by the 26S proteasome (Smalle and Vierstra, 2004), and Lys63-linked Ub chains scaffold non-degradative protein complexes (Duncan et al., 2006; Wen et al., 2008). In vitro, E2s exhibit characteristic chain-building preferences that are strong for some E2 subfamilies such as Ube2S for Lys11-linked chains, Ube2K for Lys48-linked chains, Ube2NUbe2V1 for Lys63 chains (Ye and Rape, 2009), while the Ube2D subfamily require direction from an E3 (Brzovic and Klevit, 2006; Kirkpatrick et al., 2006).

In emerging studies, some E2s appear to control chain-building by scaffolding higher order complexes through a backside non-covalent binding site (BBS) distant from the active site Cys. For instance, the BBS of Ubc13 positions the UEV (Ubiquitin E2 Variant) Mms2 to orchestrate K63 chain assembly (Eddins et al., 2006). Ube2D3 and the SUMO E2 Ubc9 use the BBS to interact with Ub or SUMO, to enhance chain elongation (Brzovic et al., 2006; Knipscheer et al., 2007a), and the BBS of Rad6 promotes Ub chain assembly unless blocked by Rad18 (Hibbert et al., 2011). Recent advances in understanding the HECT, RBR, and APC E3s continue to reveal new E2 activities during the Ub-ligation cycle including unexplored avenues for Ub delivery into E3/substrate reactions and subsequent Ub chain assembly processes (Berndsen and Wolberger, 2014; Hochstrasser, 2006). Since E2s are dynamic members of the substrate modification complex, the processive nature of chain formation remains elusive (Eletr et al., 2005). How Ub chain topologies arise mechanistically, and whether the timing and positioning of E2 activation plays a role are key outstanding questions.

An interest in early regulation of the ubiquitylation axis drives the inventors' characterization of one representative family called Membrane-anchored Ubiquitin-fold (MUB) proteins. Although small at ~120 aa, MUBs are unlike other ubiquitin-fold proteins including SUMO and NEDD8, because they do not have a C-terminal GlyGly motif for substrate attachment, and are probably not ubiquitin-like substrate modifiers. Instead, the MUB C-terminal CaaX box motif is prenylated and drives plasma membrane (PM) association in plants (Downes et al., 2006). *Arabidopsis* MUBs1-6 interact specifically with the *Arabidopsis* Group VI E2 family, and the single *Homo sapiens* HsMUB interacts only with the homologous Ube2D subfamily (Dowil et al., 2011). This E2 subfamily is a significant source of conjugating activity containing ~20% of *Arabidopsis* E2 genes (7/37) and ~10% of human E2 genes (3/24) and includes many examples with abundant expression in vivo (Stone et al., 2005; Ye and Rape, 2009). The E2 subfamily is versatile, lacking Lys preference for chain-building, lacking N- or C-terminal extensions to the E2 core (Brzovic and Klevit, 2006), and promiscuous; functioning with all E3 families tested in vitro including HECT (Kamadurai et al., 2009), RING (Brzovic et al., 2006; Dou et al., 2012), RBR (Kirisako et al., 2006), SCF (Kus et al., 2004), and APC (Rodrigo-Brenni and Morgan, 2007).

SUMMARY

Thus, in accordance with the present disclosure, there is provided a method for inhibiting ubiquitin conjugating enzyme activity comprising contacting a said enzyme with a peptide comprising a membrane-anchored ubiquitin-fold lap bar loop (MUB-LBL) under conditions permitting the interaction of said peptide and said enzyme. The peptide may consist of between 8 and 50 residues, including any specific integer therebetween such as 8, 9, 10, 11, 12, 13, 14, 15, 16, 17, 18, 19, 20, 21, 22, 23, 24, 25, 26, 27, 28, 29, 30, 35, 40, 45 or 50 residues. The peptide may contains no more than about 30, 25, 20, 19, 18, 17, 16, 15, 14, 13, 12, 11, 10, 9 or 8 consecutive residues of MUB-LBL. The MUB-LBL may comprise the sequence LKLPFGKT (SEQ ID NO: 1).

The peptide may be fused to a cell penetrating domain or a stabilization domain. The peptide may comprises all L-amino acids, all D-amino acids, or a mix of D- and L-amino acids. The enzyme may be a mammalian E2 enzyme, such as a human E2 enzyme. The enzyme may be a plant E2 enzyme. The enzyme may be located in a cell, such as in a mammalian subject, in a human subject or in an intact plant. The mammalian subject may suffer from a disorder involving pathologic ubiquitin activity, such as cancer. The plant may be subject to a disorder involving pathologic ubiquitin activity. Alternatively, the plant may have nutritional value and the method may improve the nutritional quality of the plant.

In another embodiment, there is provided an isolated peptide comprising a membrane-anchored ubiquitin-fold lap bar loop (MUB-LBL). The peptide may consist of between 8 and 50 residues, including any specific integer therebetween such as 8, 9, 10, 11, 12, 13, 14, 15, 16, 17, 18, 19, 20, 21, 22, 23, 24, 25, 26, 27, 28, 29, 30, 35, 40, 45 or 50 residues. The peptide may contains no more than about 30, 25, 20, 19, 18, 17, 16, 15, 14, 13, 12, 11, 10, 9 or 8 consecutive residues of MUB-LBL. The MUB-LBL may comprise the sequence LKLPFGKT (SEQ ID NO: 1). The peptide may be disposed in a pharmaceutically acceptable medium, diluent, buffer or excipient.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Conformational changes are crucial to E1 activity including rotation (closed arrow) of the Ubiquitin-fold domain (UFD), which is required to efficiently position E2 for Ubiquitin (Ub) thioester (E2~Ub) formation. Active site cysteine residues (C, circled) move into proximity for trans-thiolation of Ub from E1 to E2. (FIG. 1B) Thioester formation time course demonstrates the delayed charging of AtUBC8 in the presence of AtMUB3. Reactions were started with Mg-ATP addition, and stopped with Laemmli sample buffer at indicated time points and analyzed by non-reducing (−βme, β-mercaptoethanol) and reducing (+βme) immunoblot (IB) with the indicated antibodies. (FIG. 1C) AtMUB3 inhibition of thioester formation was examined for AtUBC8 and AtUBC8S22R using immunoblot (IB) analysis with AtUBC8, AtMUB3 or Ub antibodies. All samples contained Mg-ATP, Ub, reaction buffer, and other reaction components as indicated. (FIG. 1D) Thioester formation assays of representative Group VI E2s (top panel IB), and non-Group VI E2s (bottom panel IB).

(FIG. 2A) Cartoon structure of the AtMUB3:AtUBC8 complex is colored and labeled. The generalized position of the unstructured AtMUB3 carboxyl-terminus containing an additional 19 amino acids (AA19) and site used for protein prenylation (CaaX*) are indicated. (FIG. 2B) Interacting surface of AtMUB3:AtUBC8 complex is presented in open book configuration. (FIG. 2C) AtMUB3:AtUBC8 complex side view, relative to FIG. 2A, with both amino-termini forward. (FIG. 2D) AtMUB3:AtUBC8 complex top view, relative to FIG. 2A. (FIG. 2E) A FLAG pull-down assay between FLAG-AtMUB3 and AtUBC8C85S~O~Ub. The input and output proteins were visualized by immunoblotting (IB). (FIG. 2F) The AtMUB3 and Ub BBS interactions are mapped on the AtUBC8 surface. (FIG. 2G) A GST pull-down assay between GST-AtUBC8 and AtMUB3-His or Ub. (FIG. 2H) A diagram of AtMUB3:AtUBC8 interactions with contact residues listed for each molecule and dashed lines indicating salt bridges. Residues used to disrupt binding in previous studies are underlined. See also FIGS. 6A-D, 7, and 8.

FIGS. 3A-E. The functionally conserved MUB LBL is stabilized by E2 surface interaction. (FIG. 3A) Structure-based sequence alignment for the Lap Bar region of the AtMUB3/4 protein family from Arabidopsis, Arabidopsis thaliana (At); cucumber, Cucumis sativus; rice, Oryza Sativa (Os); potato, Solanum tuberosum (St), and the single MUB proteins from human, Homo sapiens (Hs) and mouse, Mus musculus (Mm) (AtMUB3=SEQ ID NO: 70; AtMUB4=SEQ ID NO: 71; CsMUB3=SEQ ID NO: 72; CsMUB4=SEQ ID NO: 73; OsMUB3=SEQ ID NO: 74; OsMUB4=SEQ ID NO: 75; StMUB3=SEQ ID NO: 76; StMUB4=SEQ ID NO: 77; HsMUB=SEQ ID NO: 78; MmMUB=SEQ ID NO: 79; AtUb=SEQ ID NO: 80). Ubiquitin is included for comparison. (FIG. 3B) Structure of the AtMUB3 LBL is highlighted by a square. Secondary structures flanking the LBL in AtMUB3 are indicated. (FIG. 3C) Detailed view of the AtMUB3 LBL and AtUBC8 with interacting residues rendered with sticks. Salt bridges are shown as dashed lines. (FIG. 3D) b-factors are plotted on AtMUB3 (cartoon) viewed from the E2 perspective. Core residues of the bar are listed and flexible side arms are indicated with asterisks. (FIG. 3E) Superposition of Ub (red) modeled from a backside Ube2D3 binding structure, AtMUB1 alone in solution (purple blue), and the AtMUB3 (magenta):AtUBC8 (grey, surface) complex. LBLs in different states of the AtMUB1 NMR structure (asterisks) exhibit flexibility and various "open" conformations, while LBL residues in the AtMUB3 structure (sticks) are coordinated by the E2 surface demonstrating a "closed" conformation.

FIGS. 4A-D. Functionally conserved MUB LBL is sufficient for inhibition of E2~Ub formation. (FIG. 4A) Thioester Formation Assays, as described in FIG. 1, of AtUBC8 (top) and Ube2D3 (bottom), each exposed to both *Arabidopsis* and human MUBs. (FIG. 4B) Top panel, thioester formation assays of AtUBC8 exposed to N-LKLPFGKT-C (HsMUB LBL; SEQ ID NO: 3), three scrambled peptides or an amino acid mixture equimolar to the human LBL (AA control). Bottom panel, thioester formation assays of UBC8 exposed to HsMUB chimeric for the Ub α2β5 loop (HsMUBX). (FIG. 4C) Quantification of AtMUB3 LBL mutant protein inhibition was performed by normalization to WT as 100% (dashed line), +/−SEM and n=3 for all data points. AtMUB3 with the LBL core converted to alanines is P76A F77A G78A D79A I80A (All A). (FIG. 4D) An interaction study between AtUBC8 and AtMUB3 All A LBL mutant proteins was carried out using GST pull-down assays. The input and output proteins were visualized by immunoblotting (IB) as indicated. See also FIGS. 9A-B and 10.

(FIG. 5A) Structure-based sequence alignment for E1s (Valdez-Taubas and Pelham, 2005) in *Arabidopsis thaliana* (At), *Homo sapiens* (Hs) and *Schizosaccharomyces pombe* (Sp) focused on the UFD E2 interacting region (SpUba1=SEQ ID NO: 81; HsUba1=SEQ ID NO: 82; AtUBA1=SEQ ID NO: 83; AtUBA2=84; AtUBC8=SEQ ID NO: 85; AtUBC10=SEQ ID NO: 86; AtUBC28=SEQ ID NO: 87; HsUbcH5a=88; HsUbcH5b=SEQ ID NO: 89; HsUbcH5c=SEQ ID NO: 90; ScUbc4=SEQ ID NO: 91; ScUbc5=SEQ ID NO: 92; SpUbc4=SEQ ID NO: 93; AtMUB3=SEQ ID NO: 70). Cyan circles indicate residues that are most critical for E1 UFD:E2 docking and E2~Ub formation (Olsen and Lima, 2013). A structure-based sequence alignment for E2s (UBCs) in At, Hs, Sp, and *Saccharomyces cerevisiae* (Sc) focused on the region that interfaces with the MUB LBL. Residues in direct contact with E1 UFD and MUB are indicated by circles above and below the alignment, respectively. Magenta circles indicate residues that interact with the MUB Lap Bar region. Green circles indicate residues that are most critical for E1 UFD docking (Olsen and Lima, 2013). Residues structurally determined to contact both MUB and E1 are indicated with red rectangles highlighting regions of major E1 vs. MUB conflict for the E2 surface. The alignments are colored as described in FIGS. 3A-E. The MUB LBL sequence and secondary structure map is provided for reference. Lines between E1, E2, and MUB indicate structurally determined interactions. Red triangles indicate spatially conflicting residues. (FIG. 5B) Structural superposition model of E1, E2, and MUB. AtMUB3:AtUBC8 complex (in magenta and cyan) was superimposed to the SpUba1:SpUbc4:Ub:Mg-ATP complex using E2s for alignment. SpUba1 is featured in dark green and the E1 UFD is highlighted in light green, while the Ub, SpUbc4, and Mg-ATP are not shown (PDB code 4112). Secondary structures for Uba1 are labeled. Arrow indicates perspective for Panel C detail. Yellow star indicates the UFD hinge. (FIG. 5C) Detailed cartoon structure of MUB Lap Bar region (magenta) and E1 UFD (green tube) conflict region near the E2 N-terminal α-helix (AtUBC8 in cyan, SpUbc4 in dark blue, arrow indicates loop displacement in the current structure). The critical residues involved in contact and conflict are labeled and shown as stick representations. (FIG. 5D) No additional conflicts were obvious in structure models of the AtMUB3: AtUBC8 complex (magenta, cyan, respectively) docked to various Ub system Ube2D3 containing complexes constructed via E2 structure alignments. Structure models include portions of a HECT E3, NEDD4L HECT Domain (3JVZ) (Kamadurai et al., 2009); a RING E3, BRIC7 RING domain (4AUQ) (Dou et al., 2012); a deubiquitinating enzyme, OTUB1 (4LDT) (Wiener et al., 2013); and a prokaryotic inhibitory kinase, OSPG (4BVU) (Pruneda et al., 2014), which are colored purple blue, marine, forest green, and deep salmon, respectively. Ub is colored in red. (FIG. 5E) Model of MUB regulated E1 charging of E2 near the PM.

(FIG. 6A) AtUBC8 (present study), cyan, is superimposed to Ube2D3 (3UGB), grey. (FIG. 6B) AtMUB3 (present study), magenta, is superimposed to Ub (2FUH), red. (FIG. 6C) AtMUB3 (present study), magenta, is superimposed to AtMUB1 (1SE9), slate. (FIG. 6D) AtMUB3 (present study), magenta, is superimposed to HsSUMO1 (2UYZ), orange.

(FIG. 8A) The AtMUB3:AtUBC8 complex is presented in open book configuration with interacting residues depicted in stick format. Binding residues are colored magenta in AtMUB3 (Top panel), cyan in AtUBC8 (bottom panel). Secondary structures supporting the interaction residues are indicated. (FIG. 8B) Protein sequence alignment colored as in FIGS. 3A-E. Sequences above the space do not interact with MUB by yeast two-hybrid. (AtUBC01=SEQ ID NO: 94; AtUCB06=SEQ ID NO: 95; AtUBC13=SEQ ID NO: 96; AtUBC17=SEQ ID NO: 97; AtUBC22=SEQ ID NO: 98; AtUBC24=SEQ ID NO: 99; AtUBC27=SEQ ID NO: 100; AtUBC31=SEQ ID NO: 101; AtUBC33=SEQ ID NO: 102; AtCOP10=SEQ ID NO: 103; AtUBC10=SEQ ID NO: 104; AtUBC09=SEQ ID NO: 105; AtUBC28=SEQ ID NO: 106; AtUBC08=SEQ ID NO: 107; AtUBC11=SEQ ID NO: 108; AtUBC29=SEQ ID NO: 109; AtUBC30=SEQ ID NO: 110; AtUBC12=SEQ ID NO: 111; ScUbc5=SEQ ID NO: 112; ScUbc4=SEQ ID NO: 113; SpUbc4=SEQ ID NO: 114; HsUbe2D2=SEQ ID NO: 115; HsUbe2D3=SEQ ID NO: 116; HsUbe2D1=SEQ ID NO: 117)

DESCRIPTION OF ILLUSTRATIVE EMBODIMENTS

Figure 1A:
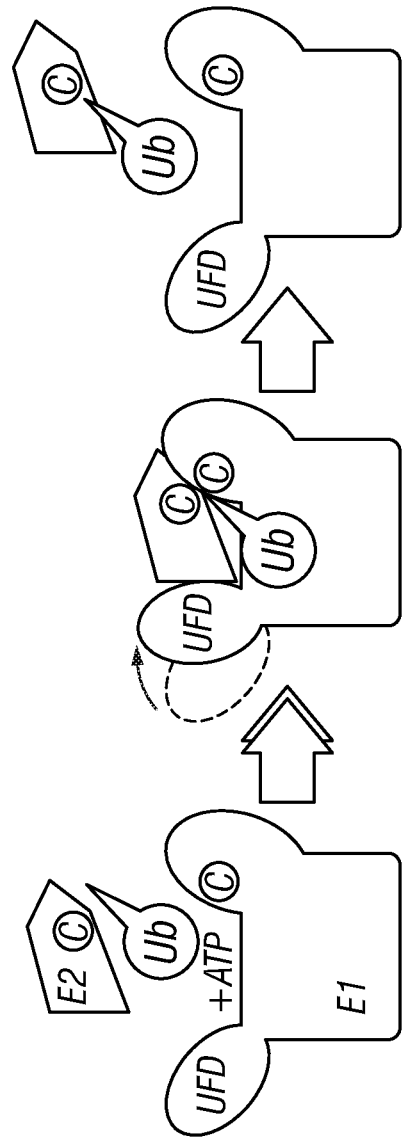
FIGS. 1A-D. AtMUB3 specifically inhibits activation of AtUBC8-like E2s.

It was previously reported that MUBs function as PM adapters for an E2 subfamily, but here the inventors show that MUBs specifically inhibit activation of these critical Ub E2's. This unique finding led the inventors to obtain a 2.8-Å co-crystal structure of AtMUB3 bound to AtUBC8. The structure reveals a mechanism for inhibition of E2~Ub formation that discriminates between cognate Ub E2's. This establishes a previously unappreciated point of regulation in the combinatorial complexity of ubiquitylation. The E2 active site remains accessible in the AtMUB3:AtUBC8 structure and should play an integral role in key ubiquitylation events near the PM. These and other aspects of the disclosure are described in greater detail below.

I. UBIQUITIN AND MEMBRANE-ANCHORED UBIQUITIN-FOLD (MUB) PROTEINS

Ubiquitin (Ub) is a post-translational modifier that controls numerous processes including endocytosis, DNA repair, selective protein degradation during the cell cycle, and many others; and consequently is a key underlying cause of cancers, neurodegenerative diseases, and a variety of other rare conditions when misregulated. Central to ubiquitylation is a three enzyme cascade: E1, E2, and E3, which act in sequence to activate, conjugate and ligate Ub to target substrate proteins.

Here, the inventors have identified the earliest acting protein regulator of this cascade discovered to date. The regulator, Membrane-anchored Ubiquitin-fold (MUB) protein, inhibits the transfer of Ub from the E1 to the E2 enzyme. A key MUB motif, which the inventors named the Lap Bar Loop (LBL), inhibits activation of a critical subset of E2s by masking them from the E1 UFD domain.

Ubiquitin (Ub)-fold proteins are an important class of eukaryotic modifiers that act post-translationally on other intracellular proteins. These molecules exhibit a common beta-grasp three-dimensional structure, but their functions are quite diverse due to distinct surface features and targets. Specific functions include tagging proteins for selective breakdown, nuclear import, autophagic recycling, vesicular trafficking, polarized morphogenesis, and the stress response.

The subject matter of this application relates to a particular family of proteins known as Membrane-anchored Ubfold (MUB) proteins present in animals, filamentous fungi, and plants. A typical MUB protein has a cysteine-containing CAAX (where A indicates aliphatic amino acid) sequence extending from the C-terminus of the Ub-fold that can direct the attachment of either a 15-carbon farnesyl or a 20-carbon geranylgeranyl moiety in vitro. Modified forms of several MUBs were detected in transgenic Arabidopsis thaliana, suggesting that these MUBs are prenylated in vivo. Analyses of Arabidopsis plants expressing GFP-MUB fusions showed that the modified forms are membrane-anchored with a significant enrichment on the plasma membrane. This plasma membrane location was blocked in vivo in prenyltransferase mutants and by mevinolin, which inhibits the synthesis of prenyl groups. In addition to the five MUBs with CAAX boxes, Arabidopsis has one MUB variant with a cysteine-rich C terminus distinct from the CAAX box that is also membrane-anchored, possibly through the attachment of a long chain acyl group.

The MUB gene family is conserved in eukaryotes and indicated in a variety of biological scenarios where human intervention would be useful. For instance, the human version of MUB, aka HsMUB or Ubl3, is structurally characterized by NMR (pdb:2GOW) and has a primary amino acid sequence: MSSNVPADMINLRLILVSGKTKE-FLFSPNDSASDIAKHVYDNWPMDWEEEQVSSPNIL RLIYQGRFLHGNVTLGALKLPFGKTTVMHLVARETL-PEPNSQGQRNREKTGESNCCVI L (SEQ ID NO: 2). Both the structure and sequence are conserved from plants to humans. Two areas where the ability to manipulate MUB action should prove useful are in recurring relapsing cancers and in neurodegenerative disease.

In cancer, HsMUB and PRCC (papillary renal cell carcinoma) a translocation-associated protein implicated in cell cycle progression were discovered to be significantly co-regulated in 3D brain scans, as described in Brown et al., (2002). HsMUB and PRCC association was noted in multiple organisms. Even more intriguing is the connection between HsMUB and recurrence of cervical cancer. HsMUB was determined to be a key gene of a 7-signature panel with high predictive value towards cancer recurrence and survival of cervical cancer patients by Huang et al. (2012). Finally, HsMUB gene expression is elevated among the most aggeressive cancer cell lines including metastatic breast adenocarcinoma and metastatic malignant melanoma (worldwide-web at proteinatlas.org/ENSG00000122042-UBL3/cell). Thus, MUB activation or interference could be utilized directly in manipulation of disease, or in the development of better diagnostics for detection and monitoring.

In neurodegeneration, HsMUB and neurodegenerative-implicated APP (amyloid beta (A4) precursor protein) were discovered together in reconstituted complexes, as described by Olah et al. (2011). Since the accumulation of protein plaques has been linked to failures in the ubiquitin system, it is plausible that a specialized MUB-dependent ubiquitylation reaction regulates APP clearance, or allows accumulation and disease in the disease state.

In all MUBs, the lap bar loop and E2 binding surface are predicted to be key components of activity. This structure and surface are conserved from plants to animals. Indeed, the functional conservation is demonstrated as a part of this disclosure.

II. DEFINITIONS

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

III. MUB PEPTIDES

A. Structure

The present disclosure relates in part to MUB LBL-based peptides. At its smallest, the peptide is just eight amino acids long, yet exerts potent inhibitory activity towards Ub transfer. The MUB α2β5 LBL region in all eukaryotes has been the subject of a comparative analysis, leading to numerous alternative forms. The human MUB LBL peptide described here is N-LKLPFGKT-C(HsLBLp1) (SEQ ID NO: 3).

In general, the peptides will be 50 residues or less in size, again, comprising no more than about 30, about 25, about 20 or about 15 consecutive residues of MUB. The overall length may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 8-50 residues, 9-50 residues, 10-50 residues, 11-50 residues, 8-25, residues, 8-20 residues, 9-20 residues, 10-20 residues, 11-20 residues, and 8-15 residues are contemplated. The number of consecutive MUB residues may be 4, 5, 6, 7, 8, 9, 10, 11, 12, 13, 14, 15, 16, 17, 18, 19 or 20. Ranges of consecutive residues of 8-20 residues, 9-20 residues, 10-20 residues, 11-20 residues and 8-15 residues, 9-15, residues, 10-15 residues or 11-15 residues are contemplated.

```
Particular 30-mer peptides include:
                                      (SEQ ID NO: 51)
LIYQGRFLHGNVTLGALKLPFGKTTVMHLV, (SEQ ID NO: 52)
LGALKLPFGKTTVMHLVARETLPEPNSQGQ,
and (SEQ ID NO: 53)
RFLHGNVTLGALKLPFGKTTVMHLVARETL.

Particular 25-mers include:
                                      (SEQ ID NO: 54)
LIYQGRFLHGNVTLGALKLPFGKTT, (SEQ ID NO: 55)
LGALKLPFGKTTVMHLVARETLPEP, (SEQ ID NO: 56)
RFLHGNVTLGALKLPFGKTTVMHLV, (SEQ ID NO: 57)
LKLPFGKTTVMHLVARETLPEPNSQ,
and (SEQ ID NO: 58)
NVTLGALKLPFGKTTVMHLVARETL.

Particular 20-mers include:
                                      (SEQ ID NO: 59)
NVTLGALKLPFGKTTVMHLV, (SEQ ID NO: 60)
LKLPFGKTTVMHLVARETLP, (SEQ ID NO: 61)
ALKLPFGKTTVMHLVARETL, (SEQ ID NO: 62)
GRFLHGNVTLGALKLPFGKT, (SEQ ID NO: 63)
LGALKLPFGKTTVMHLVARE,
and (SEQ ID NO: 64)
RFLHGNVTLGALKLPFGKTL.

Particular 15-mers include:
                                      (SEQ ID NO: 65)
NVTLGALKLPFGKTT, (SEQ ID NO: 66)
LKLPFGKTTVMHLVA, (SEQ ID NO: 67)
LGALKLPFGKTTVMH, (SEQ ID NO: 68)
GNVTLGALKLPFGKT,
and (SEQ ID NO: 69)
VTLGALKLPFGKTTV.
```

The present disclosure may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

Modified/mutated peptides are also contemplated, such as an MUB lacking the prenylation site, or an MUB with mutated LBL or with mutated Ub core (to change E2 specificity). In addition to higher affinity, the Ub core should render the peptide more soluble and stable. In particular, variants of the MUB/Ubl3/pfam domain Rad60-SLD_2 (PF13881) that contain a Lap Bar Loop are contemplated.

The disclosure contemplates fusing or conjugating a cell penetration domain, a cell permeability peptide, or cell transduction domain. Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length); others are shown in Table 1, below.

TABLE 1

| CPD/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |

TABLE 1-continued

| CPD/CTD PEPTIDES | SEQ ID NO |
|---|---|
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTGKGDPXPD | 31 |
| PPPPPPPPPPPPPP | 32 |
| VRLPPPVRLPPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKLKL | 47 |
| PAWRKAFRWAWRMLKKAA | 48 |

Also as mentioned above, peptides modified for in vivo use by the addition, at the amino- and/or carboxyl-terminal ends, of a blocking agent to facilitate increased half-life of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methyl-benzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example omithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse MUC1 peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., J. Am. Chem. Soc., 122(24): p. 5891-5892 (2000).

D. Design, Variants and Analogs

The present disclosure focuses on peptides comprising the sequence CQC. Having identified this key structure in MUC1 oligomer formation, the inventors also contemplate that variants of the CQC sequence may be employed. For example, certain non-natural amino acids that satisfy the structural constraints of the CQC sequence may be substituted without a loss, and perhaps with an improvement in, biological function. In addition, the present inventors also contemplate that structurally similar compounds may be formulated to mimic the key portions of peptide or polypeptides of the present disclosure. Such compounds, which may be termed peptidomimetics, may be used in the same manner as the peptides of the disclosure and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the disclosure also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913). Other molecular modeling techniques may also be employed in accordance with this disclosure (e.g., Cohen et al., 1990; Navia et al., 1992; the disclosures of which are incorporated herein by reference in their entirety). All these methods produce data that are amenable to computer analysis. Other spectroscopic methods that can also be useful in the method of the disclosure, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the disclosure that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. TREATMENTS

A. Disease States

The peptides of the disclosure have a broad range of applications. Most immediately, they are valuable research reagents for the vigorous ubiquitylation research field since it provides a never-before-available access point for dissecting early events in the Ub reaction cascade.

In addition, given their novel point of Ub pathway regulation, the peptides of the disclosure provide for new pharmacological interventions in disease. Indeed, E1 and 26S proteasome inhibitors (acting at points both before and after HsLBLp1 in the same pathway) have proven effective clinically, but unfortunately have drawbacks. However, LBL peptides are more specific at ubiquitylation inhibition since they target a subset of E2s, and would thus consequently be expected to have fewer side effects. Furthermore, LBL peptides could treat currently unaddressed conditions, be combined with existing therapeutic compounds, or provide a fail-safe against adaptation to current Ub pathway inhibitors. LBL peptide interaction with E2 provides an assay that could be used to develop even more effective compounds against the mechanism. Interestingly, the LBL peptide mode of action is highly conserved and operates efficiently on plant E2's suggesting such peptides would also be valuable agricultural reagents.

Cancers are a major class of ubiquitin-implicated disease. In particular, cervical cancer is a classic example. Here, one major cause is human papilloma virus, which encodes effector proteins (E6 and E7) that disable host cell cycle control. The loss of control occurs through the inability of Rb and p53 to be correctly regulated by ubiquitylation. Therefore, it is exciting that HsMUB gene expression is a top indicator of cervical cancer recurrence and patient survival. It is plausible that HsMUBs regulate key signaling proteins near the plasma membrane via prenylation driven localization and ubiquitylation complex assembly. As prenyl proteins we predict that MUBs will colocalize in the plasma membrane lipid domains with other prenylated proteins including crucial signaling components like the gamma-subunit of heterotrimeric G-proteins, or the proto-oncogene Ras, which is implicated in over half of all cancers. In these scenarios, HsMUB should be used to target and inhibit specific ubiquitylation reactions dependent of the Ube2D E2 family.

A second way that HsMUBs should be utilized to fight cancer is analogous to existing success found with the 26S proteasome inhibitor bortezomib. Rapidly growing cells have a massive requirement for new protein synthesis that can only be supported by ample amino acid building blocks. Bortezomib works by blocking protein turnover in the 26S proteasome thus denying rapidly growing cancer cells a supply of free amino acids and continued growth. Similarly, HsMUB inhibits protein turnover, but by blocking E2 activation and polyubiquitylation of protein substrates in the first place. Without a chain of four ubiquitins, protein substrates can not gain access to the 26S proteasome degradative core, and amino acids can not be released and repurposed. A potential advantage of MUB vs. bortezomib's inhibition of protein degradation is that MUBs selectively inhibit one highly active branch of the Ub system (the part that depends on Ube2D E2s). Thus mass protein recycling could be inhibited in high amino acid demand cancer cells, while non-cancer cells would not be affected in pathways involving all of the other low capacity E2s and the regulatory pathways that depend on them.

Alzheimer's is another major ubiquitylation-implicated disease. Here oxidative damage to both the 26S proteasome (26S P) and Ubiquitin Carboxyl-terminal hydrolases (e.g., UCHL1) lead to the accumulation of polyubiquitylated substrates that contribute to plaques visible in patient brains. Accumulation occurs powerfully because both the 26S P and UCHLs function to break down chains of ubiquitin. In contrast, MUBs suppress ubiquitin chain formation in the first place and should help to decrease polyubiquitylated protein plaque accumulation. MUBs target the major group of high activity E2 enzymes and could be used to dampen their activation, while MUBs do not interact with any of the other more specific E2 families and so their critical functions would not be perturbed. By targeted modulation of the workhorse E2s, MUBs could alleviate ubiquitin chain accumulation, while avoiding side-affects anticipated from more global inhibition of ubiquitin chain assembly.

B. Formulations and Routes of Administration

In accordance with the present disclosure, patients may be treated with the compounds described herein. It will be necessary to prepare pharmaceutical compositions in a form appropriate for administration to a subject. The compositions will generally be prepared essentially free of pyrogens, as well as other impurities that could be harmful to humans or animals. One will generally desire to employ appropriate salts and buffers to render stable cells suitable for introduction into a patient. Aqueous compositions of the present disclosure comprise an effective amount of stable cells dispersed in a pharmaceutically acceptable carrier or aqueous medium, and preferably encapsulated.

The phrase "pharmaceutically or pharmacologically acceptable" refers to compositions that do not produce adverse, allergic, or other untoward reactions when administered to an animal or a human. As used herein, "pharmaceutically acceptable carrier" includes any and all solvents, dispersion media, antibacterial and antifungal agents, isotonic and absorption delaying agents and the like. As used herein, this term is particularly intended to include biocompatible implantable devices and encapsulated cell populations. The use of such media and agents for pharmaceutically active substances is well know in the art. Except insofar as any conventional media or agent is incompatible with the compositions of the present disclosure, its use in therapeutic compositions is contemplated. Supplementary active ingredients also can be incorporated into the compositions.

Under ordinary conditions of storage and use, the cell preparations may further contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

The compositions will advantageously be administered orally or by injection, including intravenously, intradermally, intraarterially, intraperitoneally, intracranially, intraarticularly, intraprostaticaly, intrapleurally, intramuscularly, subcutaneously, or by other method or any combination of the forgoing as would be known to one of ordinary skill in the art.

As will be recognized by those in the field, a "therapeutically effective amount" refers to an mount of such that, when provided to a subject in accordance with the disclosed and claimed methods effectsone of the following biological activities: treatment of any disease aspect or symptom, including cancer.

As understood in the art, such therapeutically effective amount will vary with many factors including the age and weight of the patient, the patient's physical condition, the condition to be treated, and other factors. An effective amount of the disclosed compounds will also vary with the particular combination administered. However, typical doses may contain from a lower limit of about 1 µg, 5 µg, 10 µg, 50 µg to 100 µg to an upper limit of about 100 µg, 500 µg, 1 mg, 5 mg, 10 mg, 50 mg or 100 mg of the pharmaceutical compound per day. Also contemplated are other dose ranges such as 0.1 µg to 1 mg of the compound per dose. The doses per day may be delivered in discrete unit doses, provided continuously in a 24 hour period or any portion of that the 24 hours. The number of doses per day may be from 1 to about 4 per day, although it could be more.

Continuous delivery can be in the form of continuous infusions. The terms "QID," "TID," "BID" and "QD" refer to administration 4, 3, 2 and 1 times per day, respectively. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c. may be about 6 µg to about 6 mg per day.

The disclosed compounds may be administered, for example, at a daily dosage of, for example: from about 0.01 mg/kg to about 100 mg/kg; from about 0.01 mg/kg to about 80 mg/kg; from about 0.01 mg/kg to about 70 mg/kg; from about 0.01 mg/kg to about 60 mg/kg; from about 0.01 mg/kg to about 50 mg/kg; from about 0.01 mg/kg to about 40 mg/kg; from about 0.01 mg/kg to about 30 mg/kg; from about 0.01 mg/kg to about 25 mg/kg; from about 0.01 mg/kg to about 20 mg/kg; from about 0.01 mg/kg to about 15 mg/kg; from about 0.01 mg/kg to about 10 mg/kg; from about 0.01 mg/kg to about 5 mg/kg; from about 0.01 mg/kg to about 3 mg/kg; from about 0.01 mg/kg to about 1 mg/kg; from about 0.01 mg/kg to about 0.3 mg/kg from about 100 mg/kg to about 90 mg/kg; from about 100 mg/kg to about 80 mg/kg; from about 100 mg/kg to about 70 mg/kg; from about 100 mg/kg to about 60 mg/kg; from about 100 mg/kg to about 50 mg/kg; from about 100 mg/kg to about 40 mg/kg; from about 85 mg/kg to about 10 mg/kg; from about 75 mg/kg to about 20 mg/kg; from about 65 mg/kg to about 30 mg/kg; from about 55 mg/kg to about 35 mg/kg; or from about 55 mg/kg to about 45 mg/kg. Administration may be by injection of a single dose or in divided doses.

The term "unit dose" refers to a physically discrete unit suitable for use in a subject, each unit containing a predetermined quantity of the composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

B. Combination Therapy

In another embodiment, the inhibitors of the present disclosure may be used in combination with other agents to improve or enhance the therapeutic effect of either. This process may involve administering both agents to the patient at the same time, either as a single composition or pharmacological formulation that includes both agents, or by administering two distinct compositions or formulations, wherein one composition includes an inhibitor of the present disclosure and the other includes the second agent(s).

The therapy of the present disclosure also may precede or follow the second agent treatment by intervals ranging from minutes to weeks. In embodiments where the other agent and the inhibitor of the present disclosure are administered separately, one may prefer that a significant period of time did not expire between the time of each delivery, such that the agent and present inhibitor would still be able to exert an advantageously combined effect. In such instances, it is contemplated that one may administer both modalities within about 12-24 hours of each other and, more preferably, within about 6-12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In other embodiments, it may be desirable to alternate the compositions so that the subject is not tolerized.

Various additional combinations may be employed, wherein the compound/agonists of the present disclosure is "A" and the secondary agent is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

It is expected that the treatment cycles would be repeated as necessary. In particular embodiments, the secondary therapy is a cancer therapy, such as those discussed below.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylomithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-pi 85 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurance of the tumor. Additionally, the compounds of the present disclosure can also be used in a neoadjuvant setting.

V. EXAMPLES

The following examples are included to demonstrate preferred embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Cloning and Mutagenesis.

The coding regions of AtMUB3 and HsMUB were PCR-cloned to remove stop codons, enable pET28b ligation, and append C-terminal 6×HIS tags. C-terminal 6×His plus FLAG tagged AtMUB3 were generated by DNA 2.0. Generation of N-terminal 6×HIS AtMUB3, GST AtUBC8 and AtUBC8S22R was as described (Dowil et al., 2011). AtUBC8C85S and all AtMUB3 mutants were generated by bridging-PCR and PCRcloned into pET28b. PCR-cloning of AtUBCs 4, 8, 10, 28, and 36 with intact stop codons; and AtUBC8, AtUBC8S22R, and Ube2D3 lacking stop codons were moved into pENTR-DTOPO for subsequent LR cloning. AtUBC8, AtUBC8S22R and Ube2D3 were transferred to pOGWA (Busso et al., 2005) to generate C-terminal 6×HIS E2 constructs, while AtUBCs 4, 8, 10, 28, and 36 were transferred to pHGWA (Busso et al., 2005) to generate N-terminal 6×HIS E2 constructs. All constructs were sequence verified and cataloged as glycerol stocks for distribution. Primers for construct assemblies are listed in supplemental materials (Table 2).

Protein Expression and Purification.

All proteins were expressed in Rosetta™ 2 (DE3) pLacI *E. coli* (Novagen). Cultures in LB medium were induced by addition of 0.2 mM isopropyl-β-D-1-thio-galactoside (IPTG) at 16° C. for 16 hours with vigorous shaking. For activity assays, AtMUB3 and UBC preparation cell pellets were sonicated in 50 mM Tris-HCl, pH 7.5, 300 mM NaCl, 10% Glycerol and 10 mM Imidazole. The soluble lysate fraction was purified on TALON® metal affinity resin (Clontech) washed sequentially in sonication buffer plus 20 mM then 40 mM Imidazole, and eluted using 200 mM Imidazole. For crystallization, AtMUB3 cell pellets were sonicated in 25 mM HEPES, pH 7.5, 500 mM NaCl, 10% glycerol, 1 mM TCEP, 0.4 mM CHAPS and 10 mM Imidazole, washed and eluted as above, and then applied to hydroxylapatite resin made in lab according to (Hjerten et al., 1956). Hydroxylapatite flow-through was incubated at 70° C. for 10 min and centrifuged to remove heat labile contaminants. For AtUBC8 crystallography, activity-grade elutions were diluted 10-fold and re-purified using metal affinity.

In Vitro Interaction Studies.

GST-tagged AtUBC8 was induced as described above, and the soluble extract fraction was immobilized on GSH resin (Thermo Scientific) for 20 min, followed by three washes with sonication buffer. Equi-molar His-tagged AtMUB3, AtMUB3 mutants and Ub were incubated separately with AtUBC8 loaded GSH resin for 15 min, washed three times using sonication buffer, and boiled in Laemmli buffer. MUB recovery was determined by immunoblotting and chemiluminescent detection using Fujifilm LAS4000 imaging. For FLAG pull-down assay, His-tagged AtUBC8C85S—O-Ub was generated (Sakata et al., 2010). Flag-tagged AtMUB3 was immobilized on FLAG resin (Thermo Scientific) for 20 min, followed by three washes with sonication buffer. AtUBC8C85S—O-Ub protein or Ub were incubated separately with AtMUB3 loaded FLAG resin for 15 min, washed three times using sonication buffer, and boiled in Laemmli buffer.

Crystallization.

An equi-molar mixture of AtMUB3 and AtUBC8 was gently mixed, concentrated to 12 mg/ml, and exchanged to 25 mM HEPES, pH 7.5, 500 mM NaCl, 1 mM TCEP and 0.1 mM CHAPS using Amicon® Ultra-15 centrifugal filter (Millipore). Crystals grew using hanging drop vapor diffusion at 20° C. when mixing equal volumes of protein complex with a well solution of 2 M ammonium sulfate. Six sided bi-pyramidal crystals with a tall and short apex appeared within one day and grew to full size within four to seven days. Crystals belong to hexagonal space group P6322 with unit cell parameters a=b=135.7-Å, c=202.1-Å. Final data set with resolution of 2.8-Å was collected on a GM/CA-CAT 231D-D beam line at APS, ANL. ScUbc4 (1QCQ) (PubMed: 8268156) and ubiquitin structure (3NOB/A) (PubMed: 20655260) were used for molecular replacement using program Phaser (PMID: 19461840). Model building and refinement were completed using the Refmac and Coot programs (PMID: 21460454, PMID: 15572765). Final model include AtUBC8 amino acids 1-147 in chain A and 1-148 in chain C, and AtMUB3 amino acids 2-94 in chain B and 3-94 in chain D with amino acids 2, 3, 43 of chain B and 3-5, 43, 53, 68 of chain D modeled as alanines due to poor density. Data collection and refinement statistics are shown in Table 1.

E2 Thioester Formation Assays.

E2~Ub thioester formation assays were performed at 25° C. using 0.25 µM E1, 3 µM E2, 12 µM Ub, and 50 mM HEPES, pH 8.0, initiated with addition of 1 mM Mg-ATP. When included, 30 µM AtMUB3 was pre-incubated for 15 min at 25° C. Reactions were terminated by the addition of non-reducing or reducing Laemmli buffer. Protein samples were visualized and analyzed as described, above, and quantified using Fuji Film Multi-Gauge software. Relative inhibition efficiency (RIE) was determined by comparing the inhibition efficiency of AtMUB3 mutants to wild type as follows; RIE=[1–(E2~Ub with AtMUB3 mutant/E2)]/[1–(E2~Ub with WT AtMUB3/E2)].

Lap-Bar Peptide Inhibition Assay.

Lap-Bar custom peptide (Leu-Lys-Leu-Pro-Phe-Gly-Lys-Thr, SEQ ID NO: 1, Sigma-Aldrich and Peptide 2.0 Inc.), three scrambled peptides (Thr-Leu-Gly-Phe-Lys-Leu-Lys-Pro, SEQ ID NO: 4, Gly-Leu-Thr-Leu-Lys-Pro-Lys-Phe, SEQ ID NO: 49, Thr-Leu-Phe-Lys-Leu-Lys-Gly-Pro, SEQ ID NO: 50, Peptide 2.0 Inc.) and amino acid controls were dissolved in 50 mM Tris-HCl, pH 7.5, 300 mM NaCl, and 10% Glycerol. To test inhibition of E2Ub formation, 3 µM AtUBC8 was pre-incubated with 500 µM Lap-Bar peptide, control peptides or an eqimolar amino acid mix (1 mM Leu, 1 mM Lys, and 0.5 mM Pro, Phe, Gly and Thr), and analyzed as described above for E2<Ub formation assays.

E2~Ub Thioester Discharge Assay.

AtUBC8 (3 µM) was charged by incubating with 0.25 µM E1, 50 mM HEPES, pH 8.0, 1 mM Mg-ATP and 12 µM K0Ub for 3 min. The E1 was inactivated for 90 seconds with 50×E1 stop buffer (BostonBiochem). Lysine (100 mM) was added to the reaction with or without 30 µM MUB to initiate Ub leaving from the E2 active site.

HTRF-FRET E2 Activation Assays.

HTRF-FRET E2 activation assays were conducted using reagents adapted from the E1/E2 Lite kit (LifeSensors, Malvern, Pa.). Briefly, assays contained 1 nM E1 (HsUBE1), 10 µM Mg-ATP, 50 nM Ub-fluorescein, 0.9 nM Streptavidin-terbium, and 5 nM biotinylated E2 (Ube2D3) in 50 mM Tris-HCl, pH7.5, 5 mM $MgCl_2$, 0.05% CHAPS reaction buffer. HsMUB was exchanged into reaction buffer, and combined with E2 at the indicated concentrations for a 15 minute pre-incubation in a 30 µl volume. Addition of 15 µl E1 started the reactions, while controls lacking ATP established the baseline. Assays were read kinetically using a BioTek Synergy 4 plate reader equipped with Excitation 340/30 nm, Emission1 495/10 nm, Emission2 520/25 nm bandpass filters, a 400 nm dichroic mirror, and a Xenon flash lamp set to read Terbium and Fluorescein emission with a 100 µs time delay and 200 µs data collection time. The corrected FRET ratio was calculated as described in the TR-FRET manual (Molecular Devices): [(Em520/Em490)–(P*Em490))/Em490]*10000, where P=Em520/Em490 with terbium only, a proportionality factor to correct for terbium donor contribution to acceptor emission. The linear slope of the first 10 minutes of the reaction was determined as the initial velocity. The resulting velocity vs. HsMUB concentration data was fit to a standard one-site binding model and Hill equation in Origin 8 curve-fitting software to obtain nearly identical $IC_{50}$ values, which in this case are equivalent to $K_i$ due to conditions of limiting E2 substrate ($[S]<<K_m$).

Example 2—Results

MUBs Inhibit *Arabidopsis* Group VI E2 Activation.

Figure 1B:
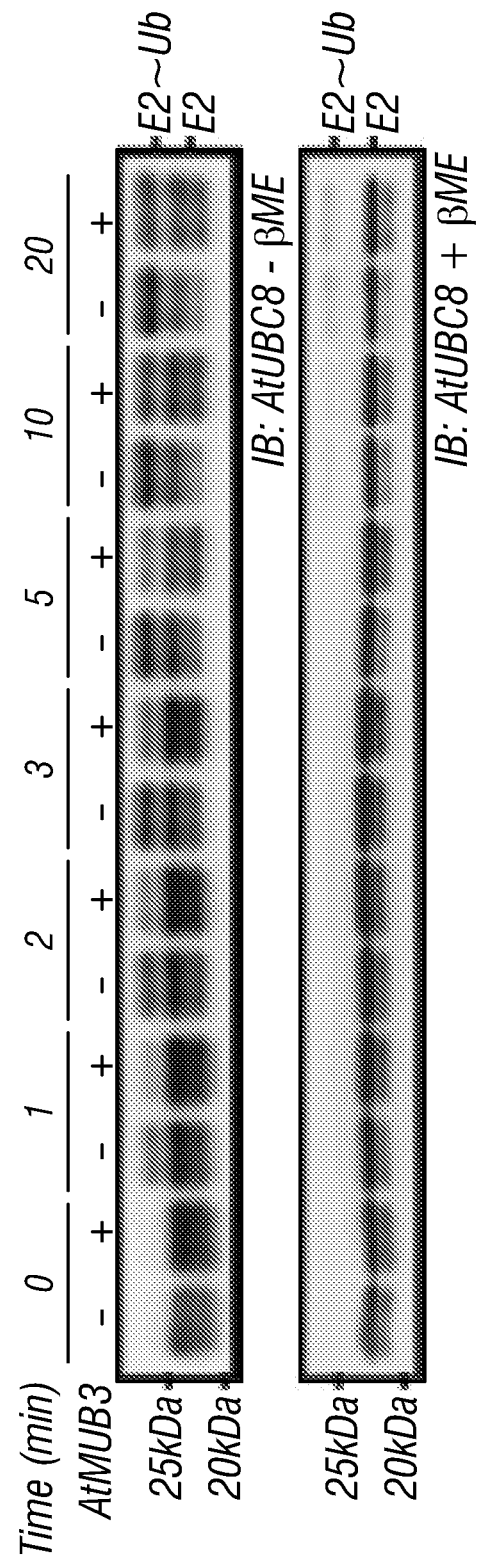
Figure 1C:
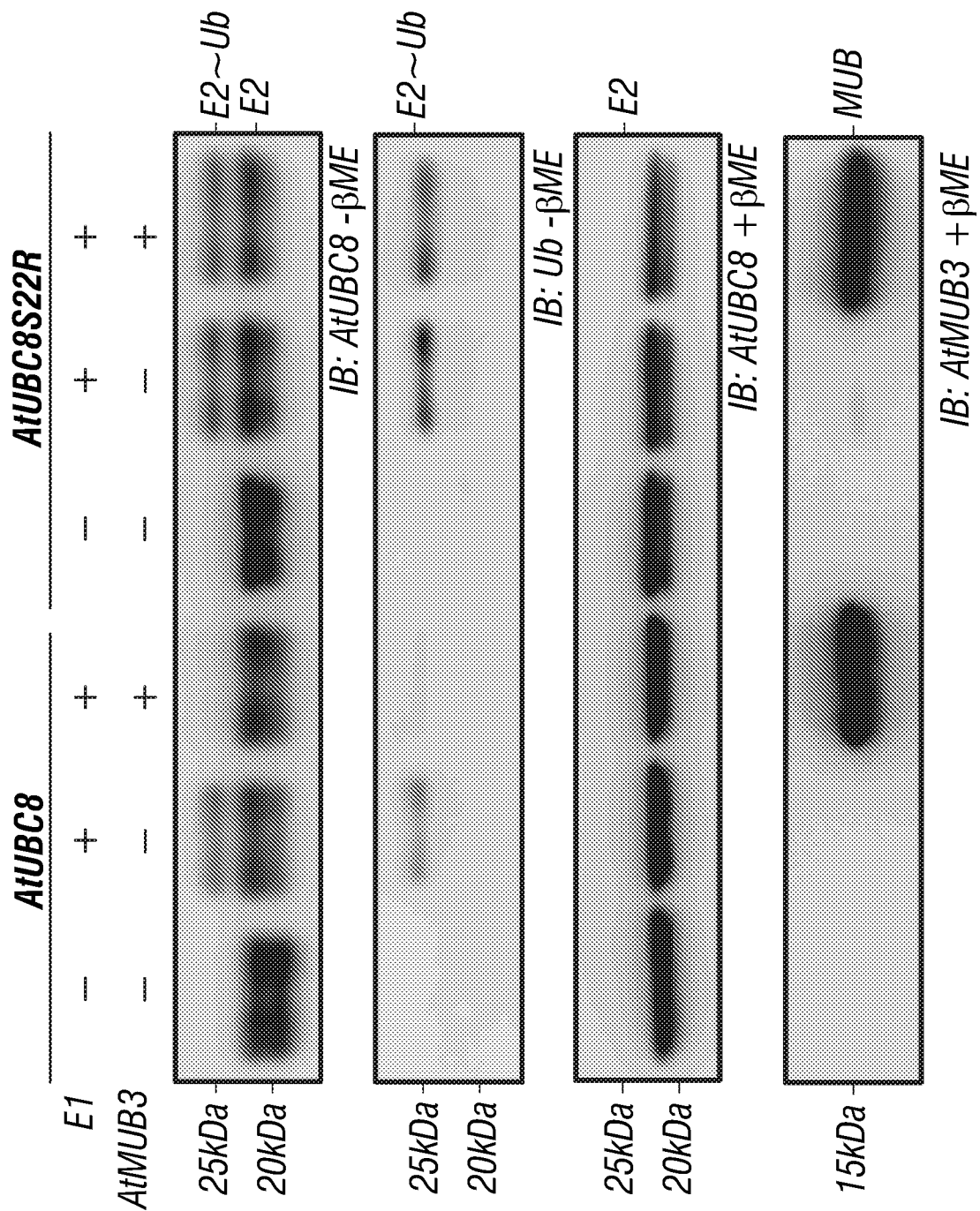
Figure 1D:
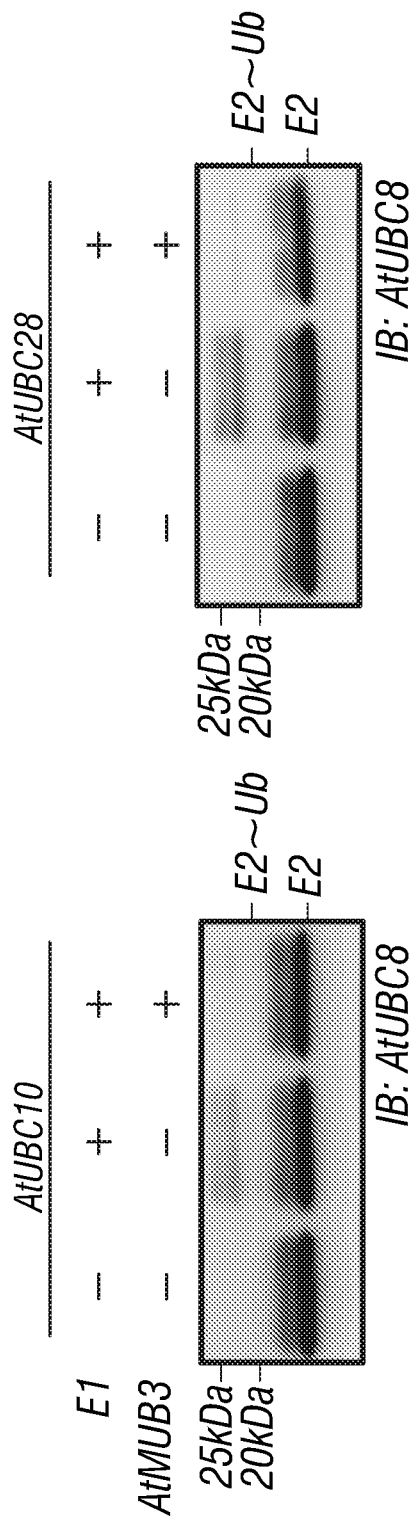
Figure 1D:
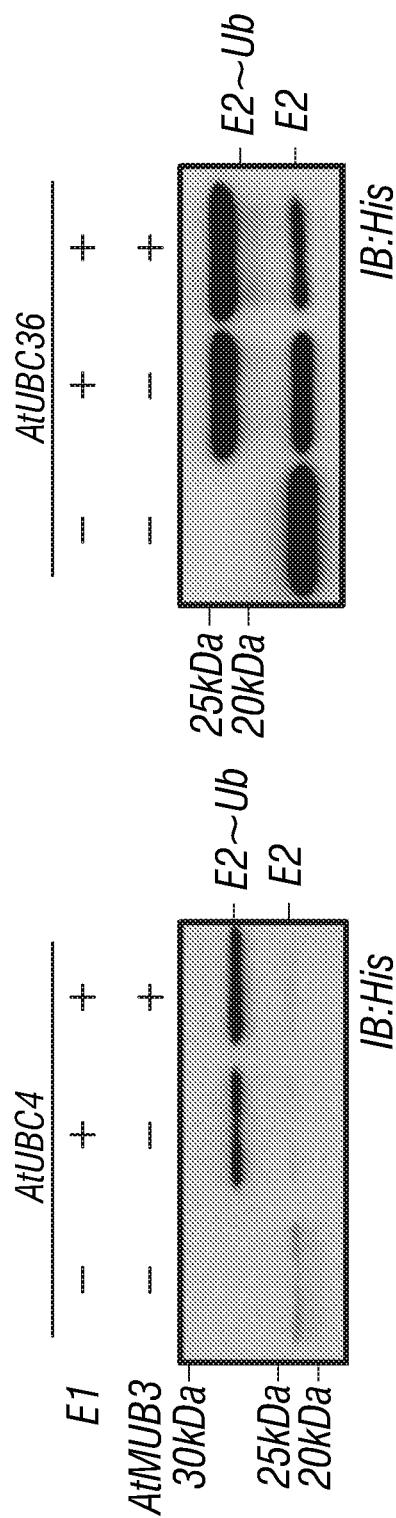

To assess whether MUB binding regulates E2 function, E2~Ub thioester formation assays were performed on AtUBC8. For all time points tested, E2~Ub formation was strongly reduced by AtMUB3 (FIG. 1B). AtUBC8-Ub peptide linkages, which could complicate the analysis, were observed by 10 minutes, so three minute reactions were used in subsequent assays. Ser22 on the so-called backside binding site (BBS) of AtUBC8 is distant from the active site Cys85, and was previously determined to interfere with MUB-induced E2 localization to the PM (Dowil et al., 2011). E2Ub formation on AtUBC8 Ser22Arg was unaffected by AtMUB3, supporting the requirement of a direct interaction for inhibition (FIG. 1C). Since MUBs interact specifically with *Arabidopsis* group VI E2s, two additional subfamily members, AtUBC10 and AtUBC28 were tested. Significantly, AtMUB3 strongly inhibited their activation, however, AtUBC4 from group IV, and AtUBC36 from group XV were unaffected (FIG. 1D). Collectively, MUB discriminates between cognate Ub E2s to inhibit the activation of a specific subfamily.

Sub-Structures of the AtMUB3:AtUBC8 Complex Resemble Free Protein Forms.

Figure 2B:
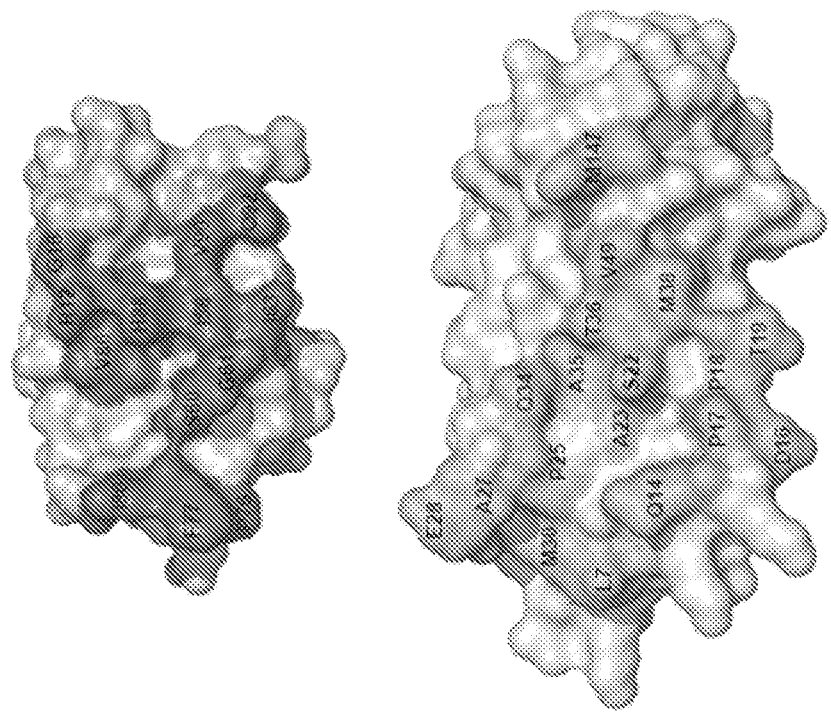
FIGS. 2A-H. An AtMUB3:AtUBC8 co-crystal structure reveals that AtMUB3 interacts extensively with the backside of AtUBC8 and overlaps with noncovalent Ub binding.
Figure 2A:
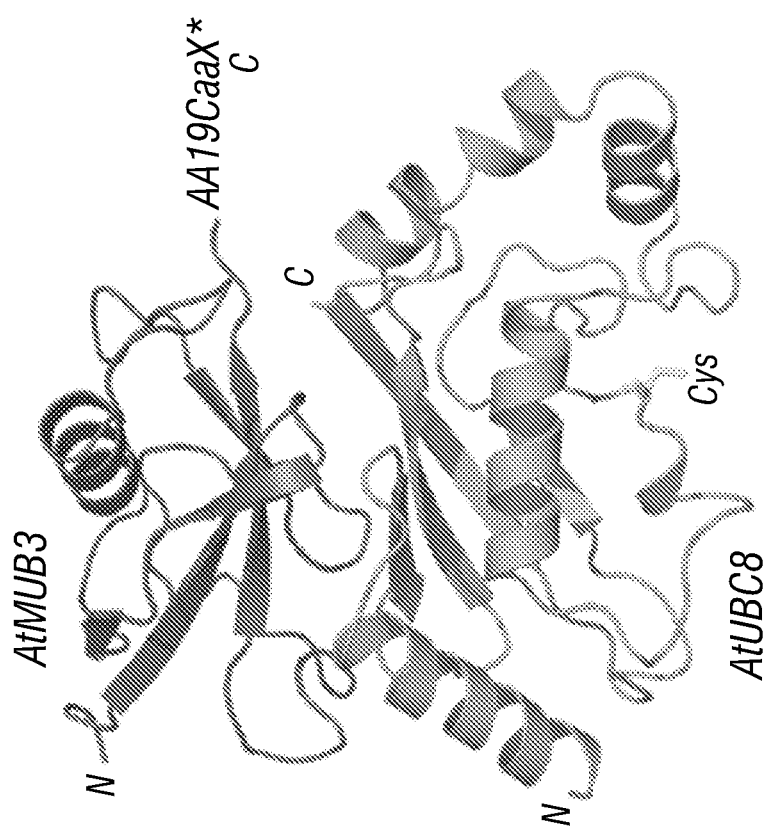
Figure 2C:
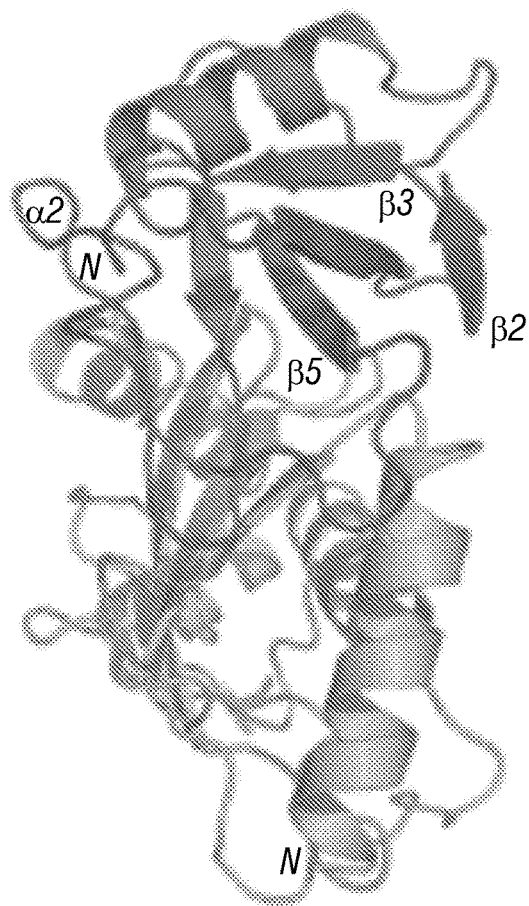
Figure 2D:
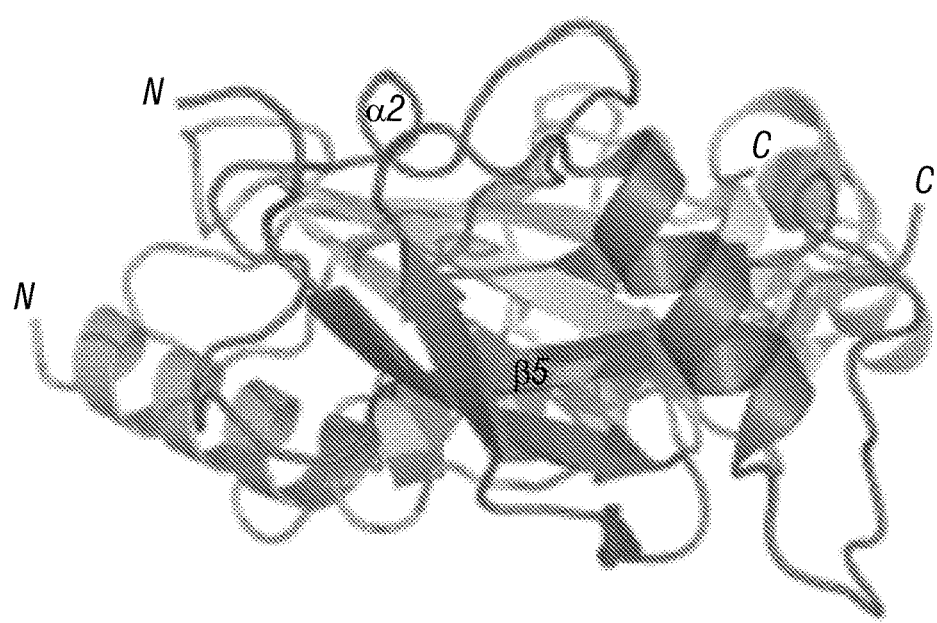
Figures 2E, 2F:
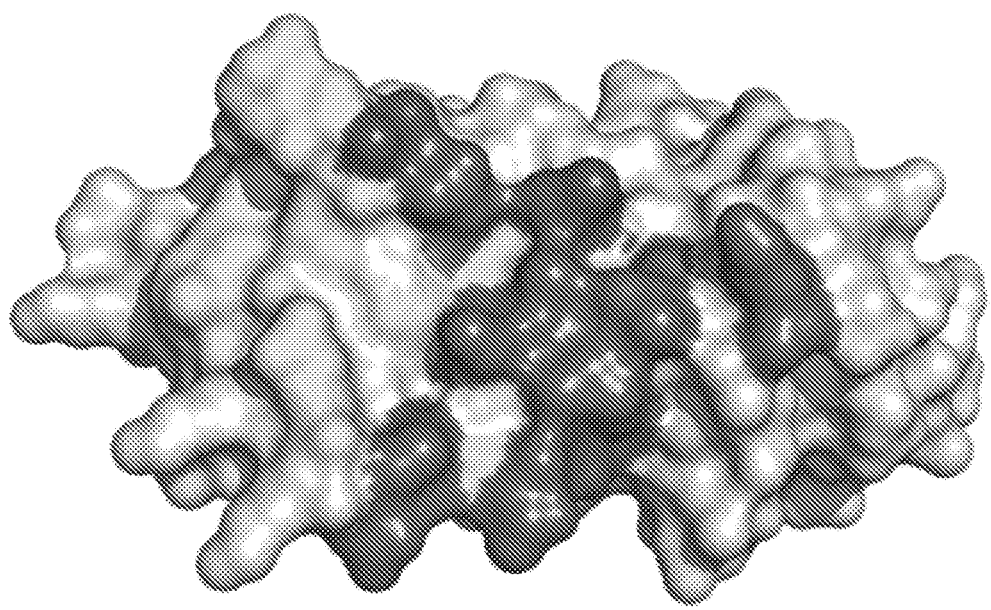

To better understand this initial report of selectivity for cognate Ub E2 activation, we embarked on a mechanistic investigation. The inventors framed two models with different downstream implications. First, that MUBs block the E2 active site, which would imply that a MUB-bound E2 would not participate in substrate ubiquitylation; and second, that MUBs block E1 E2 association, not the active site, supporting the possibility that MUB bound E2s could participate in substrate ubiquitylation when pre-activated. The latter hypothesis proved true, resolved with the aid of a 2.8-Å AtMUB3:AtUBC8 co-crystal structure (Table 1 and FIGS. 2A-2D). AtMUB3 occupies ~900-Å2 of the AtUBC8 surface including the BBS and adjoining N-terminal residues, but does not encroach on the active site Cys85. Indeed, AtMUB3 can pull-down AtUBC8C85S with Ub linked to the active site through an oxyester bond (FIG. 2E). AtUBC8 Ser22 forms a salt bridge with AtMUB3 Gly61, central to the tight interaction surface composed of predominantly hydrophobic interactions and several additional salt bridges (FIGS. 2B and 2H), consistent with previous biochemical studies (FIG. 1B) (Dowil et al., 2011). No structure of an *Arabidopsis* Group VI E2 alone exists, but comparing AtUBC8 to Human Ube2D3 (3UGB) (Page et al., 2012), which is 80% identical and 89% similar at the amino acid sequence level, reveals an r.m.s.d. of 0.7-Å for 146 Cα atoms suggesting that AtUBC8 does not undergo a MUB-induced conformational change (FIGS. 6A-D).

AtMUB3 bears strong resemblance to known Ub-fold structures, featuring a central β-sheet cradling a major α-helix, and a second minor α-helix residing near the Nterminus. Excluding the connecting loops and the unstructured C-terminus, AtMUB3 aligns closely with Ub, r.m.s.d. 1.8-Å for 71 Cα atoms (2FUH) (Brzovic et al., 2006), and SUMO, r.m.s.d. 1.6-Å for 74 Cα atoms (2UYZ) (Knipscheer et al., 2007b). There are no MUB crystal structures for comparison, but AtMUB3 aligns well with an NMR structure of AtMUB1 in solution, r.m.s.d. equivalent 0.8-Å (1SE9) for 66Cα atoms (Vinarov et al., 2004). Notably, some loop positions differ considerably between the AtMUB1 and AtMUB3 structures despite strong sequence conservation of 46% identity and 68% similarity (FIGS. 6A-D). Consistent with efficient MUB prenylation (Downes et al., 2006), the C-terminal nineteen residues of AtMUB3 were unstructured, suggesting a flexible tether to the C-terminal Cys115, which is converted to a C-terminal geranylgeranyl carboxymethyl Cys in planta and used for PM-anchoring. The model that emerges is a MUB-anchored E2 with its active site exposed to cytosolic PM proximal proteins, yet with E2~Ub re-formation biochemically inactivated.

MUB Uses the Ub E2 Backside Binding Site for Interaction.

Figure 2G:
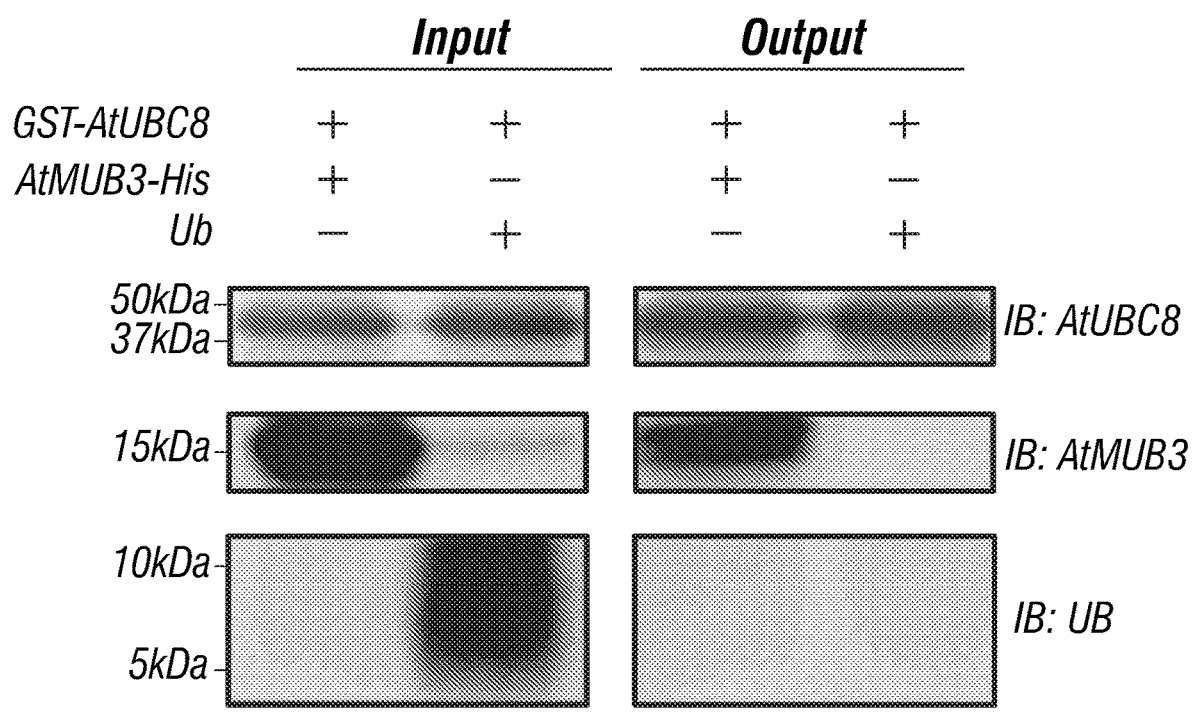
Figure 2H:
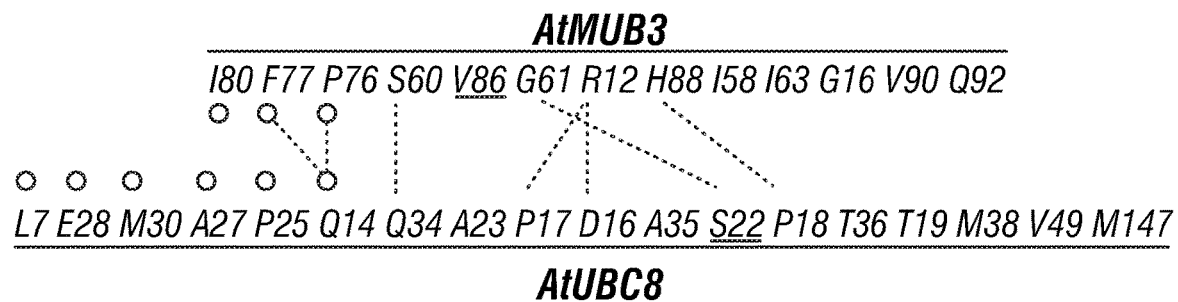
Figure 8A:
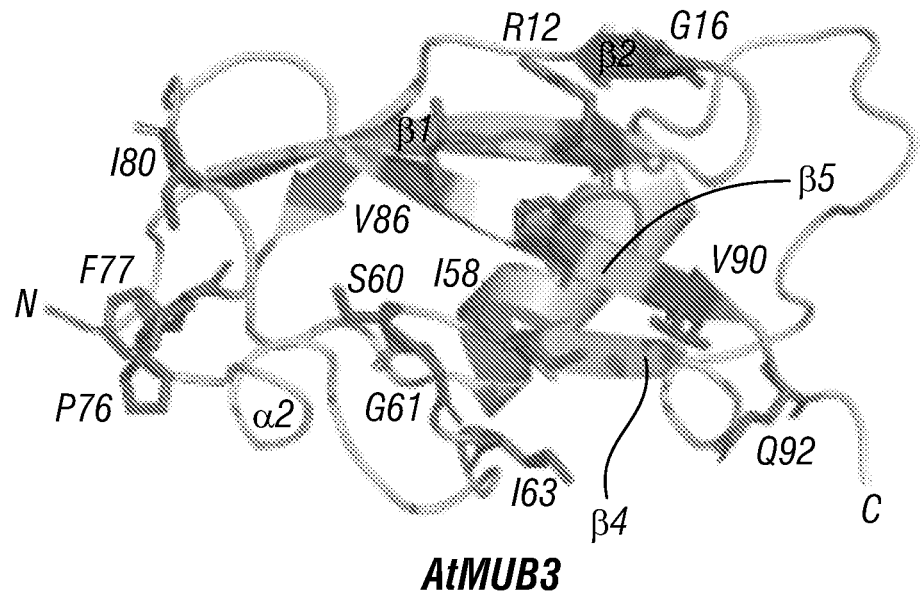
FIGS. 8A-B. AtUBC8 and AtMUB3 interacting residues compared to non-MUBinteracting *Arabidopsis* E2s.
Figure 8A:
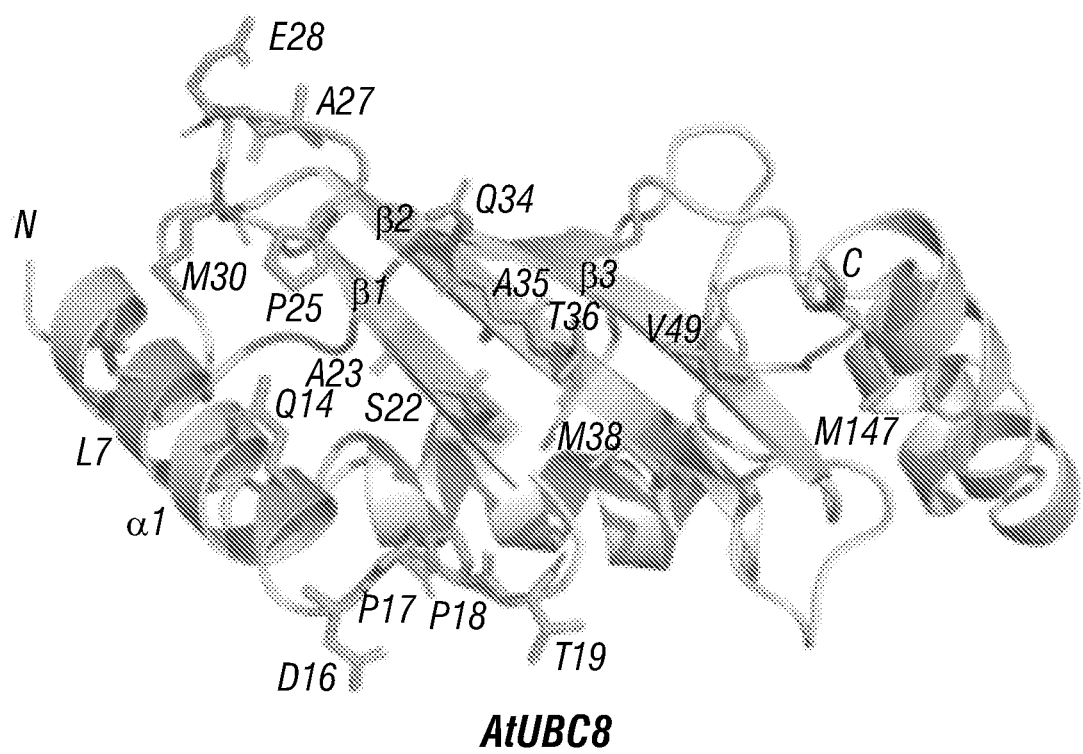
Figure 8B:
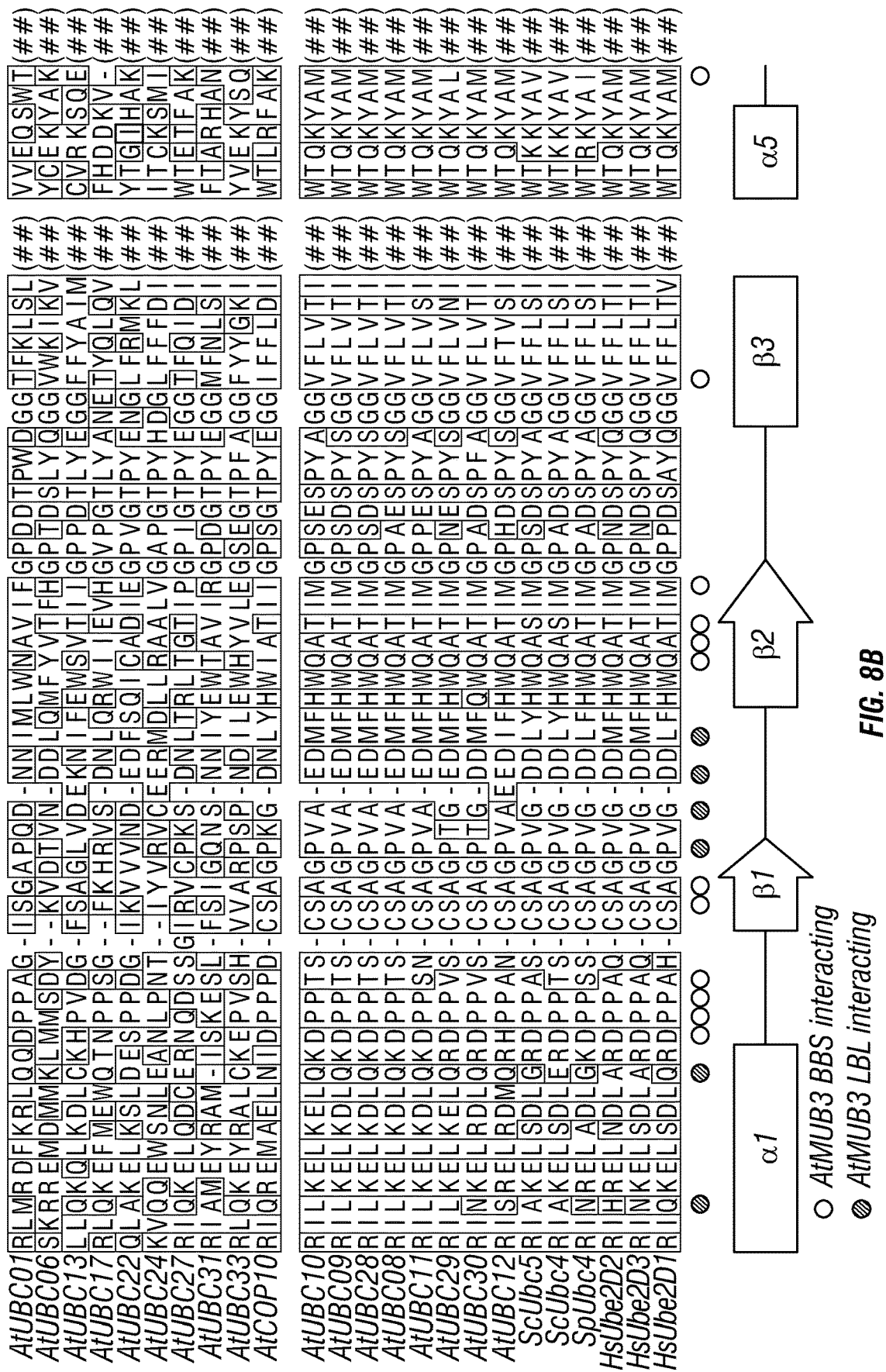
Figure 9A:
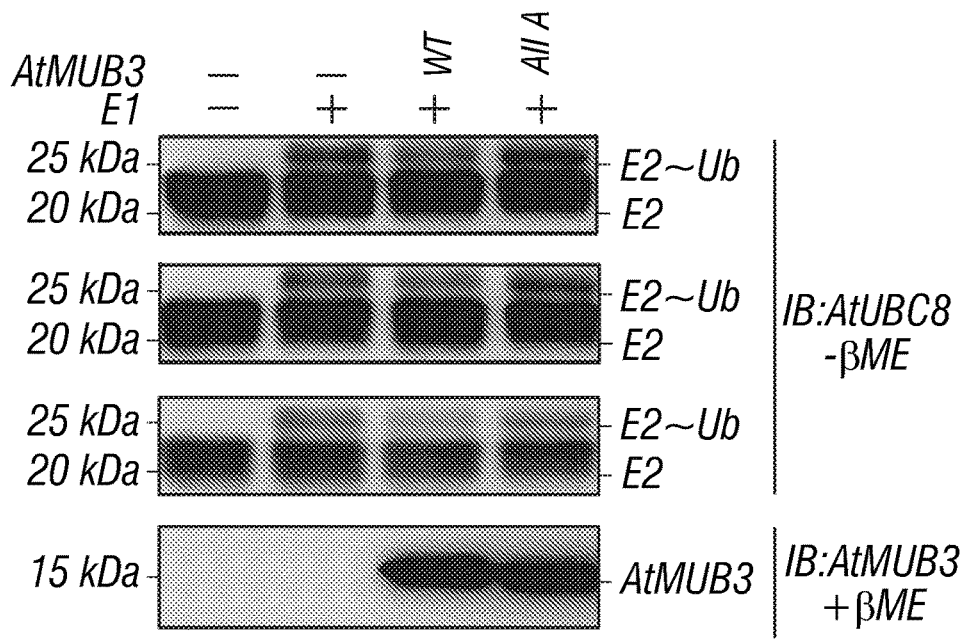
FIGS. 9A-B. MUB3 LBL core residues are critical for inhibiting E2~Ub. AtUBC8~Ub thioester formation assays exposed to (FIG. 9A) AtMUB3 LBL core quintuple mutant (All A) (FIG. 9B) AtMUB3 LBL core single mutants are shown as immunoblot. Experiments were performed in triplicate prior to quantification of band chemiluminescence.
Figure 9B:
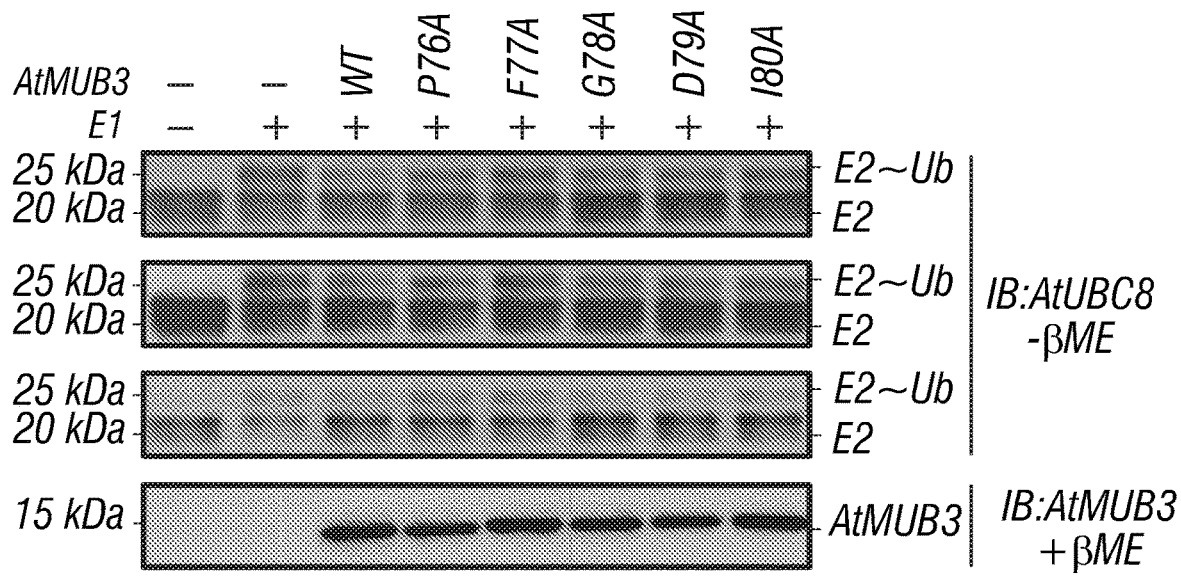

To define a mechanism for AtMUB3 inhibition of E2~Ub formation, the inventors examined known functional E2 surfaces, most obviously, the non-covalent BBS. In detail, the MUB BBS interaction uses the AtUBC8 α1β1 loop (D16, P17, P18, T19), β1 strand (S22, A23), β2 strand (Q34, A35, T36 and M38), β3 strand (V49), and the C-terminal residue M147. Meanwhile, AtUBC8 interacts with AtMUB3 β1, β2, β4, β5 strands (R12, G16, I58, V86, H88 and V90), β4α2 loop (S60, G61 and I63), and one residue on the C-terminal tail (Q92) (FIGS. 2B, 2H and 8). The surface-forming residues are highly conserved in this family of E2s from plants, fungi and humans. These residues are not conserved in other major *Arabidopsis* E2 groups, revealing why MUBs are specific to the Group VI subfamily (FIG. 8).

Figure 7:
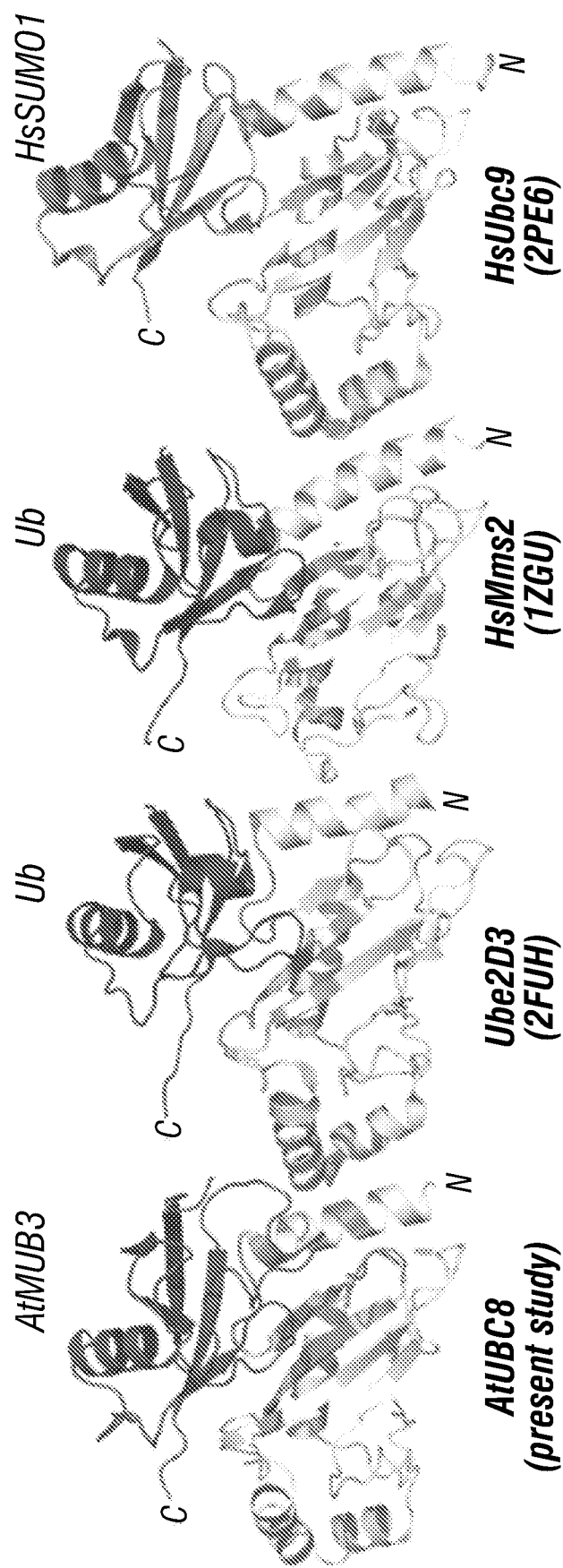
FIG. 7. BBS configuration shared by MUB, Ub and SUMO. Structures of AtMUB3 (magenta), HsUb (red) and HsSUMO1 (orange) bind at the BBS of respective E2s. All E2s are colored in grey with the binding area colored in green.

Comparing AtMUB3:AtUBC8 to the most related structure, Ub:Ube2D3 (2FUH) (Brzovic et al., 2006), reveals that MUB interacts with E2s using a similar configuration (FIG. 7) with several critical differences. MUB and Ub interact with the BBS using nine analogous residues. Each protein also has three unique interaction residues. For Ub, AtUBC8-analogous residues S20, V26, and L51 (FIG. 2F, dark grey) would pull Ub towards the E2 C-terminus, whereas AtMUB3 unique interactions using Pro18, Ala23, and Ala35 tip AtMUB3 towards the AtUBC8 N-terminus (FIG. 2F, green).

The MUB E2-BBS interaction provides a fourth different Ub or Ubl BBS combination implicated in E2 regulation (FIG. 7), which currently includes Ub, SUMO, and Nedd8 (Brzovic et al., 2006; Capili and Lima, 2007b; Knipscheer et al., 2007a; Sakata et al., 2010; Sakata et al., 2007). Thus, MUB likely exerts native regulation of the Ub E2 BBS by occluding Ub access with ramifications for chain building and reaction dynamics. This notion is supported by Rad18, and Ube2D3 S22R suppression of polyubiquitylation (Brzovic and Klevit, 2006; Hibbert et al., 2011). However, such studies of chain assembly are beyond the scope of this study, since it is critical to first understand inhibition of E2~Ub formation by a MUB E2 complex. Collectively, the MUB to E2 BBS surface specifies and anchors the interaction, but has no clear direct role in inhibition of E2~Ub formation, and so the inventors turned their attention to the adjacent interaction surface.

A Unique MUB Structure, the Lap Bar Loop (LBL), Extends Beyond the E2backside Binding Site.

Detailed examination of MUB binding outside of the Ub-analogous BBS reveals a predominant role for the AtMUB3 α2β5 loop (FIGS. 2C-D and FIG. 8), referred to, from here on, as the Lap Bar Loop (LBL). The LBL reaches from the BBS towards the E2 N-terminus to occupy an additional ~290-Å2 surface, highlighted in cyan in FIGS. 2F and 2H. It is likely that the increased area accounts for the significantly stronger interaction that the inventors detect experimentally, relative to E2 and Ub. For instance, the AtUBC8 BBS is an efficient bait for MUB pull-down, but not for Ub pull-down (FIG. 2G). Likewise, the inventors have routinely detected the interaction of MUB and E2 by yeast two-hybrid, but have never detected a Ub E2 interaction (Dowil et al., 2011). In addition, previous reports of both Ub and SUMO BBS interactions have used elegant structural methodologies, but to the inventors' knowledge have not successfully employed pull-downs or yeast two-hybrid to demonstrate interaction (Brzovic and Klevit, 2006; Capili and Lima, 2007b; Knipscheer et al., 2007a; Lewis et al., 2006; Sakata et al., 2010). Further analysis revealed a more negative AG for MUB:E2 compared to other known BBS interactions (Table 1). These results suggest that the LBL enhances the stability of the MUB:E2 interaction that the inventors have observed.

Figure 3C:
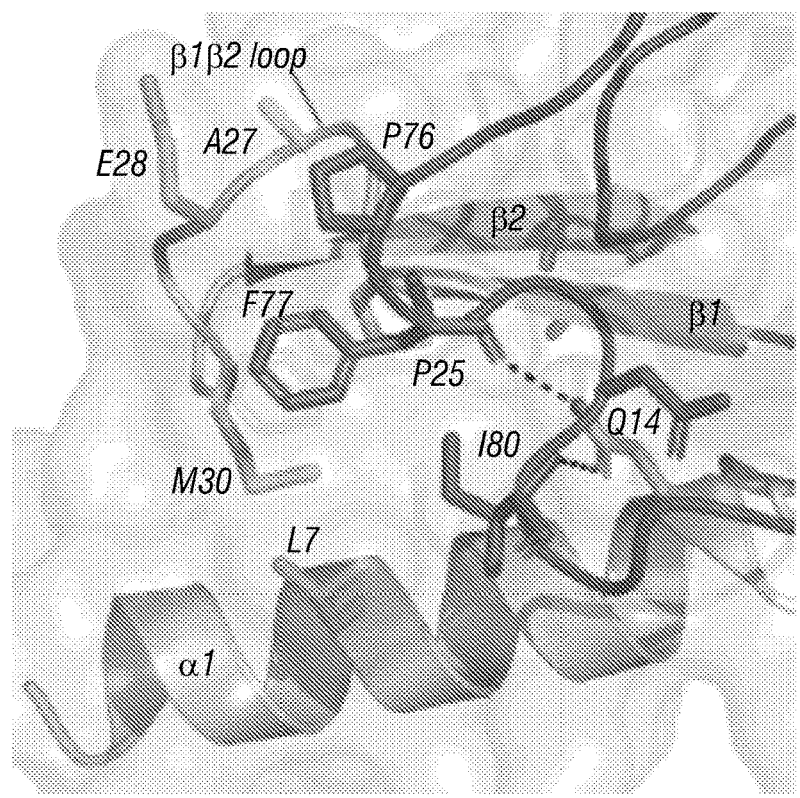
Figure 3D:
Figure 3E:
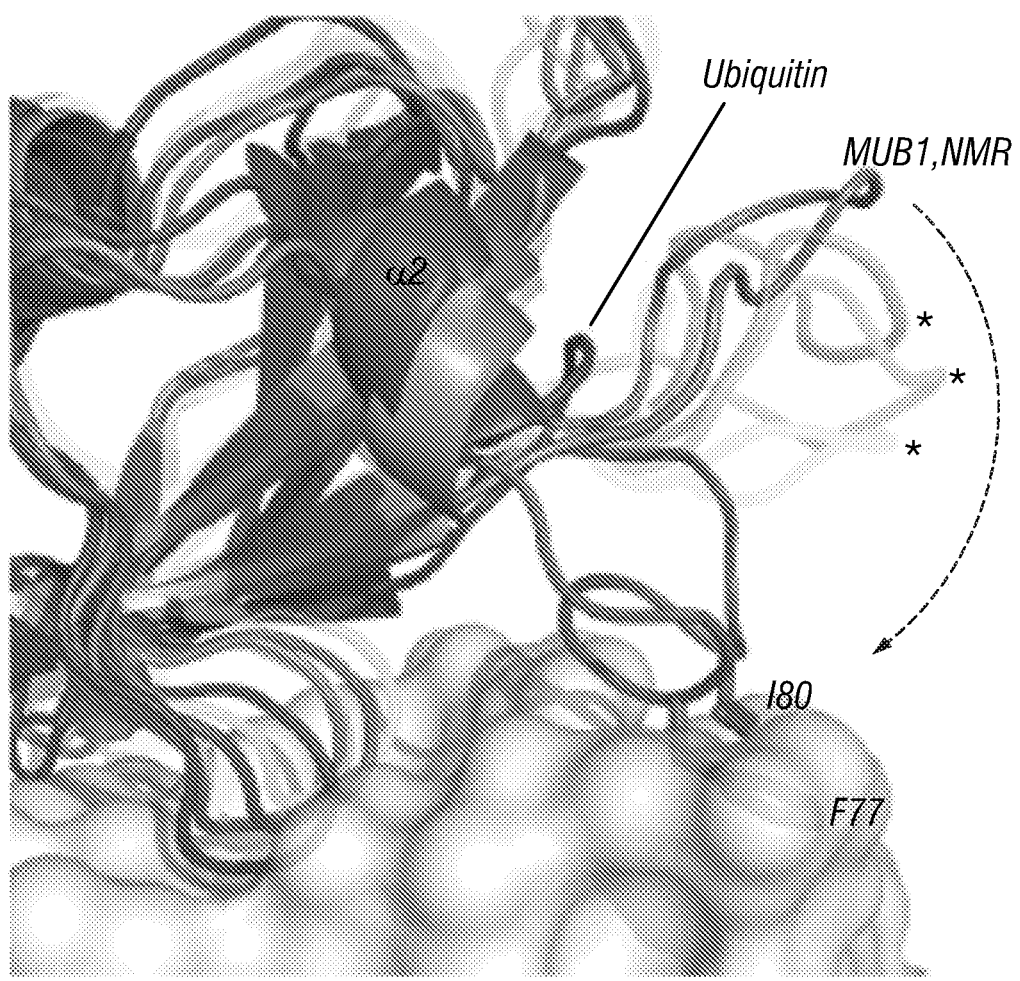

Compared to Ub, the MUB-unique LBL has expanded by 3 and 7 residues in animals and plants, respectively (FIG. 3A). In all cases examined, the LBL contains the consensus (Lys/Arg)xProPheGly([+]/[−]). The larger plant LBL follows with (Ile/Leu/Phe/Val) that contributes hydrophobic contacts and a main chain salt bridge to AtUBC8 (FIGS. 2H and 3A). In all cases, the invariant Pro and highly conserved Phe are the core of the LBL:E2 interaction. Adjacent to the MUB Ub-fold BBS interaction, the LBL loop flattens and conforms to the AtUBC8 surface (FIG. 3B). A detailed view of the interaction reveals how the LBL nestles into a hydrophobic AtUBC8 pocket contacting the 31132 loop residues Pro25, Ala27, Asp28, Met30 on one side and the N-terminal α-helix residue Leu7 on the other (FIG. 3C). Gln14, also on α1, stabilizes the interaction forming salt bridges to the Phe77 and Ile80 main chain positions, possibly contributing to the distinctive sigmoidal shape of the distal "bar" of the LBL. When bound to AtUBC8, the bar is rigid, but flanked by flexible segments indicated by the b-factor values of the structure (FIG. 3D). Superposition with Ub reveals how the extension of the MUB LBL makes contact with the hydrophobic E2 patch (FIG. 3E).

Comparison of free AtMUB1 and the AtMUB3:AtUBC8 complex revealed significant movement of the LBL upon complex formation. In the AtMUB1 NMR structure, LBL adopts flexible conformations in close proximity to the core Ub-fold. In complex, LBL moves away from the core to interact with AtUBC8 al-helix and 31132 loop. This conformational change is significantly larger in amplitude than the movement of this loop in NMR structure. Specifically, the AtMUB3 Phe77 sits in the E2 pocket, however, the corresponding AtMUB1 residue is highly mobile moving over 8.5-Å and never coming within 5.4-Å of the Phe77 position (FIG. 3E). Other local differences may result from torsion of the E2-bound MUB protein. For instance, the short α2 helix that leads into the LBL is less pronounced in the complex than in the free MUB, suggesting that it is flexed upon E2 binding (FIG. 2D, FIGS. 6A-D). At other end of the LBL, the continuous 02 strand of free MUB is interrupted, forming an extended but severely bent 32/133 strand in the complex (FIG. 2C, FIGS. 6A-D). Thus, MUB undergoes conformational change to snap the LBL onto the E2 surface.

MUB Inhibition of E2~Ub Formation is Conserved Between Plants and Humans.

To test whether the differences between plant and animal LBLs influence their activity, the inventors compared them in reciprocal inhibition experiments. The human homologue of MUB, HsMUB, reveals potent inhibition of not just Ube2D3~Ub formation but also AtUBC8~Ub formation, suggesting that the small HsMUB LBL is sufficient. AtMUB3 does not inhibit Ube2D3~Ub, suggesting that the four residue expansion of plant specific LBLs prohibits access to the Ube2D3 surface (FIG. 4A). Taken together, MUB inhibition of E2Ub formation is conserved and broadly relevant to organisms that use the ubiquitylation system.

The LBL Interferes with E2 Charging.

Figure 4B:
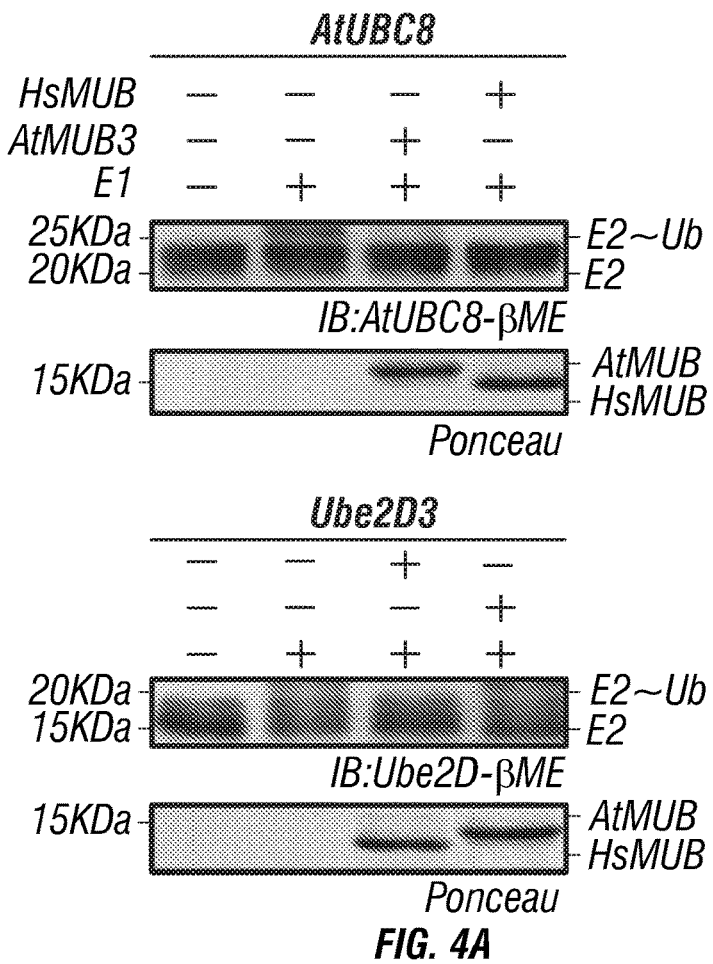
Figure 4B:
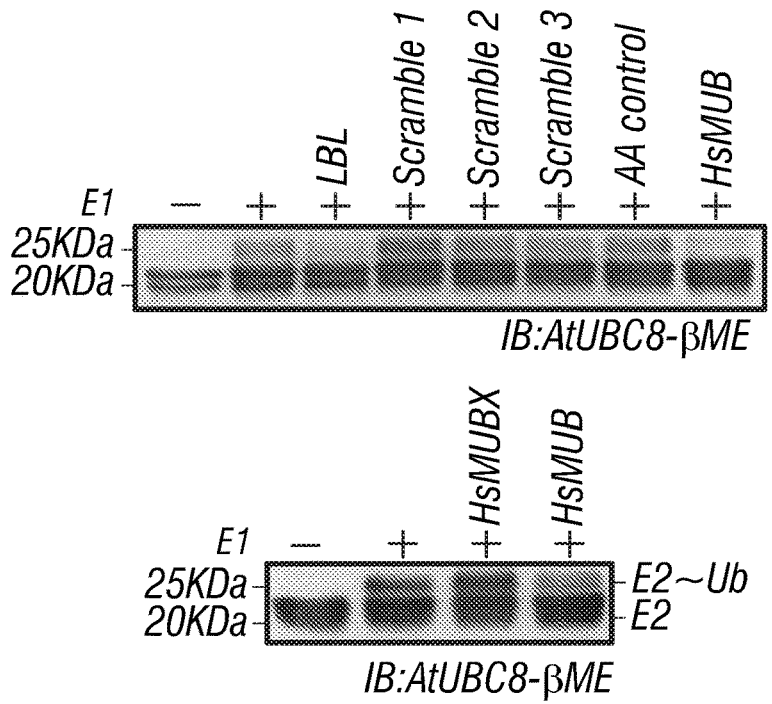
Figure 10:
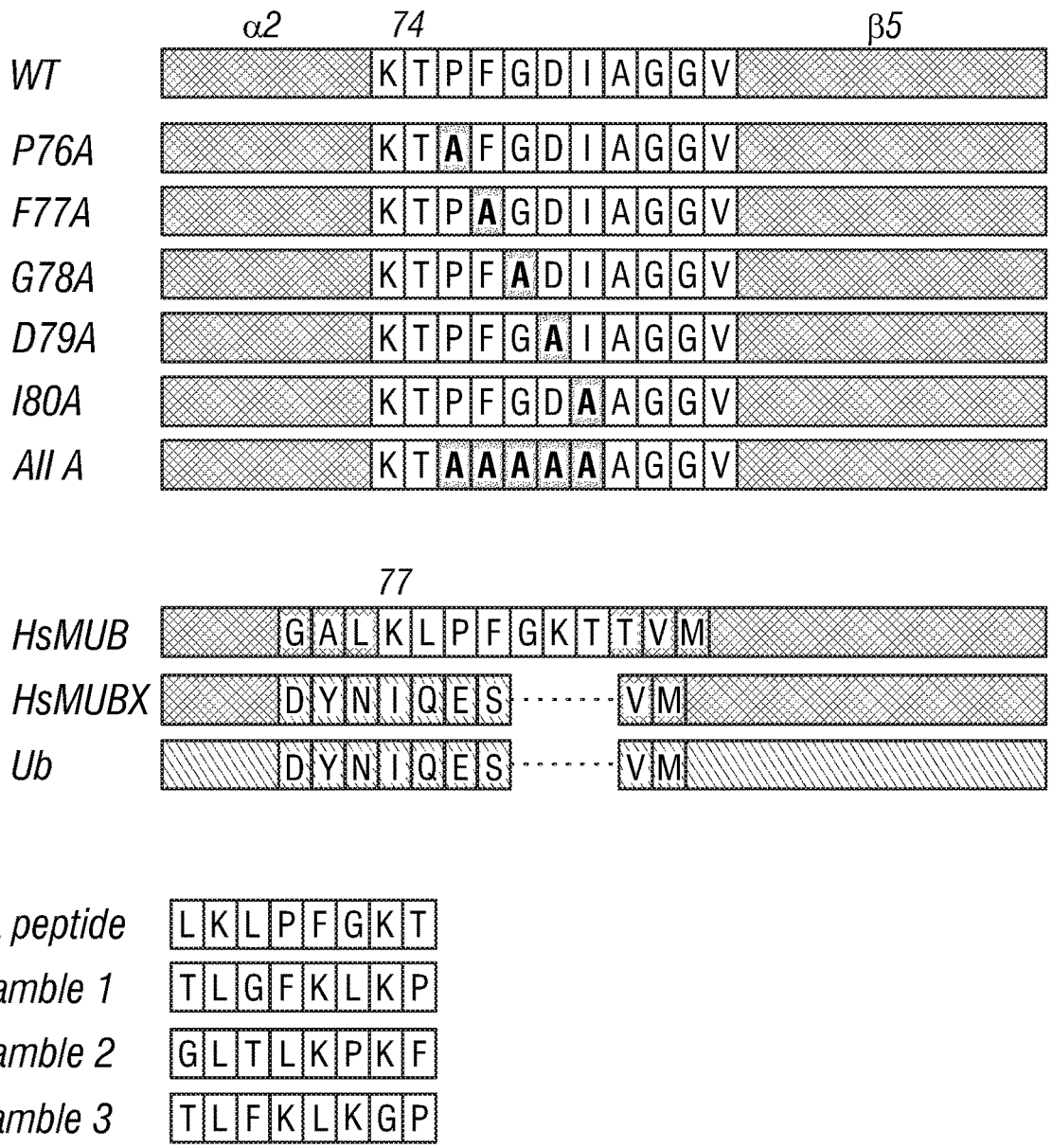
FIG. 10. MUB LBL construct diagram. MUB LBL mutants are shown in bar diagrams with LBL detailed and colored in white. Mutated residues are highlighted in yellow. Top panel is AtMUB3 mutants, middle panel is HsMUB mutants with Ub as reference, and bottom panel is LBL and scramble peptides. WT (SEQ ID NO: 118); P76A (SEQ ID NO: 119); F77A (SEQ ID NO: 120); G78A (SEQ ID NO: 121); D79A (SEQ ID NO: 122); I80A (SEQ ID NO: 123); All A (SEQ ID NO: 124); HsMUB (SEQ ID NO: 125); HsMUBX (SEQ ID NO: 126); Ub (SEQ ID NO: 127); LBL peptide (SEQ ID NO: 128); Scramble 1 (SEQ ID NO: 129); Scramble 2 (SEQ ID NO: 130); Scramble 3 (SEQ ID NO: 131).

To further test the prediction that LBL is sufficient for inhibition, the inventors applied a minimal human LBL (LeuLysLeuProPheGlyLysThr (SEQ ID NO: 1)) peptide to E2~Ub formation assays. This peptide (5 mM) has potent inhibitory activity, similar to HsMUB (30 µM). Three scrambled peptides (5 mM, each), or eqi-molar free amino acids have no effect. In a complementary experiment, HsMUB with the LBL replaced with the Ub α2β5 loop (HsMUBX) completely lost the ability to inhibit E2~Ub formation (FIGS. 4B and 10). Further, AtMUB3 with the core LBL residues ProPheGlyAspIle all converted to alanines failed to inhibit, while retaining binding in pull-down assays. Individual mutations of this sequence revealed that the highly conserved ProPhe motif is most responsible for inhibition (FIGS. 4C-D, 9A-B and 10).

Figure 5A:
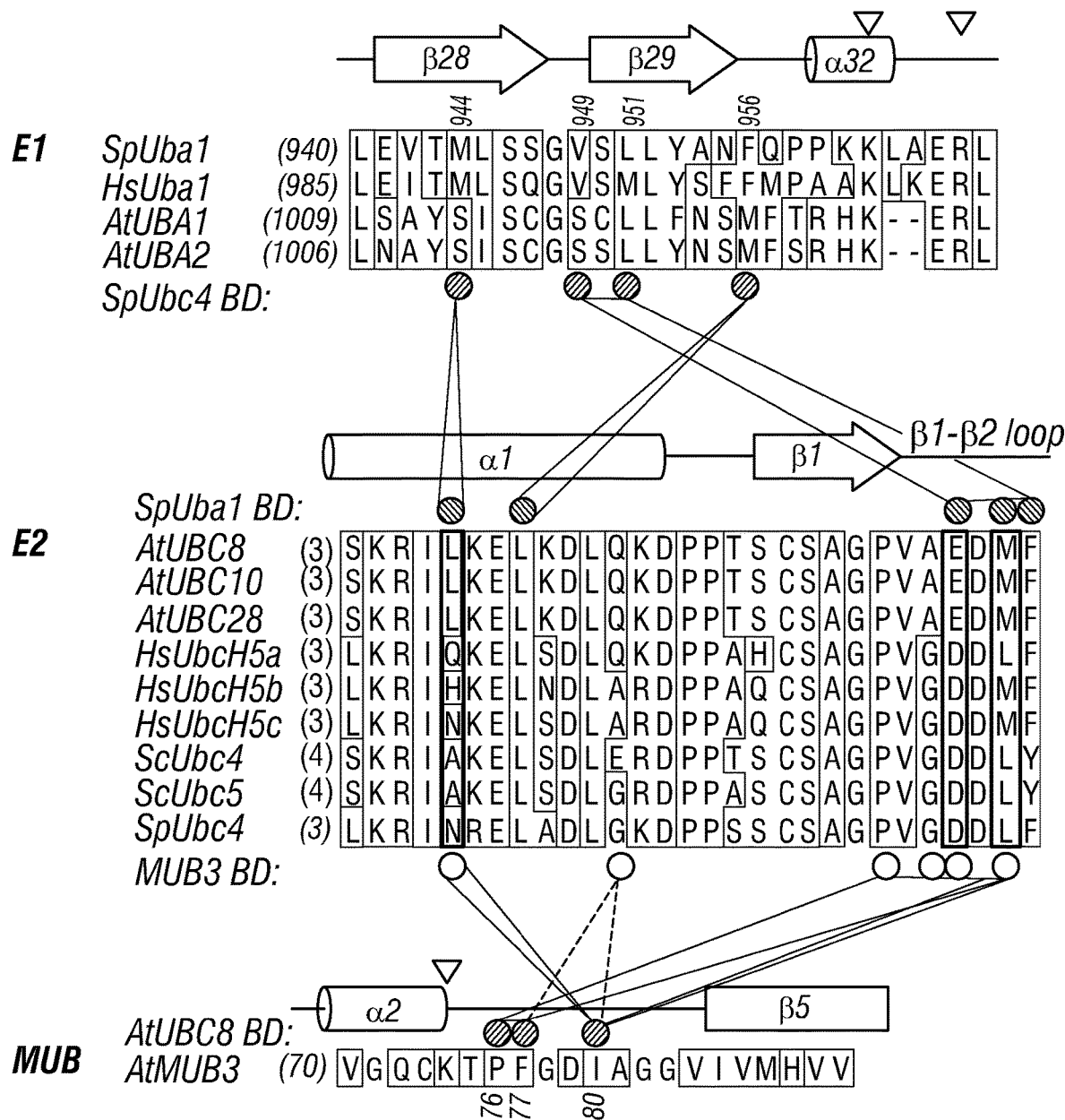
FIGS. 5A-E. The MUB LBL conflicts with E1 E2 association.

The UFD of E1s and the LBL of AtMUB3 require access to the same E2 residues for interaction To better define the mechanism used by the LBL to inhibit E2<Ub thioester formation, the inventors compared the LBL:E2 surface and a previously characterized E1:E2 surface, which revealed that LBL interferes with E1 interaction. The *S. pombe* E1 (SpUba1) uses the conserved UFD domain to coordinate E2(SpUbc4)-Ub formation. The surface uses β28 to α32 helix structures including two key E2 binding residues, Leu951 and Phe956 in *S. pombe*, which are conserved in *Arabidopsis* UBA1/2 as Leu1020 and Met1025 (FIG. 5A, top). Mutation of these SpUba1 residues decrease E2~Ub formation by at least 75% (Olsen and Lima, 2013). Notably, plotted in FIG. 5A, middle, the N-terminal twenty-nine E2 residues of the al helix through the β1β2 loop contain residues for both (i) E2~Ub formation (Olsen and Lima, 2013) and (ii) LBL binding (FIG. 3C). Positions Leu7, Glu28, and Met30 are key contacts for Phe77 and Ile80 of AtMUB3 LBL, and Leu951 and Phe956 of the SpUba1 UFD, respectively (magenta vs. green circles, FIG. 5A). Most of the conflict occurs in two focal regions, the C-terminal half of the al-helix and the 31132 loop, which form a conserved contiguous surface in both AtUBC8 and SpUbc4 structures.

Figure 4C:
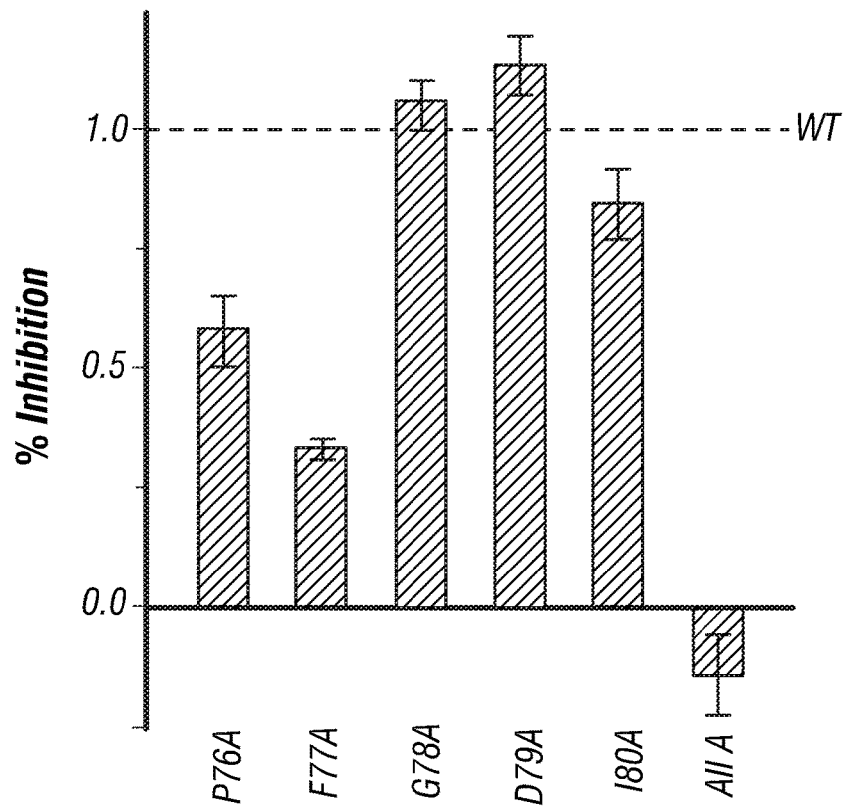
Figure 4D:
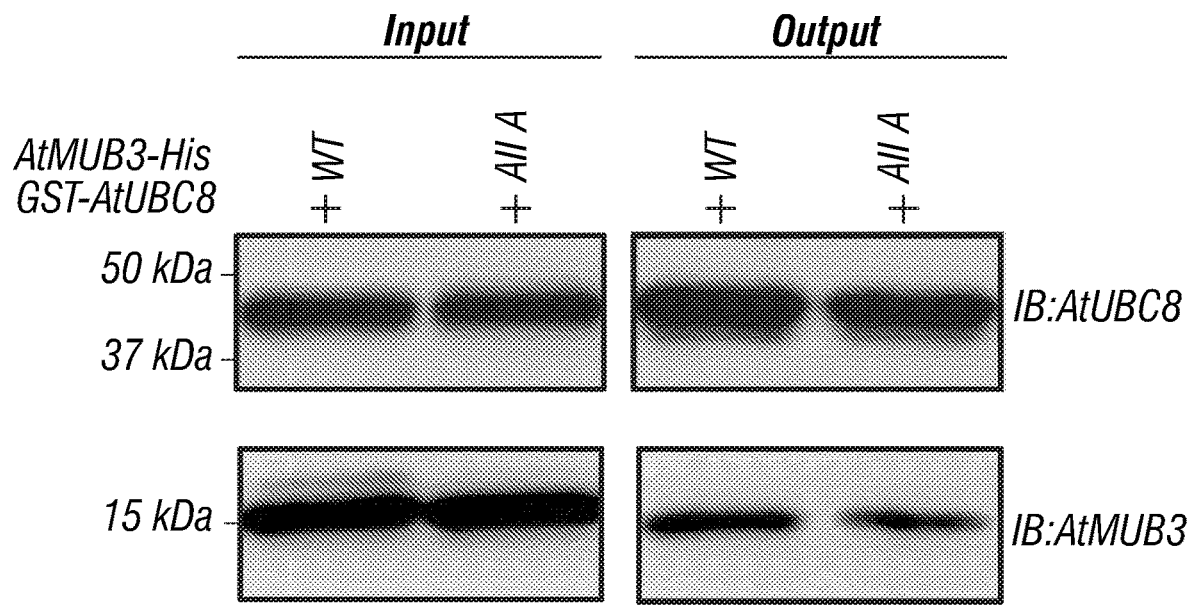
Figure 5B:
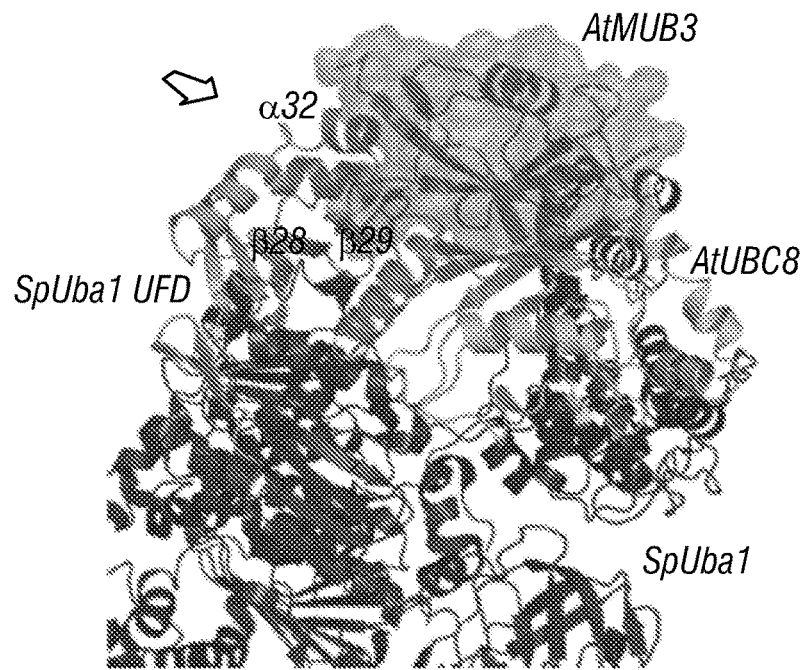
Figure 5C:
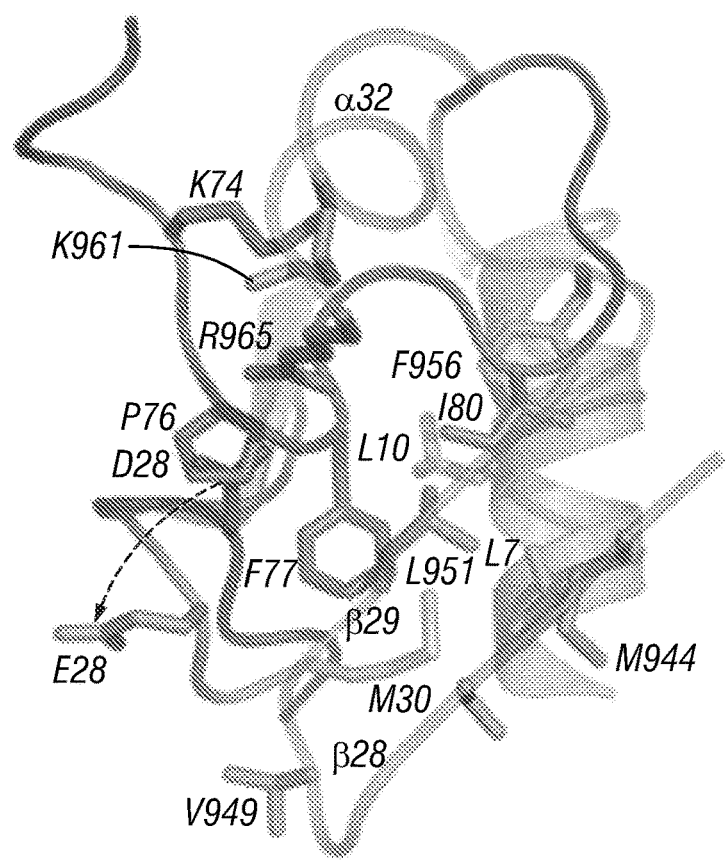

To examine the conflict-implicated residues in three dimensions, a model was generated superimposing the AtMUB3:AtUBC8 complex onto the SpUba1:SpUbc4 structure (FIG. 5B), which revealed that the conflict is exclusive to the UFD of the E1. Here, the Phe77 and Ile80 of the LBL are imposed directly into the hydrophobic groove used by SpUba1 Leu951 and Phe956 (FIG. 5C). The central position of Phe77 in the conflict explains the strong loss of inhibition seen with Phe77Ala (FIG. 4C). Aside from Phe77, Pro76 appears to play a key role positioning these residues in the conflict zone. Further examination reveals a conflict that could not have been predicted without the model. Specifically, MUBs have a conserved Lys/Arg 74 at the entry to the LBL (FIG. 3A) whose side chain comes within 1.1-Å of Uba1 Lys 961 and near Arg965, these basic residues are conserved in all E1s examined (FIGS. 5A and 5C). This conflict occurs at the distal tip of the E1 UFD on α32 (FIG. 5C) and would be repelled with significant leverage by MUBs. In addition, electrostatic interactions between *S. pombe* Ubc4 Asp28 and Uba1 Lys961 and Arg965 (Olsen and Lima, 2013) are disrupted by the LBL ProPhe, which twists the analogous AtUBC8 Glu28 away from these basic residues, displacing the AtUBC8 β1β2 loop (FIG. 5C). Taken together, the E1:MUB:E2 model reveals direct conflicts between the E1 residues required for E2~Ub formation and the MUB LBL residues found to inhibit E2~Ub formation, and in conjunction with the BBS interaction explains why MUBs can specifically inhibit the E2 subfamily.

To the inventors' knowledge, the control of E1 access to a Ub E2 subfamily, reported here for MUB, is unique in the current literature. It is worth noting, however, that unlike plants (Hatfield et al., 1997), vertebrates and sea urchins express a second evolutionarily divergent Ub E1 called Uba6 (Jin et al., 2007) that has inherent specificity for a Ub E2. While Uba1 and Uba6 both activate the Ube2D subfamily, only Uba6 activates the E2 Use1 (Groettrup et al., 2008). Ube1/Uba6 chimeric enzymes revealed that E2 preference resides in the UFD domain (Jin et al., 2007). This is reminiscent of MUB utilization of the UFD binding surface to block E2 activation. However, Ube1 and Uba6 have hard wired UFD E2 specificities, while MUBs conditionally obscure UFD access for E2, dependent on subcellular localization and ability to recognize the BBS. Another difference from Uba6 is that MUBs are more broadly distributed; found in eukaryotes except for a select few Ascomycota including brewer's yeast.

Figure 11:
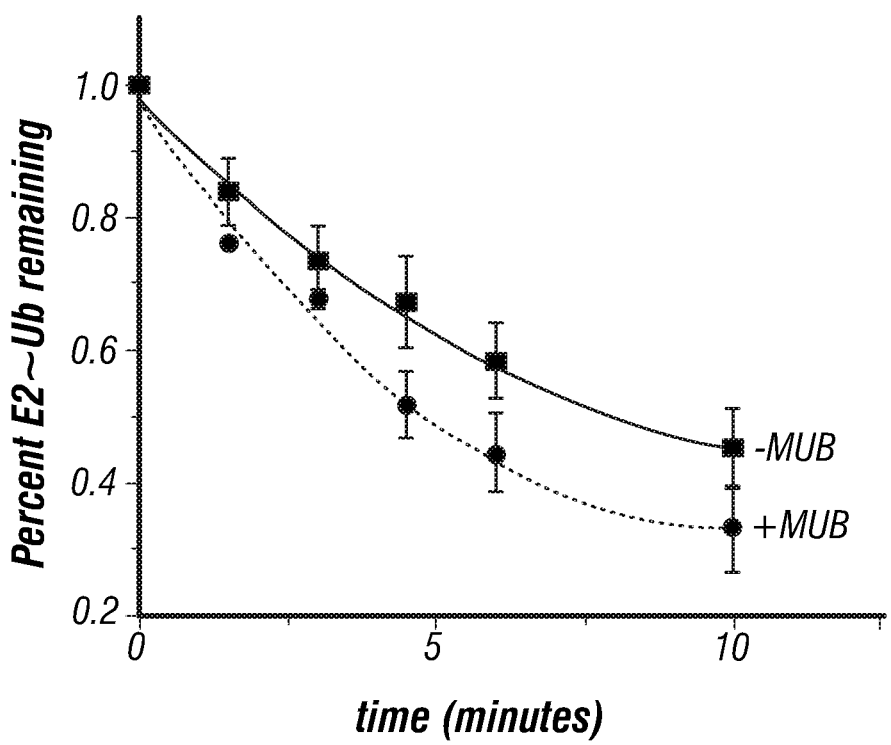
FIG. 11. MUB increase Ub discharging from E2. AtUBC8~Ub discharging assay is exposed to AtMUB3. The quantification is presented in line graph, top panel (+/−SEM and n=3 for all data points), while the immunoblot (IB) of triple parallel experiments is shown in bottom panel.
Figure 11:
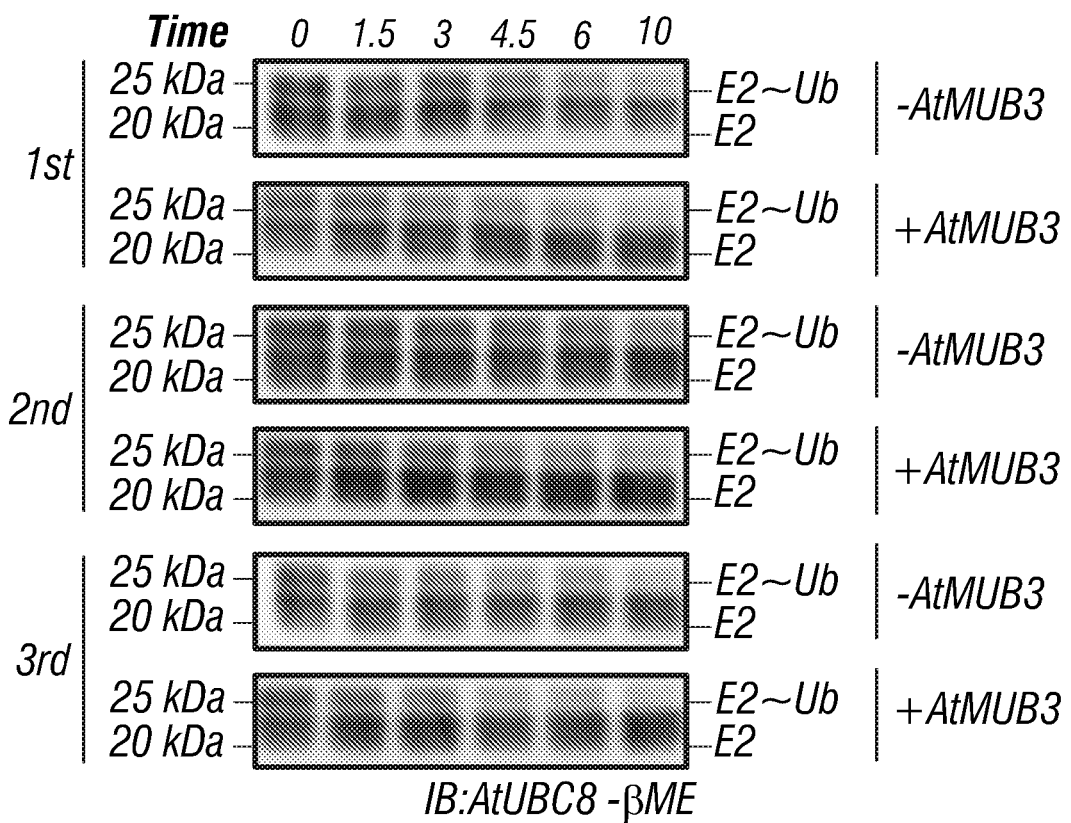

An alternative explanation of these results is that MUB accelerates E2~Ub release rather than inhibiting E2<Ub formation. Indeed, Ub release from MUB-bound E2 does occur slightly faster when exposed to free Lys leaving groups (FIG. 11). However, as opposed to the clear structural evidence for MUB impedance of E1 E2 association, the inventors do not detect a conformational change in the E2 active site at the current resolution. Nonetheless, this complex issue has precedents and clearly warrants further investigation. For example, the G2BR domain of the RING E3 gp78 contacts the BBS of Ube2g2 to effect allosteric changes of the E2 active site (Das et al., 2013; Das et al., 2009), as does interaction with Cue1p (Metzger et al., 2013). Furthermore, mutations of E2 UFD-interacting residues alter E2 conjugation activity even when activation occurs via E1 lacking its UFD domain (Tokgoz et al., 2012).

Figure 5D:
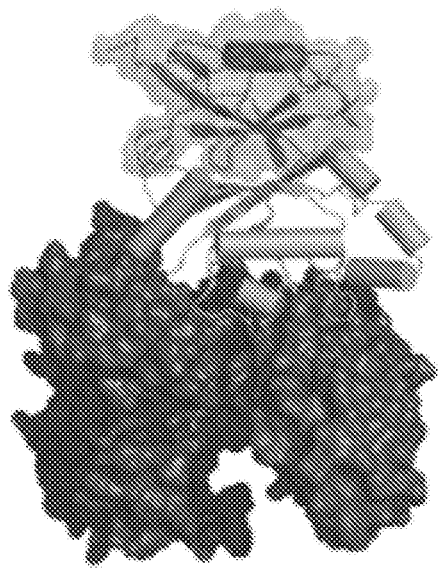
Figure 5D:
Figure 5D:
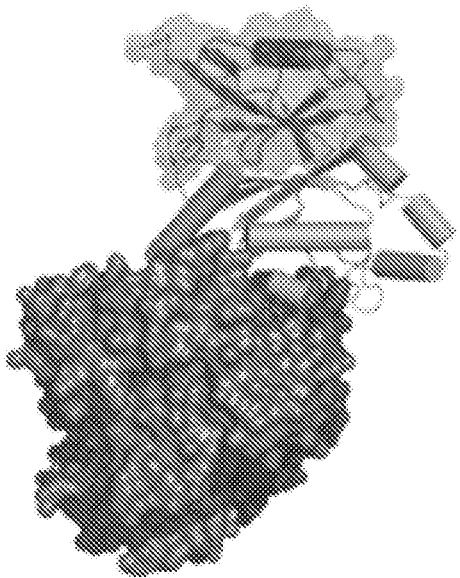
Figure 5D:
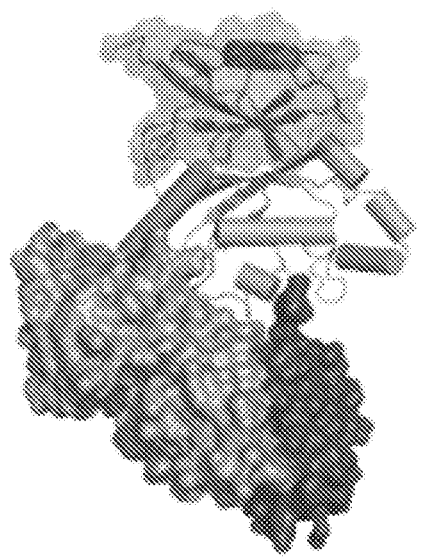
Figure 5E:
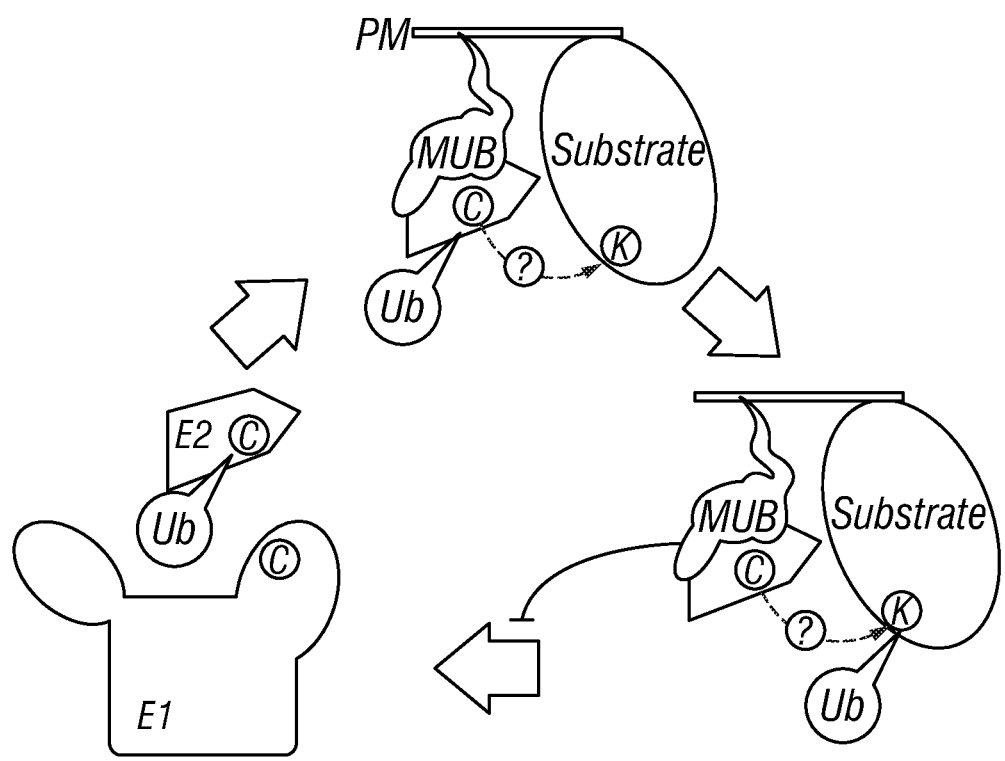
Figure 6A:
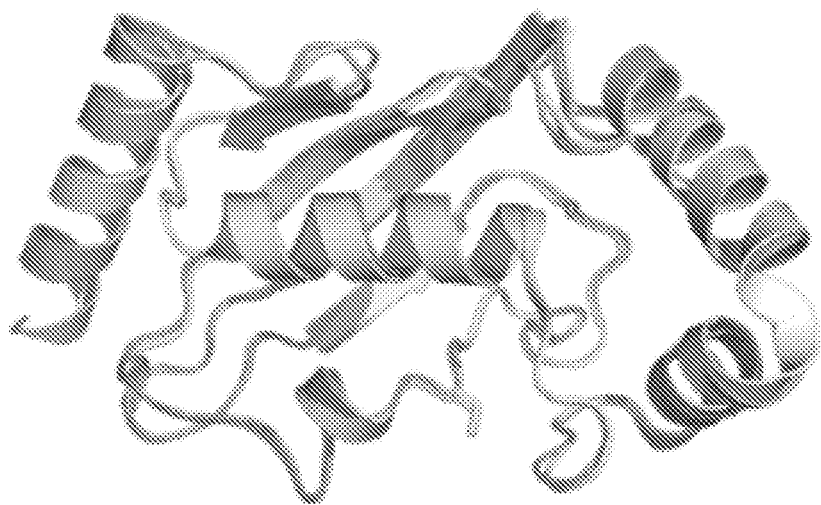
FIGS. 6A-D. S1 Proteins aligned for r.m.s.d determination.
Figure 6B:
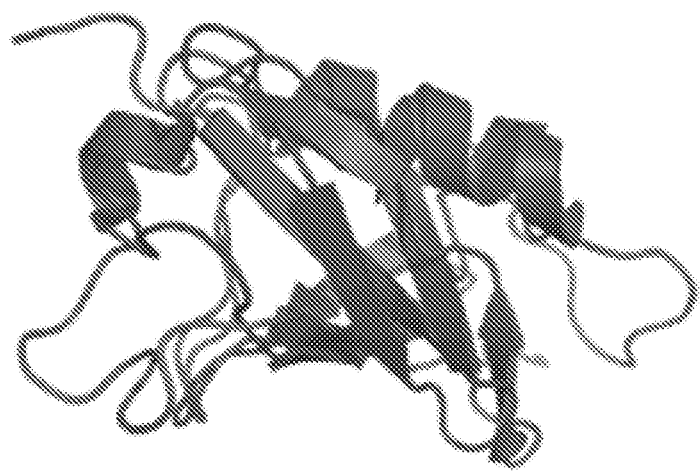
Figure 6C:
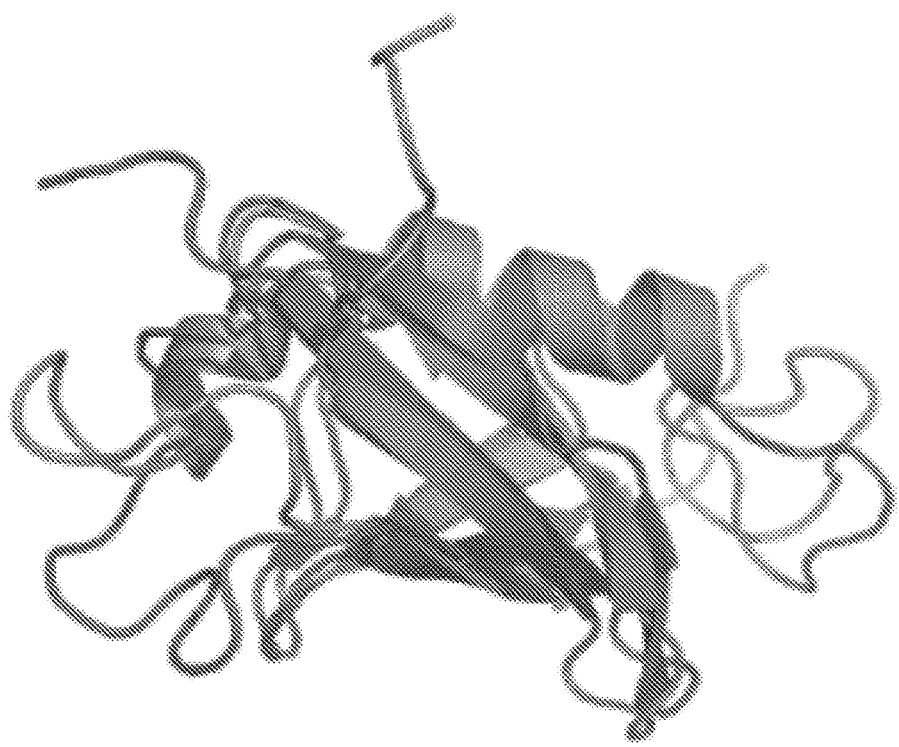
Figure 6D:
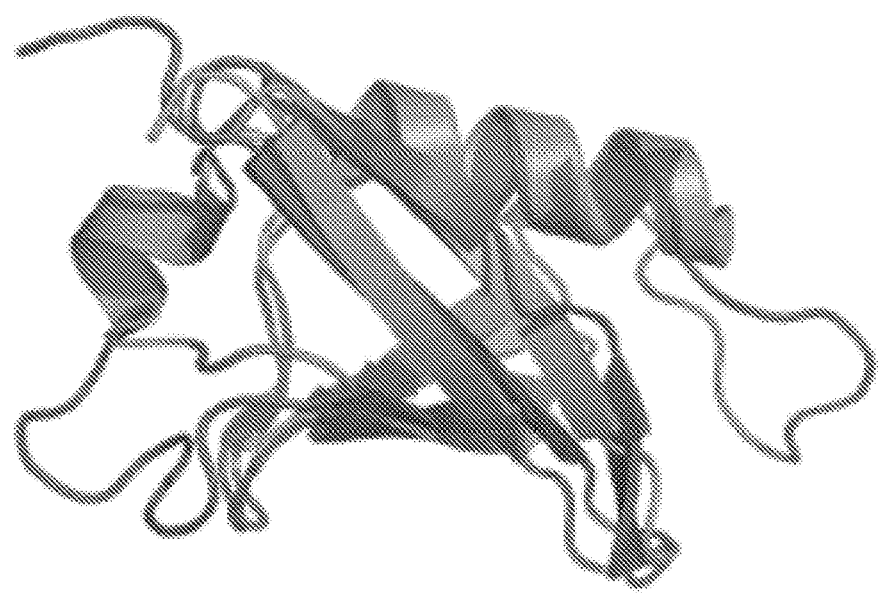

MUB does not sterically interfere with downstream ubiquitylation enzymes In contrast to the E1 conflict, the inventors were unable to model any obvious MUB challenge to other classes of Ub family Ube2D-interacting proteins including HECT E3s, RING E3s, OTUB DUBs, or even pathogen-derived inhibitory kinases, suggesting that MUB bound E2Ub should participate normally in the conjugation pathway until requiring reactivation (FIGS. 5D-E). Nonetheless, these models could benefit from direct biochemical investigation or high-resolution structural analysis. At this time there are many possible allosteric effects on the E2 that the inventors cannot rule out, which warrant further study.

The inventors' current working model is that charged E2s bind to MUBs and then experience slow release and reactivation (FIG. 5E). Structurally, it is clear that the prenylated C-terminus of MUB is not obstructed when E2-bound, affirming how a MUB:E2 complex localizes to the PM. Furthermore, MUB does not obscure the E2 active site Cys; thus, MUB:E2~Ub should be available for substrate modification. MUB:E2 participation in ubiquitylation would add two unique properties: (i) the unavailability of the E2 BBS, and (ii) the obstruction of the E1 binding site, both forces that suppress chain formation. Here, the current gap in knowledge regarding processive Ub chain formation allows measured speculation (Berndsen and Wolberger, 2014; Hochstrasser, 2006). One previously proposed framework for the chain building process is that the difference between mono- and polyubiquitylation is largely determined by E2 turnover rate (Eletr et al., 2005) where slow turnover promotes monoubiquitylation. Based on these data, the inventors predict that MUBs will decrease the turnover rate of E2s they recruit to the membrane. Interestingly, in plants there have recently been a number of important monoubiquitylated PM proteins described, including BORON TRANSPORTER1 (Kasai et al., 2011), IRON-REGULATED TRANSPORTER1 (Barberon et al., 2011), PRR FLAGELLIN-SENSING2 (Lu et al., 2011), and PHOTOTROPIN1 (Roberts et al., 2011). These and other proteins localize near MUBs, at the PM, where monoubiquitylation is prevalent.

MUB Inhibition Occurs at Physiological Concentrations.

Figure 12:
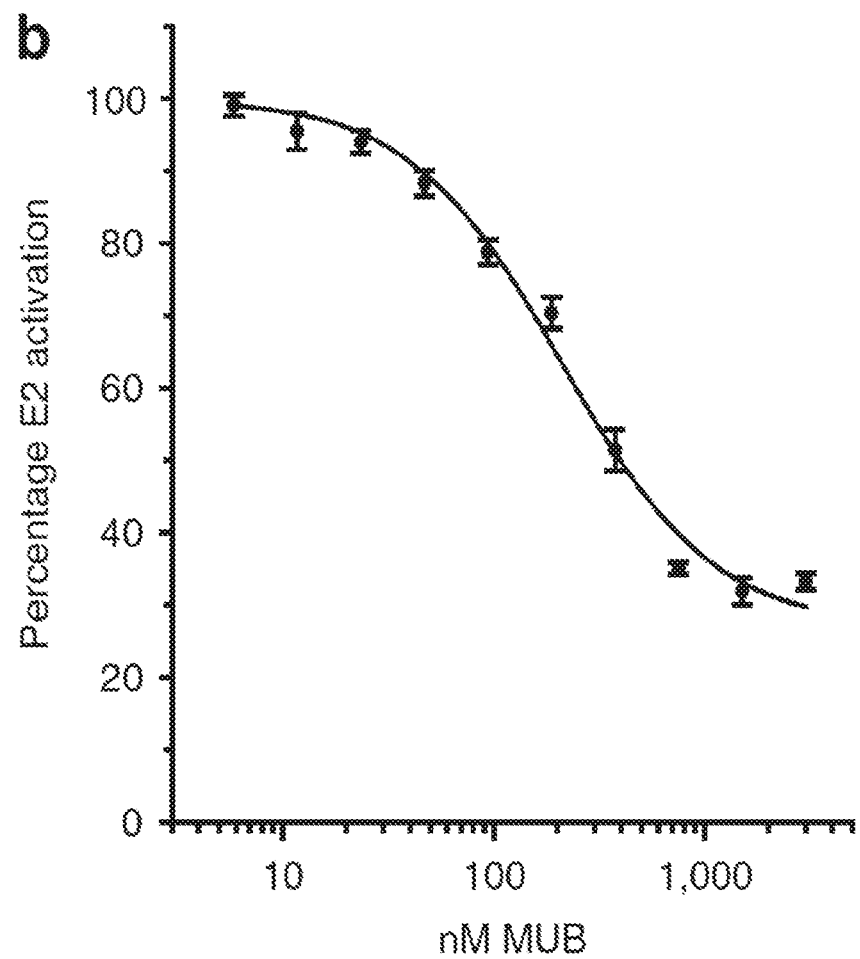
FIG. 12. Ube2D3 Activation. Using HTRF-FRET, Ube2D3 activation was monitored with indicated concentrations of HsMUB to establish an inhibition curve. The initial velocity was linear over the first 10 minutes and is represented as percent E2 activated, with 100% velocity taken in the absence of MUB and 0% in the absence of ATP. Plot represents three independent assays+s.e.m., fit to the one-site binding equation. An additional three assays fit to the Hill equation with coefficient n produced nearly identical results with n1.
Figure 13:
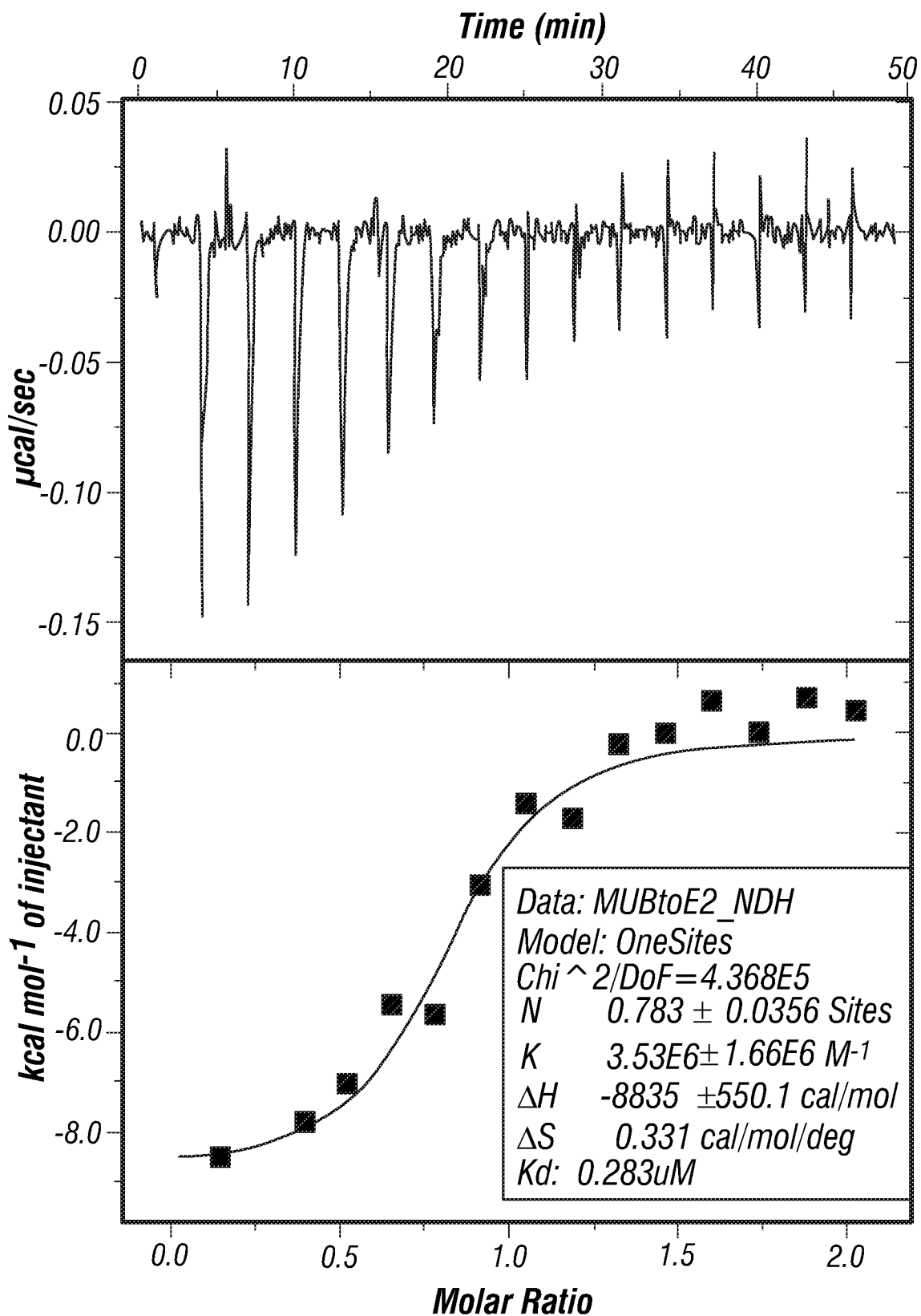
FIG. 13. AtMUB binds AtUBC8 with submicromolar dissociation constant $K_d$ as measured by isothermal titration calorimetry. Isothermal titration calorimetry (ITC) was performed on 8 µM AtUBC8 with 110 µM AtMUB3 as the titrant using a MicroCal iTC200 (GE). Proteins were purified as described for crystallization and dialyzed extensively against a buffer containing 25 mM HEPES, pH 7.5, 200 mM NaCl, 1 mM TCEP. Data was processed with MicroCal Origin 7 software, and normalized against the dialysis buffer's heat of dilution. This plot is representative of 3 independent experiments, which yielded similar results but were performed at different concentrations of NaCl.

To determine the magnitude of MUB inhibition, we investigated HsMUB inhibition of Ube2D3 using an independent method based on Homogeneous Time Resolved Fluorescence—Förster Resonance Energy Transfer (HTRF-FRET). In this assay, fluorescein-labeled Ub behaves as a FRET acceptor once the thioester is formed with biotinylated E2 labeled with a streptavidin-terbium FRET donor. This assay establishes a $K_i$ of 220±16 nM, and demonstrates that up to 70% of Ube2D3 activation can be inhibited (FIG. 12). These results are highly consistent with the PAGE based assays where we typically see low levels of E2 activation even in the presence of saturating MUB. Taken together, they indicate MUB inhibition of E2~Ub formation is conserved and broadly relevant at physiological MUB concentrations in organisms that use the ubiquitylation system.

Example 3—Discussion

Building on the understanding that prenylated MUBs recruit E2s to the PM (Dowil et al., 2011; Downes et al., 2006), the unexpected finding of this work is that MUB exerts high-level regulation on the ubiquitin system in plants and mammals by inhibiting E1 activation of an important E2 subfamily. E2 activation is required for all E3s (Berndsen and Wolberger, 2014); however, it has been generally overlooked as a point of regulation. The current findings suggest that E2 activation is regulated with subcellular precision and raises interesting possibilities for Ub chain formation near the cell surface.

MUBs recruit a critical clade of Ub E2s using the BBS, and suppress their activation using the LBL. The LBL disrupts E1 UFD binding to the E2 and provides an explanation for the inhibition of E2~Ub formation. The AtMUB3:AtUBC8 structure data makes it clear that a prenylated MUB protein could interact with an active E2 while anchored to the PM. Key remaining questions include what substrates are MUB complex-modified, and with what Ub topology. These questions warrant continued study to better understand selective E2 activation by E1s in eukaryotes.

TABLE 1

| Data collection: | |
| --- | --- |
| Wavelength (Å) | 0.97 |
| Space group | P 63 2 2 |
| Unit cell dimensions (Å) | a = b = 135.72 |
| | c = 202.13 |
| Molecules/asymmetric unit | 4 |
| Resolution range (Å) | 50.00-2.8 |
| Unique observations | 27721 |
| Completeness (%)* | 99.8 (100) |
| $R_{sym}$ (%) | 7.2 (7.3) |
| I/s(I) | 11.2 (1.9) |
| Refinement | |
| Resolution (Å) | 10-2.8 |
| $R_{cryst}, R_{free}$* | 0.22 (0.39), 0.26 (0.36) |
| Reflections (working/test) | 25543/1346 |
| Protein atoms | 3720 |
| Sulfate atoms | 30 |
| Rmsd bond lengths (Å) | 0.01 |
| Rmsd angles (Å$^2$) | 1.5 |
| <B> protein (Å$^2$): | 75 |
| Ramachandran plot: | |
| Most favored (%)** | 90.7 |
| Allowed (%) | 7.8 |
| Generously allowed (%) | 1.5 |

*High resolution shell for data collection is 2.8-2.85 and for refinement 2.8-2.87.
**calculated by PROCHECK

TABLE 2

| | P1 | P2 | Surface area (Å$^2$) | Delta G |
| --- | --- | --- | --- | --- |
| current | AtUBC8 | AtMUB3 | 890.6 | −11.7 |
| current | AtUBC8 | AtMUB3 (74-82) | 288.2 | −5.0 |
| 2FUH | HsUbe2D3 | HsUb | 547.2 | −8.3 |

TABLE 2-continued

| | P1 | P2 | Surface area (Å²) | Delta G |
|---|---|---|---|---|
| 1ZGU | HsMMS2 | HsUb | 624.8 | −5.4 |
| 2PE6 | HsUBC9 | HsSUMO1 | 560.4 | −0.2 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Auffret et al., J Alzheimers Dis 19, 1021-1033, 2010.
Barberon et al., (2011). Proceedings of the National Academy of Sciences of the United States of America 108, 8.
Berndsen and Wolberger (2014). Nat Struct Mol Biol 21, 301-307.
Brown et al., Genome Res. (2002). 12: 244-54.
Brzovic and Klevit, (2006). Cell Cycle 5, 2867-2873.
Brzovic et al., (2006). Molecular cell 21, 873-880.
Busso et al., (2005). Anal Biochem 343, 313-321.
Callis, J. (2014). The Arabidopsis Book/American Society of Plant Biologists 12, e0174.
Capili and Lima, (2007a). Current opinion in structural biology 17, 726-735.
Capili and Lima, (2007b). J Mol Biol 369, 608-618.
Das et al., (2009). Mol Cell 34, 674-685.
Das et al., (2013). EMBO J 32, 2504-2516.
Dou et al., (2012). Nat Struct Mol Biol 19, 876-883.
Dowil et al., (2011). J Biol Chem 286, 14913-14921.
Downes et al., (2006). J Biol Chem 281, 27145-27157.
Duncan et al., (2006). EMBO J 25, 1635-1645.
Eddins et al., (2006). Nature structural & molecular biology 13, 915-920.
Eletr et al., (2005). Nat Struct Mol Biol 12, 933-934.
Groettrup et al., (2008). Trends Biochem Sci 33, 230-237.
Guerra and Callis, (2012). Plant physiology 160, 56-64.
Haas et al., (1988). J Biol Chem 263, 13268-13275.
Hatfield et al., (1997). Plant Journal 11, 213-226.
Hibbert et al., (2011). Proc Natl Acad Sci USA 108, 5590-5595.
Hjerten et al., (1956). Archives of biochemistry and biophysics 65, 132-155.
Hochstrasser, M. (2006). Cell 124, 27-34.
Hoege et al., (2002). Nature 419, 135-141.
Huang et al., (2012). Med Oncol 29, 2911-2918.
Ikeda et al., (2010). Cell 143, 677-681.
Jin et al., (2007). Nature 447, 1135-1138.
Kamadurai et al., (2009). Mol Cell 36, 1095-1102.
Kasai et al., (2011). The Journal of biological chemistry 286, 6175-6183.
Kirisako et al., (2006). EMBO J 25, 4877-4887.
Kirkpatrick et al., (2006). Nat Cell Biol 8, 700-710.
Knipscheer et al., (2007a). The EMBO journal 26, 2797-2807.
Knipscheer et al., (2007b). Embo J 26, 2797-2807.
Komander and Rape, (2012). Annu Rev Biochem 81, 203-229.
Kraft et al., (2005). Plant Physiol 139, 1597-1611.
Kus et al., (2004). Proteins 54, 455-467.
Lewis et al., (2006). J Biomol NMR 34, 89-100.
Lu et al., (2011). Science (New York, N.Y.) 332, 1439-1442.
Metzger et al., (2013). Mol Cell 50, 516-527.
Olah et al. (2011). J. Biol. Chem. 286: 34088-100.
Olsen and Lima, (2013). Molecular cell 49, 884-896.
Olsen et al., (2010). Nature 463, 906-912.
Page et al., (2012). Biochemistry 51, 4175-4187.
Pickart et al., (1994). J Biol Chem 269, 7115-7123.
Pruneda et al., (2014). EMBO J 33, 437-449.
Roberts et al., (2011). Plant Cell 23, 3627-3640.
Rodrigo-Brenni and Morgan, (2007). Cell 130, 127-139.
Sakata et al., (2007). Nat Struct Mol Biol 14, 167-168.
Sakata et al., (2010). Structure 18, 138-147.
Saracco et al., (2009). Plant J 59, 344-358.
Smalle and Vierstra, (2004). Ann Rev Plant Biol 55, 555-590.
Stone et al., (2005). Plant Physiol 137, 13-30.
Streich, Jr., and Lima, (2014). Annual review of biophysics 43, 357-379.
Tokgoz et al., (2012). J Biol Chem 287, 311-321.
Valdez-Taubas and Pelham, (2005). Embo J 24, 2524-2532.
Vierstra, R. D. (2012). Plant Physiol 160, 2-14.
Vinarov et al., (2004). Nat Methods 1, 149-153.
Wen et al., (2008). Plant Cell 20, 213-227.
Wiener et al., (2013). Nat Struct Mol Biol 20, 1033-1039.
Ye and Rape, (2009). Molecular cell biology 10, 755-764.

What is claimed is:

1. A method for inhibiting ubiquitin conjugating enzyme activity comprising contacting said ubiquitin conjugating enzyme with a peptide comprising a membrane-anchored ubiquitin-fold lap bar loop (MUB-LBL), wherein the interaction of said peptide and said ubiquitin conjugating enzyme inhibits said ubiquitin conjugating enzyme activity, and wherein said peptide consists of between 8 and 50 amino acids.

2. The method of claim 1, wherein said peptide contains no more than about 30 consecutive amino acids of MUB-LBL.

3. The method of claim 1, wherein said MUB-LBL comprises the sequence LKLPFGKT (SEQ ID NO: 1).

4. The method of claim 1, wherein said peptide is fused to a cell penetrating domain.

5. The method of claim 1, wherein said peptide comprises all L-amino acids.

6. The method of claim 1, wherein said peptide comprises all D-amino acids.

7. The method of claim 1, wherein said peptide comprises a mix of D- and L-amino acids.

8. The method of claim 1, wherein said peptide is 8, 9, 10, 11, 12, 13, 14, 15, 16, 17, 18, 19, 20, 21, 22, 23, 24, 25, 26, 27, 28, 29, 30, 35, 40, 45 or 50 amino acids in length.

9. The method of claim 1, wherein said ubiquitin conjugating enzyme is a mammalian E2 enzyme.

10. The method of claim 1, wherein said ubiquitin conjugating enzyme is a human E2 enzyme.

11. The method of claim 1, wherein said ubiquitin conjugating enzyme is a plant E2 enzyme.

12. The method of claim 1, wherein said ubiquitin conjugating enzyme is located in a cell.

13. The method of claim 12, wherein said cell is located in a mammalian subject.

14. The method of claim 12, wherein said cell is located in a human subject.

15. The method of claim 12, wherein said cell is located in an intact plant.

16. The method of claim 13, wherein said mammalian subject suffers from a disorder involving pathologic ubiquitin activity.

17. The method of claim 16, wherein said disorder is cancer.

18. The method of claim 15, wherein said plant is subject to a disorder involving pathologic ubiquitin activity.

19. The method of claim 15, wherein said plant has nutritional value.

* * * * *